United States Patent
Ji et al.

(10) Patent No.: US 8,586,824 B2
(45) Date of Patent: Nov. 19, 2013

(54) PLANT HOMEODOMAIN PROTEIN-ENCODING GENES AND THEIR USES

(75) Inventors: Lianghui Ji, Singapore (SG); Lin Cai, Singapore (SG); Nam-Hai Chua, New York, NY (US)

(73) Assignee: Temasek Life Sciences Laboratory, Singapore (SG)

( * ) Notice: Subject to any disclaimer, the term of this patent is extended or adjusted under 35 U.S.C. 154(b) by 823 days.

(21) Appl. No.: 12/223,929

(22) PCT Filed: Feb. 13, 2006

(86) PCT No.: PCT/US2006/004777
§ 371 (c)(1),
(2), (4) Date: Aug. 4, 2010

(87) PCT Pub. No.: WO2007/094762
PCT Pub. Date: Aug. 23, 2007

(65) Prior Publication Data
US 2010/0293662 A1    Nov. 18, 2010

(51) Int. Cl.
*A01H 1/00*   (2006.01)
*C12N 15/82*   (2006.01)

(52) U.S. Cl.
USPC .......................................... 800/278; 800/287

(58) Field of Classification Search
None
See application file for complete search history.

(56) References Cited

U.S. PATENT DOCUMENTS

| 6,441,276 B1 * | 8/2002 | Ikeda et al. .................... 800/290 |
| 2003/0188329 A1 * | 10/2003 | Keller et al. ................... 800/278 |
| 2004/0166563 A1 | 8/2004 | Lowe et al. |

FOREIGN PATENT DOCUMENTS

| EP | 1116793 A1 | 7/2001 |
| WO | 0123575 A2 | 4/2001 |
| WO | 03037072 A2 | 5/2003 |
| WO | 2005063990 A2 | 7/2005 |

OTHER PUBLICATIONS

Bowie et al, Science 247:1306-1310, 1990.*
McConnell et al, Nature 411 (6838):709-713, 2001.*
Tao et al (2004, PNAS 100 (14): 5164-5169).*
2. Replacing 1. Written Opinion dated Mar. 19, 2012 in the Austrian Application No. 200805946-1, 8 pages.

\* cited by examiner

*Primary Examiner* — Stuart F Baum
(74) *Attorney, Agent, or Firm* — Rothwell, Figg, Ernst & Manbeck, P.C.

(57) ABSTRACT

A group of genes including GhCIR1 from cotton (*Gossypium hirsutum*), and AtCIR1 and AtCIR2 from *Arabidopsis thaliana* promote shoot regeneration in plants even in the absence of cytokinin. In the presence of cytokinin, the genes significantly improve transformation efficiency. The genes can be used as an enhancer as well as a selectable marker of transformation in plants. The proteins encoded by the novel genes have a homeodomain (HD) at the N-terminus and a highly divergent domain at the C-terminus. The proteins share a common structural motif.

16 Claims, 11 Drawing Sheets

```
1    ------------------------------------------------------------ GhCR1
1    ------------------------------------------------------------ AtWOX2
1    ------------------------------------------------------------ At3g11260
1    -----MKVHEFSNGFSSSWDQHDSTSSLSLSCKRLRPLAPKLSGSPPSPPSSSSGVTSAT At1g46480
1    ------------------------------------------------------------ PRS
1    ------------------------------------------------------------ WUS
1    ------------------------------------------------------------ PhWUS
1    ------------------------------------------------------------ LeWUS
1    ------------------------------------------------------------ P0529E05.28
1    ------------------------------------------------------------ Seq.ID3
1    ------------------------------------------------------------ Seq.ID5
1    ------------------------------------------------------------ Seq.ID7
1    ------------------------------------------------------------ Seq.ID9
1    ------------------------------------------------------------ Seq.ID13
1    ------------------------------------------------------------ Seq.ID15
1    ------------------------------------------------------------ Seq.ID17
1    ------------------------------------------------------------ Seq.ID19
1    MLKLSMKVHQFARG---FWEHEP---SLTLGCKRLRPLAPKLSNTDTISPPHH---PVTT Seq.ID21
1    ----MMKVHQFTRGL--IWEHEP---FLTLGCKRLRPLAPKLPNTKTITT-------P-- Seq.ID23
1    ------------------------------MEG---GGGGGGGGGN------------- GhCR1
1    ------------------------------MEN--EVNAGTASS--------------- AtWOX2
1    -----------------------------MSFSVKGRSLRGNNNGG------------- At3g11260
56   FDLKNFIRPDQTGPTKF---------EHKRDPP---HQLETH---------PGG----- At1g46480
1    ------------------------------MSPVAS----------------------- PRS
1    -------------MEPPQH-Q---------HHHHQADQ----ESGNNNNKSGSGGYT-- WUS
1    ------------METAQHQQNNQQHYLHQHLSIGQGTNIEDGS--NKNNSSNFM------ PhWUS
1    -------------------------MEHQH--N-----IEDGGK-NSNNS--FL----- LeWUS
1    ------------------------------MEALSGR---------------------- P0529E05.28
1    ------------------------------MEALSGR---------------------- Seq.ID3
1    ------------------------------MAANAGGGGAGGGSGSGSVAAPA Seq.ID5
1    ------------------------------MAANAGGGGAGGGSGSGSVAAPA Seq.ID7
1    ------------------------------MEGG----------LSPERHA------- Seq.ID9
1    -----------------------------------MASA-------------------- Seq.ID13
1    ---------------------MESSHSTAEDESGWKGSSGAHSSV-------------- Seq.ID15
1    ----------------------MES-HSTAEDESGWKGSSGAHSSV------------- Seq.ID17
1    ----------------------MESHSSDAEAEN-----VRTHSSV------------- Seq.ID19
52   FDLKSFIKPE-SASRKLGIGSSDDNTNKRDPSSPQGQAETHI---------PGG----- Seq.ID21
43   FDLKSFIRPE-SGPRKP--VSSDD--TKKDPPSPQGQIETH---------PGG------ Seq.ID23
13   ------SRWNPTKEQISMLESIYK-QGIRTPSADQIQQITSRLKAYGITEGKNVFYWFQN GhCR1
13   ------SRWNPTKDQITILENLYK-EGIRTPSADQIQQITGRIRAYGHIEGKNVFYWFQN AtWOX2
18   -TGTKCGRWNPTVEQLKILTDLFR-AGLRTPTTDQIQKISTELSFYGKIESKNMFYWFQN At3g11260
89   -----TRWNPTQEQIGILEMLYK-GGMRTPNAQQIEHITLQLGKYYGHIEGKNMFYWFQN At1g46480
7    ------TRWCPTPEQLMILEEMYR-SGIRTPNAVQIQQITAHLAFYGKIESKNMFYWFQN PRS
31   -CRQTSTRWTPTTEQIKILKELYYNNAIRSPTADQIQKITARLRQFGKIEGKNVFYWFQN WUS
41   -CRQNSTRWTPTTDQIRILKDLYYNNGVRSPTAEQIQRISAKLRQYGKIEGKNVFYWFQN PhWUS
20   -CRQSSSRFTPTSDQIRILKDLYYNNGVRSPTAEQIQRISAKLRQYGKIEGKNVFYWFQN LeWUS
8    -VGVKCGRWNPTIAEQVKVLTELFR-AGLRTPSTEQIQRISTHLSAFGKVESKNMFYWFQN P0529E05.28
8    -VGVKCGRWNPTIAEQVKVLTELFR-AGLRTPSTEQIQRISTHLSAFGKVESKNMFYWFQN Seq.ID3
24   VCRPSGSRWTPTPEQIRMLKELYYGCGIRSPSSEQIQRITAMIRQHGKIEGKNVFYWFQN Seq.ID5
24   VCRPSGSRWTPTPEQIRMLKELYYGCGIRSPSSEQIQRITAMIRQHGKIEGKNVFYWFQN Seq.ID7
12   AAEPVRSRWTEKPEQILILESIFN-SGMVNPPKDETVRIRKLLERFGAVGDANVFYWFQN Seq.ID9
5    ------DATA-TREQVAVLEGLYE-HGLRTPSAEQIQQITGRLREHGAIEGKNVFYWFQN Seq.ID13
25   ------SRWSPTKEQIDMLENFYK-QGIRTPSTEQIQQITSRLRAYGVIEGKNVFYWFQN Seq.ID15
24   ------SRWSPTKEQIDMLENFYK-QGIRTPSTEQIQQITSRLRAYGVIEGKNVFYWFQN Seq.ID17
20   ------SRWSPTKEQIDMLENLYK-QGIRTPSTEQIQQITSRLRAYGHIEGKNVFYWFQN Seq.ID19
96   ------TRWNPTQEQIGILEMLYK-GGMRTPNAQQIEQITAQLSKYGKIEGKNMFYWFQN Seq.ID21
82   ------TRWNPTQEQIGILEMLYK-GGMRTPNAQQIEQITVQLGKYGKIEGKNMFYWFQN Seq.ID23
```

FIG. 2A

```
 66 HKARQR---QKQ--KQEN----------IAYINRY-------IH-------------- GhCR1
 66 HKARQR---QKQ--KQER----------MAYFNRL-------LH-------------- AtWOX2
 76 HKARER---QKI-RRK------------------------------------I---- At3g11260
142 HKARER---QKQKR--------------NNL-----IS-------------------- At1g46480
 60 HKARDR---QKLRKK----------LAKQL------HQQ------------------- PRS
 90 HKARER---QKKRFNGTNM-TTPSSSPNSVMMAANDHYHPLLHHHGVPMQRPANSVNVK WUS
100 HKARER---QKKRLIAAAT-TDNTNLPMQMQFQR-----------GVWRSSADDPI--- PhWUS
 79 HKARER---QKKRLIAAAS-ATDNNNISSMQMIP-----------HLWRS-PDD----- LeWUS
 66 HKARERHHHKKRRRGASS--PDSGS------ND------------D--DGRAAA---- P0529E0528
 66 HKARERHHHKKRRRGASSS-SPDSGSGRGSNNE------------E--DGRGAAS--- Seq.ID3
 84 HKARER---QKRRLTSLDVNVPAAGAADATTSQLG----------------------- Seq.ID5
 84 HKARER---QKRRLTSLDVNVPAAGAADATTSQLG----------------------- Seq.ID7
 71 RRSRSRR-QRQLQAVAAASSSSSGS-----------PPTSGLAPGHATASST------ Seq.ID9
 57 HKARQR---QRQ--KQDS----------FAYFSRL-LRRPPPLPVLSMPPAPP----- Seq.ID13
 78 HKARQR---QKLQKQQS-----------IAYCNCF-LH-------------------- Seq.ID15
 77 HKARQR---QKLQKQQS-----------IAYCNCF-LH-------------------- Seq.ID17
 73 HKARQR---QKL-MKQQT----------IAYSNRF-LR-------------------- Seq.ID19
149 HKARER---QKQKR--------------NNG-----LA-------------------- Seq.ID21
135 HKARER---QKQKR--------------SS------LAS------------------- Seq.ID23

88 ---HHHRAQPV------FHPPP----------------CTN----VVCAG-------- GhCR1
 88 ---KTSR---F------FYPPP----------------CSN----VGCVS-------- AtWOX2
 88 ----SID--------------------------------------------------- At3g11260
158 ------LSCQSSFTTTGVFN-PSVT-----------MKTRTSSSLDIMREPMV----- At1g46480
 80 -----QHQLQLQLQQIKP-KPISS-----------MISQP-----------VN----- PRS
146 LNQDHHLYHHN---K----PYPSFNNG----NLNHASSGTECG--------------- WUS
141 ---HHKY------TNP---------------GVHCPSASSHGVL------------- PhWUS
117 ---HHKYNTA---T----TNP----------GVQCPSPSSHGVL------------- LeWUS
 98 ----HEG-------DADLVLQPPE-----------------SK-------RE------ P0529E0528
106 ---QSHDAD----ADADLVLQPPE-----------------SK-------RE------ Seq.ID3
116 --------VLSLSSPPPSGAAPPSPTLGLYAAGNGGGSAVLLDTSSDWGSSGAAMATETC Seq.ID5
116 --------VLSLSSPPPSGAAPPSPTLGFYAAGNGGGSAVLLDTSSDWGSSGAAMATETC Seq.ID7
112 AGMFAHG--ATYGSSASAWPPPPSCEGMMGDLDYGGGDDLFAISRQMG---------- Seq.ID9
 94 ---YHHARVPAPPAIPMPMAPPPPA---------------ACNDNGGARVIYRN---- Seq.ID13
102 ---ASH-----------PI---------------CQN----VVCV------------ Seq.ID15
101 ---ASH-----------PI---------------CQN----VVCAP----------- Seq.ID17
 96 ---ASH-----------PI---------------CQN----VACAP----------- Seq.ID19
165 ----HSPRTTLTTSPPFSCCVITT-----------MDTTK------RGEVV------- Seq.ID21
151 ----SHSPRTPTIHS----VVT-------------LETT-------RGEVV------- Seq.ID23

109 ---------PYFVPQA-DHHH-----HLGF---YP--------QCPKVL--LPS---- GhCR1
106 ---------PYYLQQASDHHMNQ---HGSV---YTND----LLHRNNVM--IPSGGYE AtWOX2
 91 -------------FDHHHQPS-----------TRDVF--EISE-------E--DCQE At3g11260
193 EKEELVEENEY----------------------------------------------- At1g46480
105 KN-IIDHHNPYHHHHHNHHHHHRPYDMSEDCCSHPSPMC-LPHQGTGVGEAPSKVMN PRS
178 ---VVNASNGYM----SSHVYG--SMEQ---DCSMN--------YNNVGGGWANMDHHY WUS
161 --AVGQNGN-------HGYGTLAMEKSFRDCSISPGSSMSHHHHQNFA--WAGVDPYS PhWUS
141 --PVVQTGN-------YGYGTLAMEKSFRECSISPPGGS---YHQNLT--WVGVDPYN LeWUS
115 --------ARSYGHHRLMTC--------YIVRDVV--ET--------EAMW------ P0529E0528
127 --------ARSYGHHRLVTC--------YIVRDVV--EQQE--A--SPSW------- Seq.ID3
168 FLQVGAVVRSFLGHCAQFHVRTYELIAASFHPPVYITVRYGGARPODYMGVTDTGSSSQW Seq.ID5
168 FLQVGAVVRSFLGHCAQFHVRTYELIAASFHPPVYITVRYGGARPODYMGVTDTGSSSQW Seq.ID7
159 --YASGGGSGSASSAAVAHEQQQQLYYS----PCQPASMTVFIN-------------- Seq.ID9
130 ---------PFYVAAPQAPPAN-----AAYY---YPQP--QQQQQQ----------- Seq.ID13
114 ---------------------------------------------------------- Seq.ID15
114 ---------YCLQKS-------GFSF---YP----HQPKVL-ASVG------------ Seq.ID17
109 ---------YCLQRS-------GFSF---YP----QQSKVL-ASGG------------ Seq.ID19
195 ER-E-EEDSP------------------------------------------------ Seq.ID21
174 ER-DHEEDSPY----------------------------------------------- Seq.ID23
```

FIG. 2B

```
135 -RSIKRRGR------------P----IGKTGKSLFYNGNAY-DHTM-VPS-PDTENLYI GhCR1
143 KRTVTQHQKQLSDIRTTAATRMP----ISPS--SLRFDRFALRDHCY-AG--ED-IN--- AtWOX2
114 E------------------------------------------------------------ At3g11260
204 KRTCRSWGFENLEIENRR--NKNS-STM---------------------------ATTF At1g46480
162 EYYCTKSGAEEILMQKSI--TGPN-SSYGRDW--------MMMMDMGP-RPSYPSSSSSPI PRS
217 ----------------SSAPYNFFDRAK--------------------PLFGLEGHQDE WUS
208 ----------------STTTYPFLEKT----------------KLFENETLEADE-EQQE PhWUS
185 NM----------STTSPATYPFLEKSNN----------------KHYE-ETL--DE-EQEE LeWUS
140 ER---------------P------------------------------------------ P0529E05.28
155 ER---------------P------------------------------------------ Seq.ID3
228 PRFSSSDTIMAAA                                                 Seq.ID5
228 PRFASSDTIM                                                    Seq.ID7
198 G-------------VATEVPRGP-IDLRSMFG----------------------------- Seq.ID9
157 --------------QVTVMYQYPRMEVAGQDKMMTRAAAHQQQQE---------------- Seq.ID13
114 ------------------------------------------------------------ Seq.ID15
136 ---ISSRIE------TG----S----FGMLR---ICDGMQS-EP-------PD------- Seq.ID17
131 ---ISS---------TG----P----IGMQR---MFDGMQSSEP-------PD------- Seq.ID19
203 LKKCRSWAFEYLEDQ--------------------------------------------- Seq.ID21
184 KKKCRRWVFDCLEEQN-------------------------------------------- Seq.ID23
174 GAFNNGGGATNHH----ETLPLFPLHPTGVSEETL------MASSSPTGSTSCETTIISA GhCR1
190 --VNSSG----R----KTLPLFPLQPLNASNADG------MGSSS-----------FA AtWOX2
115 ------------EKVIETLQLFPVNSFEDSNSKV----DKMR--ARGNNQY-------- At3g11260
233 NKII----------DNVTLELFPLHPGR-------------------------------- At1g46480
211 SCCNMMMS----SPKIPLKTLELFPISSINSKQDSTKL                        PRS
240 EECGGDAYLEHRR------TLPLFPMHGEDHIN----------GGSGAIWKYGQ WUS
235 EDQ---ENYYYQRTTSAIETLPLFPMHEENISS-------FCNLKHQESSGGFYTENYRAD PhWUS
216 EN-------YQRGNSALETISLFPMHEENIISN-------FC-IKHHESSGG----WYHSD LeWUS
143 ----------TREVETLELFPLKSY-DLEV-----DKVR-YVRGGGG------- P0529E05.28
158 ----------TREVETLELFPLKSYGDLEAA-----EKVRSYVRGIAAT------- Seq.ID3
240                                                               Seq.ID5
237                                                               Seq.ID7
216 -----------QDVMLVHSTAGLLPVNEYGVLTQSLQMGESYFLVTRGY Seq.ID9
188 ---NGAGQQPGRAGHPSRETLQLFP-P----------PAHLRAAAR----------- Seq.ID13
114 -----------------------------HIVCKRVDSAFI------------------ Seq.ID15
161 --YNYST--SNR------EALTLEPLHPTGILEEKTTHHSVDVTDKSFVS---------- Seq.ID17
154 --QN------R------EVLTLFPLHPTGILKEKTTHQVPSIASTSVVA---------- Seq.ID19
218 ------------REEEHRTLELFPLHPEGR----------------------------- Seq.ID21
200 ----MSSP----CEQEEHRTLELFPLHPEGR----------------------------- Seq.ID23
223 GGVDN-HESNNEGSG-EHREIDEF GhCR1
221 LGSDSPVDCSSDGAGREQPIIDEFSGGSTSTRFDSNGNGL AtWOX2
148 ----------REYIRETTTTSESPYSSCGAEMEHPPPLDLRLSFL. At3g11260
251                                                               At1g46480
244                                                               PRS
278 SE--VRPCAS------LELRLN WUS
286 DN-LAAARAS------LELSLNSEIGNSS PhWUS
258 NNNLAA---------LELTLNSEP LeWUS
173 ----------EQCREISEFDVAAG--------RDPPLELRLCSFGL P0529E05.28
192 ----------SEQCRELSEFDVSAG--------RDPPLELRLCSFGP Seq.ID3
240                                                               Seq.ID5
237                                                               Seq.ID7
253                                                               Seq.ID9
220 -----------QGARRQRQ Seq.ID13
126 -----------LTNQRCLQV Seq.ID15
201 ------IAVDENGHLGNQPCFNEDY Seq.ID17
189 ------VD--EDGHLGNQPEFNEFTTEPRSRE Seq.ID19
235                                                               Seq.ID21
222                                                               Seq.ID23
```

FIG. 2C

 
FIG. 7A   FIG. 7B
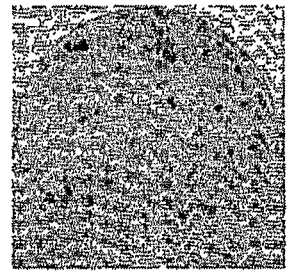 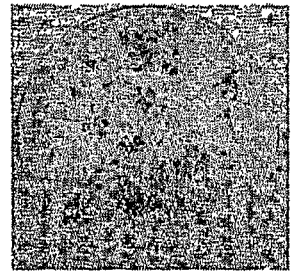
FIG. 7C   FIG. 7D

SEQUENCE LISTING

```
<160> NUMBER OF SEQ ID NOS: 68

<210> SEQ ID NO 1
<211> LENGTH: 1010
<212> TYPE: DNA
<213> ORGANISM: Gossypium hirsutum

<400> SEQUENCE: 1
ggcgcgccgg acactgactt ggactgaagt agtagaaaaa ttcccatgcc aatcgctata      60
caccctcctt atttttttc tttttaaacc aaactcccaa aaccctactc caataatcaa     120
tcaaaatcca aatcaaaccc tcattttctt tatctgcaaa tggaaggtgg cggcggcggc     180
ggtggtggag ggaattcacg gtggaacccg acgaaggagc aaataagcat gcttgaaagc     240
ttgtacaagc aagggataag aaccccaagt gctgatcaga tacagcaaat aaccagtagg     300
ctcaaagctt atggcaccat tgaaggcaaa aacgtgttct attggttcca aaatcataaa     360
gctcgtcaaa ggcagaaaca aaagcaagag aatttggctt atatcaaccg ttacattcac     420
catcatcatc gagctcaacc tgttttcat cctcctcctt gcaccaatgt tgtttgtgct     480
ggtccatatt ttgtaccaca agctgatcat caccatcatc taggcttta ccctcagtgt     540 cccaaggttc ttctccctag tagatcaatt aaaagaagag gcaggcctat tggtaaaact     600
ggaaagtctc tattttacaa cggaaatgct tatgatcata ccatggttcc atcacctgat     660
actgaaaact tatacactgg agcattcaac aatggcggcg gcgccactaa tcatcacgag     720
acattgccat tgtttccatt gcacccgact ggtgtttccg aagagacgtt aatggcttca     780
tcatcaccaa ctggttcaac ttcatgtgag acgacgatat ctgctggtgg tgttgataac     840
catgaaagta ataatgaagg ttctggggaa catcgtttca ttgatttctt ctgaaagtga     900
```

```
ttgggggtg ggggaggaaa tggaaataaa aatcaagggt tttgattcaa agaacattga    960
tttatggaat taatggccat ttgagtattt gaaaaaaaaa aaaaaaaaa              1010

<210> SEQ ID NO 2
<211> LENGTH: 244
<212> TYPE: PRT
<213> ORGANISM: Gossypium hirsutum

<400> SEQUENCE: 2

Met Glu Gly Gly Gly Gly Gly Gly Gly Asn Ser Arg Trp Asn
1               5                   10                  15

Pro Thr Lys Glu Gln Ile Ser Met Leu Glu Ser Leu Tyr Lys Gln Gly
            20                  25                  30

Ile Arg Thr Pro Ser Ala Asp Gln Ile Gln Gln Ile Thr Ser Arg Leu
        35                  40                  45

Lys Ala Tyr Gly Thr Ile Glu Gly Lys Asn Val Phe Tyr Trp Phe Gln
    50                  55                  60

Asn His Lys Ala Arg Gln Arg Gln Lys Gln Glu Asn Leu Ala
65                  70                  75                  80

Tyr Ile Asn Arg Tyr Ile His His His Arg Ala Gln Pro Val Phe
                85                  90                  95

His Pro Pro Cys Thr Asn Val Val Cys Ala Gly Pro Tyr Phe Val
            100                 105                 110

Pro Gln Ala Asp His His His Leu Gly Phe Tyr Pro Gln Cys Pro
        115                 120                 125

Lys Val Leu Leu Pro Ser Arg Ser Ile Lys Arg Arg Gly Arg Pro Ile
    130                 135                 140

Gly Lys Thr Gly Lys Ser Leu Phe Tyr Asn Gly Asn Ala Tyr Asp His
145                 150                 155                 160

Thr Met Val Pro Ser Pro Asp Thr Glu Asn Leu Tyr Thr Gly Ala Phe
                165                 170                 175

Asn Asn Gly Gly Gly Ala Thr Asn His His Glu Thr Leu Pro Leu Phe
            180                 185                 190

Pro Leu His Pro Thr Gly Val Ser Glu Glu Thr Leu Met Ala Ser Ser
        195                 200                 205

Ser Pro Thr Gly Ser Thr Ser Cys Glu Thr Thr Ile Ser Ala Gly Gly
    210                 215                 220

Val Asp Asn His Glu Ser Asn Asn Glu Gly Ser Gly Glu His Arg Phe
225                 230                 235                 240

Ile Asp Phe Phe

<210> SEQ ID NO 3
<211> LENGTH: 1236
<212> TYPE: DNA
<213> ORGANISM: Arabidopsis thaliana

<400> SEQUENCE: 3
ggcgcgccat ggaaaacgaa gtaaacgcag gaacagcaag cagttcaaga tggaacccaa    60
cgaaagatca gatcacgcta ctggaaaatc tttacaagga aggaatacga actccgagcg   120
ccgatcagat tcagcagatc accggtaggc ttcgtgcgta cggccatatc gaaggtaaaa   180 acgtcttta  ctggttccag aaccataagg ctaggcaacg ccaaaagcag aaacaggagc   240
gcatggctta cttcaatcgc ctcctccaca aaacctcccg tttcttctac ccccctcctt   300
gctcaaacgg cacgtagttc ttatccttt ctcttactta tccgtatcta atcttcgacg   360
ttctatttta taatcttaaa aaaattgtag tccatacgtt ataggttctt tttgttgacg   420
```

-continued

```
acgttttctt tccgtattaa agaaatgaaa ataaagcgta tgaattacat ctggactatg    480
aaagaactta caaaaacatg tcattaaata catatataaa tatataatcc agttttggcc    540
atttatcgct gagattcaaa tttgtttttt aaaattttaa cataaaaaca tataatcgga    600
tgcgaaagga ttatatcata tgggactatt ttgagatgtt tatcagcaaa ttatgtactc    660
tggattagca ggttttatgt ttgttttttc atttttatca atataattgg gtattactaa    720
ataaaatctt ttttttggtt atgaagtggg ttgtgtcagt ccgtactatt tacagcaagc    780
aagtgatcat catatgaatc aacatggaag tgtatacaca aacgatcttc ttcacagaaa    840
caatgtgatg attccaagtg gtggctacga gaaacggaca gtcacacaac atcagaaaca    900
actttcagac ataagaacaa cagcagccac aagaatgcca atttctccga gttcactcag    960
atttgacaga tttgccctcc gtgataactg ttatgccggt gaggacatta acgtcaattc    1020
cagtggacgg aaaacactcc ctcttttttcc tcttcagcct ttgaatgcaa gtaatgctga    1080
tggtatggga agttccagtt ttgcccttgg tagtgattct ccggtggatt gttctagcga    1140
tggagccggc cgagagcagc cgtttattga tttcttttct ggtggttcta cttctactcg    1200
tttcgatagt aatggtaatg ggttgtaatt aattaa                              1236
```

<210> SEQ ID NO 4
<211> LENGTH: 260
<212> TYPE: PRT
<213> ORGANISM: Arabidopsis thaliana

<400> SEQUENCE: 4

```
Met Glu Asn Glu Val Asn Ala Gly Thr Ala Ser Ser Arg Trp Asn
1               5                   10                  15

Pro Thr Lys Asp Gln Ile Thr Leu Leu Glu Asn Leu Tyr Lys Glu Gly
            20                  25                  30

Ile Arg Thr Pro Ser Ala Asp Gln Ile Gln Gln Ile Thr Gly Arg Leu
        35                  40                  45

Arg Ala Tyr Gly His Ile Glu Gly Lys Asn Val Phe Tyr Trp Phe Gln
    50                  55                  60

Asn His Lys Ala Arg Gln Arg Gln Lys Gln Lys Gln Glu Arg Met Ala
65                  70                  75                  80

Tyr Phe Asn Arg Leu Leu His Lys Thr Ser Arg Phe Phe Tyr Pro Pro
                85                  90                  95

Pro Cys Ser Asn Val Gly Cys Val Ser Pro Tyr Tyr Leu Gln Gln Ala
            100                 105                 110

Ser Asp His His Met Asn Gln His Gly Ser Val Tyr Thr Asn Asp Leu
        115                 120                 125

Leu His Arg Asn Asn Val Met Ile Pro Ser Gly Gly Tyr Glu Lys Arg
    130                 135                 140

Thr Val Thr Gln His Gln Lys Gln Leu Ser Asp Ile Arg Thr Thr Ala
145                 150                 155                 160

Ala Thr Arg Met Pro Ile Ser Pro Ser Ser Leu Arg Phe Asp Arg Phe
                165                 170                 175

Ala Leu Arg Asp Asn Cys Tyr Ala Gly Glu Asp Ile Asn Val Asn Ser
            180                 185                 190

Ser Gly Arg Lys Thr Leu Pro Leu Phe Pro Leu Gln Pro Leu Asn Ala
        195                 200                 205

Ser Asn Ala Asp Gly Met Gly Ser Ser Phe Ala Leu Gly Ser Asp
    210                 215                 220

Ser Pro Val Asp Cys Ser Ser Asp Gly Ala Gly Arg Glu Gln Pro Phe
225                 230                 235                 240
```

Ile Asp Phe Phe Ser Gly Gly Ser Thr Ser Thr Arg Phe Asp Ser Asn
            245                 250                 255

Gly Asn Gly Leu
        260

<210> SEQ ID NO 5
<211> LENGTH: 708
<212> TYPE: DNA
<213> ORGANISM: Arabidopsis thaliana

<400> SEQUENCE: 5
ggcgcgccag ttgaggactt tacatctgaa catgtctttc tccgtgaaag gtcgaagctt      60
acgtggcaac aataacggag gaacggggac gaagtgcggg agatggaatc caacggtgga     120
gcagttgaag atattgactg atctgtttcg agccggtctt agaactccaa caactgatca     180
gattcagaag atctctacgg agctcagttt ctacggcaag atagagagca agaatgtttt     240
ctattggttt cagaatcata aggctaggga gaggcagaaa cgtcgtaaaa tctccattga     300
ttttgatcat catcatcatc aaccatcaac tagagatgtt tttgaaataa gcgaagaaga     360
ttgtcaagag gaagagaagg tgatagagac attacaactc tttccggtga attcatttga     420
agactccaac tccaaggtgg acaaaatgag agctagaggc aataaccagt accgtgaata     480
tattcgagag accaccacga cgtcgttttc tccatactca tcatgtggag ctgaaatgga     540
acatccaccg ccattagatc ttcgattaag ctttctttaa gtcattgacc acaataacaa     600
aagaaaaaaa acagatgctt tagcctttaa aatgttgttg tattttgaat tatgacatat     660
tatccgatgc atggtttatg agatattttc caatgcatgg ttaattaa                  708

<210> SEQ ID NO 6
<211> LENGTH: 182
<212> TYPE: PRT
<213> ORGANISM: Arabidopsis thaliana

<400> SEQUENCE: 6

Met Ser Phe Ser Val Lys Gly Arg Ser Leu Arg Gly Asn Asn Asn Gly
1               5                   10                  15

Gly Thr Gly Thr Lys Cys Gly Arg Trp Asn Pro Thr Val Glu Gln Leu
            20                  25                  30

Lys Ile Leu Thr Asp Leu Phe Arg Ala Gly Leu Arg Thr Pro Thr Thr
        35                  40                  45

Asp Gln Ile Gln Lys Ile Ser Thr Glu Leu Ser Phe Tyr Gly Lys Ile
    50                  55                  60

Glu Ser Lys Asn Val Phe Tyr Trp Phe Gln Asn His Lys Ala Arg Glu
65                  70                  75                  80

Arg Gln Lys Arg Arg Lys Ile Ser Ile Asp Phe Asp His His His His
                85                  90                  95

Gln Pro Ser Thr Arg Asp Val Phe Glu Ile Ser Glu Glu Asp Cys Gln
            100                 105                 110

Glu Glu Glu Lys Val Ile Glu Thr Leu Gln Leu Phe Pro Val Asn Ser
        115                 120                 125

Phe Glu Asp Ser Asn Ser Lys Val Asp Lys Met Arg Ala Arg Gly Asn
    130                 135                 140

Asn Gln Tyr Arg Glu Tyr Ile Arg Glu Thr Thr Thr Thr Ser Phe Ser
145                 150                 155                 160

```
Pro Tyr Ser Ser Cys Gly Ala Glu Met Glu His Pro Pro Leu Asp
            165                 170                 175

Leu Arg Leu Ser Phe Leu
            180

<210> SEQ ID NO 7
<211> LENGTH: 775
<212> TYPE: DNA
<213> ORGANISM: Arabidopsis thaliana

<400> SEQUENCE: 7
ggcgcgccaa aatgaaggtt catgagtttt cgaatgggtt ttcttcatcg tgggatcaac    60
atgactcgac atcatccctt agcctaagct gcaaacgcct ccgtcctctc gcccctaagc   120
tctccggcag ccctccctcc cctccttctt cttcctccgg cgtcacttca gccacttttg   180
accttaaaaa cttcattaga cccgatcaaa ccggtccgac aaaatttgaa cacaaacgag   240
accctcctca tcaattggag acgcaccccg gagggacaag gtggaacccg actcaagaac   300
agatagggat acttgagatg ttgtacaaag gtggaatgcg tactcctaat gctcaacaga   360
ttgagcatat cacattgcaa ctcggtaagt acgggaaaat cgaagggaaa aatgtgttct   420
attggttcca gaaccacaaa gcccgcgaga cacagaagca agaggaac aacctcatca    480 gcctaagttg ccaaagcagc ttcacgacca ctggtgtctt taatccgagt gtaactatga   540
agacaagaac atcatcgtca ctagacatta tgagagaacc aatggtggag aaggaggagt   600
tagtggaaga gaatgagtac aagaggacat gtaggagctg gggatttgag aacttggaga   660
tagagaacag gagaaacaaa aatagtagta ctatggcaac tacttttaat aaaatcattg   720
acaatgtaac cctcgagctt tttcctctcc atcctgaagg gagatgatta attaa        775

<210> SEQ ID NO 8
<211> LENGTH: 251
<212> TYPE: PRT
<213> ORGANISM: Arabidopsis thaliana

<400> SEQUENCE: 8

Met Lys Val His Glu Phe Ser Asn Gly Phe Ser Ser Trp Asp Gln
1               5                   10                  15

His Asp Ser Thr Ser Ser Leu Ser Leu Ser Cys Lys Arg Leu Arg Pro
            20                  25                  30

Leu Ala Pro Lys Leu Ser Gly Ser Pro Pro Ser Pro Pro Ser Ser Ser
        35                  40                  45

Ser Gly Val Thr Ser Ala Thr Phe Asp Leu Lys Asn Phe Ile Arg Pro
    50                  55                  60

Asp Gln Thr Gly Pro Thr Lys Phe Glu His Lys Arg Asp Pro Pro His
65                  70                  75                  80

Gln Leu Glu Thr His Pro Gly Gly Thr Arg Trp Asn Pro Thr Gln Glu
                85                  90                  95

Gln Ile Gly Ile Leu Glu Met Leu Tyr Lys Gly Gly Met Arg Thr Pro
            100                 105                 110

Asn Ala Gln Gln Ile Glu His Ile Thr Leu Gln Leu Gly Lys Tyr Gly
        115                 120                 125

Lys Ile Glu Gly Lys Asn Val Phe Tyr Trp Phe Gln Asn His Lys Ala
    130                 135                 140

Arg Glu Arg Gln Lys Gln Lys Arg Asn Asn Leu Ile Ser Leu Ser Cys
145                 150                 155                 160

Gln Ser Ser Phe Thr Thr Thr Gly Val Phe Asn Pro Ser Val Thr Met
                165                 170                 175
```

```
Lys Thr Arg Thr Ser Ser Ser Leu Asp Ile Met Arg Glu Pro Met Val
            180                 185                 190

Glu Lys Glu Glu Leu Val Glu Glu Asn Glu Tyr Lys Arg Thr Cys Arg
        195                 200                 205

Ser Trp Gly Phe Glu Asn Leu Glu Ile Glu Asn Arg Arg Asn Lys Asn
    210                 215                 220

Ser Ser Thr Met Ala Thr Thr Phe Asn Lys Ile Ile Asp Asn Val Thr
225                 230                 235                 240

Leu Glu Leu Phe Pro Leu His Pro Glu Gly Arg
                245                 250

<210> SEQ ID NO 9
<211> LENGTH: 689
<212> TYPE: DNA
<213> ORGANISM: Artificial Sequence
<220> FEATURE:
<223> OTHER INFORMATION: Synthetic Construct, Chimera of GhCIR1 HD
      domain and VP16 activation domain

<400> SEQUENCE: 9
ggcgcgccgg acactgactt ggactgaagg agtagaaaaa ttcccatgcc aatcgctata      60
caccctcctt atttttttc ttttttaaacc aaactcccaa aaccctactc caataatcaa     120
tcaaaatcca aatcaaaccc tcattttctt tatctgcaaa tggaaggtgg cggcggcggc     180
ggtggtggag ggaattcacg gtggaacccg acgaaggagc aaataagcat gcttgaaagc     240
ttgtacaagc aagggataag accccaagt gctgatcaga tacagcaaat aaccagtagg     300
ctcaaagctt atggcaccat tgaaggcaaa aacgtgttct attggttcca aaatcataaa     360
gctcgtcaaa ggcagaaaca aaagcaagag aatttggctt atatcaaccg ttacattcac     420
catcatcatc gagctcaatt aattaacgcc cccccgaccg atgtcagcct ggggggacgag     480 ctccacttag acggcgagga cgtggcgatg gcgcatgccg acgcgctaga cgatttcgat     540
ctggacatgt tggggggacgg ggattccccg ggtccgggat ttaccccca cgactccgcc     600 ccctacggcg ctctggatat ggccgacttc gagtttgagc agatgtttac cgatgccctt     660
ggaattgacg agtacggtgg gttaattaa                                       689

<210> SEQ ID NO 10
<211> LENGTH: 176
<212> TYPE: PRT
<213> ORGANISM: Artificial Sequence
<220> FEATURE:
<223> OTHER INFORMATION: Synthetic Construct, Chimera of GhCIR1 HD
      domain and VP16 activation domain

<400> SEQUENCE: 10

Met Glu Gly Gly Gly Gly Gly Gly Gly Asn Ser Arg Trp Asn
1               5                   10                  15

Pro Thr Lys Glu Gln Ile Ser Met Leu Glu Ser Leu Tyr Lys Gln Gly
            20                  25                  30

Ile Arg Thr Pro Ser Ala Asp Gln Ile Gln Gln Ile Thr Ser Arg Leu
        35                  40                  45

Lys Ala Tyr Gly Thr Ile Glu Gly Lys Asn Val Phe Tyr Trp Phe Gln
    50                  55                  60

Asn His Lys Ala Arg Gln Arg Gln Lys Gln Lys Gln Glu Asn Leu Ala
65                  70                  75                  80

Tyr Ile Asn Arg Tyr Ile His His His Arg Ala Gln Leu Ile Asn
                85                  90                  95
```

```
Ala Pro Pro Thr Asp Val Ser Leu Gly Asp Glu Leu His Leu Asp Gly
            100                 105                 110

Glu Asp Val Ala Met Ala His Ala Asp Ala Leu Asp Phe Asp Leu
        115                 120                 125

Asp Met Leu Gly Asp Gly Asp Ser Pro Gly Pro Gly Phe Thr Pro His
    130                 135                 140

Asp Ser Ala Pro Tyr Gly Ala Leu Asp Met Ala Asp Phe Glu Phe Glu
145                 150                 155                 160

Gln Met Phe Thr Asp Ala Leu Gly Ile Asp Glu Tyr Gly Gly Leu Ile
                165                 170                 175

<210> SEQ ID NO 11
<211> LENGTH: 1652
<212> TYPE: DNA
<213> ORGANISM: Artificial Sequence
<220> FEATURE:
<223> OTHER INFORMATION: Synthetic Construct, Chimera of GhCIR1 HD
      domain, VP16 activation domain, estrogen regulatory domain and
      putative nuclear localization signal

<400> SEQUENCE: 11
gcgcgccgga cactgacttg gactgaagga gtagaaaaat tcccatgcca atcgctatac      60
accctcctta ttttttttct ttttaaacca aactcccaaa accctactcc aataatcaat     120
caaaatccaa atcaaaccct catttctctt atctgcaaat ggaaggtggc ggcggcggcg     180
gtggtggagg gaattcacgg tggaacccga cgaaggagca ataagcatg cttgaaagct      240 tgtacaagca agggataaga accccaagtg ctgatcagat acagcaaata accagtaggc     300
tcaaagctta tggcaccatt gaaggcaaaa acgtgttcta ttggttccaa atcataaag      360 ctcgtcaaag gcagaaacaa agcaagaga atttggctta tatcaaccgt acattcacc      420 atcatcatcg agctcaatta attaacgccc cccgaccga tgtcagcctg ggggacgagc     480
tccacttaga cggcgaggac gtggcgatgg cgcatgccga cgcgctagac gatttcgatc     540
tggacatgtt gggggacggg gattccccgg gtccgggatt acccccccac gactccgccc     600
cctacggcgc tctggatatg gccgacttcg agtttgagca gatgtttacc gatgcccttg     660
gaattgacga gtacggtggg gatccgtctg ctggagacat gagagctgcc aacctttggc     720
caagcccgct catgatcaaa cgctctaaga gaacagcct ggccttgtcc ctgacggccg      780
accagatggt cagtgccttg ttggatgctg agccccccat actctattcc gagtatgatc     840
ctaccagacc cttcagtgaa gcttcgatga tgggcttact gaccaacctg gcagacaggg     900
agctggttca catgatcaac tgggcgaaga gggtgccagg cttttgtgga ttgacccctc     960
atgatcaggt ccaccttcta gaatgtgcct ggctagagat cctgatgatt ggtctcgtct    1020
ggcgctccat ggagcaccca gtgaagctac tgtttgctcc taacttgctc ttggacagga    1080
accagggaaa atgtgtagag ggcatggtgg agatcttcga catgctgctg gctacatcat    1140
ctcggttccg catgatgaat ctgcaggag aggagtttgt gtgcctcaaa tctattattt     1200
tgcttaattc tggagtgtac acatttctgt ccagcaccct gaagtctctg aagagaagg     1260 accatatcca ccgagtcctg acaagatca cagacacttt gatccacctg atggccaagg    1320
caggcctgac cctgcagcag cagcaccagc ggctggccca gctcctcctc atcctctccc    1380
acatcaggca catgagtaac aaaggcatgg agcatctgta cagcatgaag tgcaagaacg    1440 tggtgccct ctatgacctg ctgctggaga tgctggacgc ccaccgccta catgcgccca     1500
ctagccgtgg aggggcatcc gtggaggaga cggaccaaag ccacttggcc actgcgggct    1560
```

```
ctacttcatc gcattccttg caaaagtatt acatcacggg ggaggcagag ggtttccctg    1620
ccacagtctg agagctccac tagttttttt tg                                 1652
```

<210> SEQ ID NO 12
<211> LENGTH: 490
<212> TYPE: PRT
<213> ORGANISM: Artificial Sequence
<220> FEATURE:
<223> OTHER INFORMATION: Synthetic Construct, Chimera of GhCIR1 HD
      domain, VP16 activation domain, estrogen regulatory domain and
      putative nuclear localization signal

<400> SEQUENCE: 12

```
Met Glu Gly Gly Gly Gly Gly Gly Gly Asn Ser Arg Trp Asn
1               5                   10                  15

Pro Thr Lys Glu Gln Ile Ser Met Leu Glu Ser Leu Tyr Lys Gln Gly
            20                  25                  30

Ile Arg Thr Pro Ser Ala Asp Gln Ile Gln Gln Ile Thr Ser Arg Leu
        35                  40                  45

Lys Ala Tyr Gly Thr Ile Glu Gly Lys Asn Val Phe Tyr Trp Phe Gln
    50                  55                  60

Asn His Lys Ala Arg Gln Arg Gln Lys Gln Lys Gln Glu Asn Leu Ala
65                  70                  75                  80

Tyr Ile Asn Arg Tyr Ile His His His Arg Ala Gln Leu Ile Asn
                85                  90                  95

Ala Pro Pro Thr Asp Val Ser Leu Gly Asp Glu Leu His Leu Asp Gly
            100                 105                 110

Glu Asp Val Ala Met Ala His Ala Asp Ala Leu Asp Asp Phe Asp Leu
        115                 120                 125

Asp Met Leu Gly Asp Gly Asp Ser Pro Gly Pro Gly Phe Thr Pro His
    130                 135                 140

Asp Ser Ala Pro Tyr Gly Ala Leu Asp Met Ala Asp Phe Glu Phe Glu
145                 150                 155                 160

Gln Met Phe Thr Asp Ala Leu Gly Ile Asp Glu Tyr Gly Gly Asp Pro
                165                 170                 175

Ser Ala Gly Asp Met Arg Ala Ala Asn Leu Trp Pro Ser Pro Leu Met
            180                 185                 190

Ile Lys Arg Ser Lys Lys Asn Ser Leu Ala Leu Ser Leu Thr Ala Asp
        195                 200                 205

Gln Met Val Ser Ala Leu Leu Asp Ala Glu Pro Pro Ile Leu Tyr Ser
    210                 215                 220

Glu Tyr Asp Pro Thr Arg Pro Phe Ser Glu Ala Ser Met Met Gly Leu
225                 230                 235                 240

Leu Thr Asn Leu Ala Asp Arg Glu Leu Val His Met Ile Asn Trp Ala
                245                 250                 255

Lys Arg Val Pro Gly Phe Val Asp Leu Thr Leu His Asp Gln Val His
            260                 265                 270

Leu Leu Glu Cys Ala Trp Leu Glu Ile Leu Met Ile Gly Leu Val Trp
        275                 280                 285

Arg Ser Met Glu His Pro Val Lys Leu Leu Phe Ala Pro Asn Leu Leu
    290                 295                 300

Leu Asp Arg Asn Gln Gly Lys Cys Val Glu Gly Met Val Glu Ile Phe
305                 310                 315                 320

Asp Met Leu Leu Ala Thr Ser Ser Arg Phe Arg Met Met Asn Leu Gln
                325                 330                 335
```

```
Gly Glu Glu Phe Val Cys Leu Lys Ser Ile Ile Leu Leu Asn Ser Gly
            340                 345                 350

Val Tyr Thr Phe Leu Ser Ser Thr Leu Lys Ser Leu Glu Glu Lys Asp
            355                 360                 365

His Ile His Arg Val Leu Asp Lys Ile Thr Thr Leu Ile His Leu
    370                 375                 380

Met Ala Lys Ala Gly Leu Thr Leu Gln Gln Gln His Gln Arg Leu Ala
385                 390                 395                 400

Gln Leu Leu Leu Ile Leu Ser His Ile Arg His Met Ser Asn Lys Gly
                    405                 410                 415

Met Glu His Leu Tyr Ser Met Lys Cys Lys Asn Val Val Pro Leu Tyr
                420                 425                 430

Asp Leu Leu Leu Glu Met Leu Asp Ala His Arg Leu His Ala Pro Thr
                435                 440                 445

Ser Arg Gly Gly Ala Ser Val Glu Glu Thr Asp Gln Ser His Leu Ala
    450                 455                 460

Thr Ala Gly Ser Thr Ser Ser His Ser Leu Gln Lys Tyr Tyr Ile Thr
465                 470                 475                 480

Gly Glu Ala Glu Gly Phe Pro Ala Thr Val
                485                 490
```

<210> SEQ ID NO 13
<211> LENGTH: 839
<212> TYPE: DNA
<213> ORGANISM: Artificial Sequence
<220> FEATURE:
<223> OTHER INFORMATION: Synthetic Construct, Chimera of HD-domain of
      GhCIR1 and the C-terminal domain of AtCIR2

<400> SEQUENCE: 13

```
ttttggcgcg ccggacactg acttggactg aaggagtaga aaaattccca tgccaatcgc    60
tatacaccct ccttattttt tttcttttta aaccaaactc ccaaaaccct actccaataa   120
tcaatcaaaa tccaaatcaa accctcattt tctttatctg caaatggaag gtggcggcgg   180
cggcggtggt ggagggaatt cacggtggaa cccgacgaag gagcaaataa gcatgcttga   240
aagcttgtac aagcaaggga taagaacccc aagtgctgat cagatacagc aaataaccag   300
taggctcaaa gcttatggca ccattgaagg caaaaacgtg ttctattggt ccaaaatca    360
taaagctcgt caaaggcaga aacaaaagca agagaatttg gcttatatca accgttacat   420
tcaccatcat catcgagctc aattaattaa tccatcaact agagatgttt ttgaaataag   480
cgaagaagat tgtcaagagg aagagaaggt gatagagaca ttacaactct ttccggtgaa   540
ttcatttgaa gactccaact ccaaggtgga caaaatgaga gctagaggca ataaccagta   600
ccgtgaatat attcgagaga ccaccacgac gtcgttttct ccatactcat catgtggagc   660
tgaaatggaa catccaccgc cattagatct tcgattaagc tttctttaag tcattgacca   720
caataacaaa agaaaaaaaa cagatgcttt agcctttaaa atgttgttgt attttgaatt   780
atgacatatt atccgatgca tggtttatga gatattttcc aatgcatggt taattaatt    839
```

<210> SEQ ID NO 14
<211> LENGTH: 181
<212> TYPE: PRT
<213> ORGANISM: Artificial Sequence
<220> FEATURE:
<223> OTHER INFORMATION: Synthetic Construct, Chimera of HD-domain of
      GhCIR1 and the C-terminal domain of AtCIR2

<400> SEQUENCE: 14

```
Met Glu Gly Gly Gly Gly Gly Gly Gly Asn Ser Arg Trp Asn
1               5                   10                  15

Pro Thr Lys Glu Gln Ile Ser Met Leu Glu Ser Leu Tyr Lys Gln Gly
            20                  25                  30

Ile Arg Thr Pro Ser Ala Asp Gln Ile Gln Gln Ile Thr Ser Arg Leu
        35                  40                  45

Lys Ala Tyr Gly Thr Ile Glu Gly Lys Asn Val Phe Tyr Trp Phe Gln
    50                  55                  60

Asn His Lys Ala Arg Gln Arg Gln Lys Gln Lys Gln Glu Asn Leu Ala
65                  70                  75                  80

Tyr Ile Asn Arg Tyr Ile His His His Arg Ala Gln Leu Ile Asn
                85                  90                  95

Pro Ser Thr Arg Asp Val Phe Glu Ile Ser Glu Asp Cys Gln Glu
            100                 105                 110

Glu Glu Lys Val Ile Glu Thr Leu Gln Leu Phe Pro Val Asn Ser Phe
            115                 120                 125

Glu Asp Ser Asn Ser Lys Val Asp Lys Met Arg Ala Arg Gly Asn Asn
130                 135                 140

Gln Tyr Arg Glu Tyr Ile Arg Glu Thr Thr Thr Thr Ser Phe Ser Pro
145                 150                 155                 160

Tyr Ser Ser Cys Gly Ala Glu Met Glu His Pro Pro Leu Asp Leu
                165                 170                 175

Arg Leu Ser Phe Leu
            180
```

<210> SEQ ID NO 15
<211> LENGTH: 1001
<212> TYPE: DNA
<213> ORGANISM: Artificial Sequence
<220> FEATURE:
<223> OTHER INFORMATION: Synthetic Construct, Chimera of HD-domain of
      GhCIR1 and the C-terminal domain of AtCIR2

<400> SEQUENCE: 15

```
ttttggcgcg ccggacactg acttggactg aaggagtaga aaaattccca tgccaatcgc      60
tatacaccct ccttattttt tttcttttta aaccaaactc ccaaaaccct actccaataa     120
tcaatcaaaa tccaaatcaa accctcattt tctttatctg caaatggaag gtggcggcgg     180
cggcggtggt ggagggaatt cacggtggaa cccgacgaag gagcaaataa gcatgcttga     240
aagcttgtac aagcaaggga taagaacccc aagtgctgat cagatacagc aaataaccag     300
taggctcaaa gcttatggca ccattgaagg caaaaacgtg ttctattggt tccaaaatca     360
taaagctcgt caaaggcaga acaaaagca agagaatttg gcttatatca accgttacat     420
tcaccatcat catcgagctc aacctgtttt tcatcctcct ccttgcacca atgttgtttg     480
tgctggtcca tattttgtac cacaagctga tcatcaccat catctaggct tttacccctca     540
gtgtcccaag gttcttctcc ctagtagatc aattaaaaga gaggcaggc ctattggtaa     600
aactttaatt aatccatcaa ctagagatgt ttttgaaata agcgaagaag attgtcaaga     660
ggaagagaag gtgatagaga cattacaact cttttccggtg aattcatttg aagactccaa     720
ctccaaggtg gacaaaatga gagctagagg caataaccag taccgtgaat atattcgaga     780
gaccaccacg acgtcgtttt ctccatactc atcatgtgga gctgaaatgg aacatccacc     840
gccattagat cttcgattaa gctttcttta agtcattgac cacaataaca aagaaaaaaa     900
```

```
aacagatgct ttagccttta aaatgttgtt gtattttgaa ttatgacata ttatccgatg        960
catggtttat gagatatttt ccaatgcatg gttaattaat t                           1001
```

<210> SEQ ID NO 16
<211> LENGTH: 235
<212> TYPE: PRT
<213> ORGANISM: Artificial Sequence
<220> FEATURE:
<223> OTHER INFORMATION: Chimera of HD-domain of GhCIR1 and the C-
      terminal domain of AtCIR2

<400> SEQUENCE: 16

```
Met Glu Gly Gly Gly Gly Gly Gly Gly Asn Ser Arg Trp Asn
1               5                   10                  15

Pro Thr Lys Glu Gln Ile Ser Met Leu Glu Ser Leu Tyr Lys Gln Gly
                20                  25                  30

Ile Arg Thr Pro Ser Ala Asp Gln Ile Gln Gln Ile Thr Ser Arg Leu
            35                  40                  45

Lys Ala Tyr Gly Thr Ile Glu Gly Lys Asn Val Phe Tyr Trp Phe Gln
        50                  55                  60

Asn His Lys Ala Arg Gln Arg Gln Lys Gln Glu Asn Leu Ala
65                  70                  75                  80

Tyr Ile Asn Arg Tyr Ile His His His Arg Ala Gln Pro Val Phe
                85                  90                  95

His Pro Pro Pro Cys Thr Asn Val Val Cys Ala Gly Pro Tyr Phe Val
            100                 105                 110

Pro Gln Ala Asp His His His Leu Gly Phe Tyr Pro Gln Cys Pro
        115                 120                 125

Lys Val Leu Leu Pro Ser Arg Ser Ile Lys Arg Arg Gly Arg Pro Ile
130                 135                 140

Gly Lys Thr Leu Ile Asn Pro Ser Thr Arg Asp Val Phe Glu Ile Ser
145                 150                 155                 160

Glu Glu Asp Cys Gln Glu Glu Lys Val Ile Glu Thr Leu Gln Leu
                165                 170                 175

Phe Pro Val Asn Ser Phe Glu Asp Ser Asn Ser Lys Val Asp Lys Met
            180                 185                 190

Arg Ala Arg Gly Asn Asn Gln Tyr Arg Glu Tyr Ile Arg Glu Thr Thr
        195                 200                 205

Thr Thr Ser Phe Ser Pro Tyr Ser Ser Cys Gly Ala Glu Met Glu His
    210                 215                 220

Pro Pro Pro Leu Asp Leu Arg Leu Ser Phe Leu
225                 230                 235
```

<210> SEQ ID NO 17
<211> LENGTH: 260
<212> TYPE: PRT
<213> ORGANISM: Arabidopsis thaliana

<400> SEQUENCE: 17

```
Met Glu Asn Glu Val Asn Ala Gly Thr Ala Ser Ser Ser Arg Trp Asn
1               5                   10                  15

Pro Thr Lys Asp Gln Ile Thr Leu Leu Glu Asn Leu Tyr Lys Glu Gly
                20                  25                  30

Ile Arg Thr Pro Ser Ala Asp Gln Ile Gln Gln Ile Thr Gly Arg Leu
            35                  40                  45

Arg Ala Tyr Gly His Ile Glu Gly Lys Asn Val Phe Tyr Trp Phe Gln
        50                  55                  60
```

Asn His Lys Ala Arg Gln Arg Gln Lys Gln Glu Arg Met Ala
65                  70                  75                  80

Tyr Phe Asn Arg Leu Leu His Lys Thr Ser Arg Phe Phe Tyr Pro Pro
                85                  90                  95

Pro Cys Ser Asn Val Gly Cys Val Ser Pro Tyr Tyr Leu Gln Gln Ala
            100                 105                 110

Ser Asp His His Met Asn Gln His Gly Ser Val Tyr Thr Asn Asp Leu
        115                 120                 125

Leu His Arg Asn Asn Val Met Ile Pro Ser Gly Gly Tyr Glu Lys Arg
    130                 135                 140

Thr Val Thr Gln His Gln Lys Gln Leu Ser Asp Ile Arg Thr Thr Ala
145                 150                 155                 160

Ala Thr Arg Met Pro Ile Ser Pro Ser Ser Leu Arg Phe Asp Arg Phe
                165                 170                 175

Ala Leu Arg Asp His Cys Tyr Ala Gly Glu Asp Ile Asn Val Asn Ser
            180                 185                 190

Ser Gly Arg Lys Thr Leu Pro Leu Phe Pro Leu Gln Pro Leu Asn Ala
        195                 200                 205

Ser Asn Ala Asp Gly Met Gly Ser Ser Ser Phe Ala Leu Gly Ser Asp
    210                 215                 220

Ser Pro Val Asp Cys Ser Ser Asp Gly Ala Gly Arg Glu Gln Pro Phe
225                 230                 235                 240

Ile Asp Phe Phe Ser Gly Gly Ser Thr Ser Thr Arg Phe Asp Ser Asn
                245                 250                 255

Gly Asn Gly Leu
            260

<210> SEQ ID NO 18
<211> LENGTH: 244
<212> TYPE: PRT
<213> ORGANISM: Arabidopsis thaliana

<400> SEQUENCE: 18

Met Ser Pro Val Ala Ser Thr Arg Trp Cys Pro Thr Pro Glu Gln Leu
1               5                   10                  15

Met Ile Leu Glu Glu Met Tyr Arg Ser Gly Ile Arg Thr Pro Asn Ala
                20                  25                  30

Val Gln Ile Gln Gln Ile Thr Ala His Leu Ala Phe Tyr Gly Arg Ile
            35                  40                  45

Glu Gly Lys Asn Val Phe Tyr Trp Phe Gln Asn His Lys Ala Arg Asp
        50                  55                  60

Arg Gln Lys Leu Arg Lys Lys Leu Ala Lys Gln Leu His Gln Gln Gln
65                  70                  75                  80

His Gln Leu Gln Leu Gln Leu Gln Gln Ile Lys Pro Lys Pro Ile Ser
                85                  90                  95

Ser Met Ile Ser Gln Pro Val Asn Lys Asn Ile Ile Asp His His Asn
            100                 105                 110

Pro Tyr His His His His His Asn His His Asn His His Arg Pro
        115                 120                 125

Tyr Asp His Met Ser Phe Asp Cys Cys Ser His Pro Pro Met Cys
    130                 135                 140

Leu Pro His Gln Gly Thr Gly Val Gly Glu Ala Pro Ser Lys Val Met
145                 150                 155                 160

Asn Glu Tyr Tyr Cys Thr Lys Ser Gly Ala Glu Glu Ile Leu Met Gln
                165                 170                 175

```
Lys Ser Ile Thr Gly Pro Asn Ser Ser Tyr Gly Arg Asp Trp Met Met
                180                 185                 190

Met Met Asp Met Gly Pro Arg Pro Ser Tyr Pro Ser Ser Ser Ser Ser
            195                 200                 205

Pro Ile Ser Cys Cys Asn Met Met Met Ser Ser Pro Lys Ile Pro Leu
    210                 215                 220

Lys Thr Leu Glu Leu Phe Pro Ile Ser Ser Ile Asn Ser Lys Gln Asp
225                 230                 235                 240

Ser Thr Lys Leu

<210> SEQ ID NO 19
<211> LENGTH: 292
<212> TYPE: PRT
<213> ORGANISM: Arabidopsis thaliana

<400> SEQUENCE: 19

Met Glu Pro Pro Gln His Gln His His His Gln Ala Asp Gln Glu
1               5                   10                  15

Ser Gly Asn Asn Asn Asn Lys Ser Gly Ser Gly Gly Tyr Thr Cys
            20                  25                  30

Arg Gln Thr Ser Thr Arg Trp Thr Pro Thr Thr Glu Gln Ile Lys Ile
            35                  40                  45

Leu Lys Glu Leu Tyr Tyr Asn Asn Ala Ile Arg Ser Pro Thr Ala Asp
    50                  55                  60

Gln Ile Gln Lys Ile Thr Ala Arg Leu Arg Gln Phe Gly Lys Ile Glu
65                  70                  75                  80

Gly Lys Asn Val Phe Tyr Trp Phe Gln Asn His Lys Ala Arg Glu Arg
                85                  90                  95

Gln Lys Lys Arg Phe Asn Gly Thr Asn Met Thr Thr Pro Ser Ser Ser
            100                 105                 110

Pro Asn Ser Val Met Met Ala Ala Asn Asp His Tyr His Pro Leu Leu
        115                 120                 125

His His His His Gly Val Pro Met Gln Arg Pro Ala Asn Ser Val Asn
130                 135                 140

Val Lys Leu Asn Gln Asp His His Leu Tyr His His Asn Lys Pro Tyr
145                 150                 155                 160

Pro Ser Phe Asn Asn Gly Asn Leu Asn His Ala Ser Ser Gly Thr Glu
                165                 170                 175

Cys Gly Val Val Asn Ala Ser Asn Gly Tyr Met Ser Ser His Val Tyr
            180                 185                 190

Gly Ser Met Glu Gln Asp Cys Ser Met Asn Tyr Asn Asn Val Gly Gly
        195                 200                 205

Gly Trp Ala Asn Met Asp His His Tyr Ser Ser Ala Pro Tyr Asn Phe
210                 215                 220

Phe Asp Arg Ala Lys Pro Leu Phe Gly Leu Glu Gly His Gln Glu Glu
225                 230                 235                 240

Glu Glu Cys Gly Gly Asp Ala Tyr Leu Glu His Arg Arg Thr Leu Pro
                245                 250                 255

Leu Phe Pro Met His Gly Glu Asp His Ile Asn Gly Gly Ser Gly Ala
            260                 265                 270

Ile Trp Lys Tyr Gly Gln Ser Glu Val Arg Pro Cys Ala Ser Leu Glu
        275                 280                 285

Leu Arg Leu Asn
        290
```

```
<210> SEQ ID NO 20
<211> LENGTH: 307
<212> TYPE: PRT
<213> ORGANISM: Petunia x hybrida

<400> SEQUENCE: 20

Met Glu Thr Ala Gln His Gln Gln Asn Asn Gln Gln His Tyr Leu His
1               5                   10                  15

Gln His Leu Ser Ile Gly Gln Gly Thr Asn Ile Glu Asp Gly Ser Asn
            20                  25                  30

Lys Asn Asn Ser Ser Asn Phe Met Cys Arg Gln Asn Ser Thr Arg Trp
        35                  40                  45

Thr Pro Thr Thr Asp Gln Ile Arg Ile Leu Lys Asp Leu Tyr Tyr Asn
    50                  55                  60

Asn Gly Val Arg Ser Pro Thr Ala Glu Gln Ile Gln Arg Ile Ser Ala
65                  70                  75                  80

Lys Leu Arg Gln Tyr Gly Lys Ile Glu Gly Lys Asn Val Phe Tyr Trp
                85                  90                  95

Phe Gln Asn His Lys Ala Arg Glu Arg Gln Lys Lys Arg Leu Ile Ala
            100                 105                 110

Ala Ala Thr Thr Asp Asn Thr Asn Leu Pro Met Gln Met Gln Phe Gln
        115                 120                 125

Arg Gly Val Trp Arg Ser Ser Ala Asp Asp Pro Ile His His Lys Tyr
    130                 135                 140

Thr Asn Pro Gly Val His Cys Pro Ser Ala Ser Ser His Gly Val Leu
145                 150                 155                 160

Ala Val Gly Gln Asn Gly Asn His Gly Tyr Gly Ala Leu Ala Met Glu
                165                 170                 175

Lys Ser Phe Arg Asp Cys Ser Ile Ser Pro Gly Ser Ser Met Ser His
            180                 185                 190

His His His Gln Asn Phe Ala Trp Ala Gly Val Asp Pro Tyr Ser Ser
        195                 200                 205

Thr Thr Thr Tyr Pro Phe Leu Glu Lys Thr Lys His Phe Glu Asn Glu
    210                 215                 220

Thr Leu Glu Ala Asp Glu Glu Gln Glu Glu Asp Gln Glu Asn Tyr
225                 230                 235                 240

Tyr Tyr Gln Arg Thr Thr Ser Ala Ile Glu Thr Leu Pro Leu Phe Pro
                245                 250                 255

Met His Glu Glu Asn Ile Ser Ser Phe Cys Asn Leu Lys His Gln Glu
            260                 265                 270

Ser Ser Gly Gly Phe Tyr Thr Glu Trp Tyr Arg Ala Asp Asp Asn Leu
        275                 280                 285

Ala Ala Ala Arg Ala Ser Leu Glu Leu Ser Leu Asn Ser Phe Ile Gly
    290                 295                 300

Asn Ser Ser
305

<210> SEQ ID NO 21
<211> LENGTH: 272
<212> TYPE: PRT
<213> ORGANISM: tomato

<400> SEQUENCE: 21

Met Glu His Gln His Asn Ile Glu Asp Gly Gly Lys Asn Ser Asn Asn
1               5                   10                  15

Ser Phe Leu Cys Arg Gln Ser Ser Ser Arg Trp Thr Pro Thr Ser Asp
            20                  25                  30
```

```
Gln Ile Arg Ile Leu Lys Asp Leu Tyr Tyr Asn Asn Gly Val Arg Ser
         35                  40                  45

Pro Thr Ala Glu Gln Ile Gln Arg Ile Ser Ala Lys Leu Arg Gln Tyr
 50                  55                  60

Gly Lys Ile Glu Gly Lys Asn Val Phe Tyr Trp Phe Gln Asn His Lys
 65                  70                  75                  80

Ala Arg Glu Arg Gln Lys Lys Arg Leu Ile Ala Ala Ser Ala Thr
                 85                  90                  95

Asp Asn Asn Asn Ile Ser Ser Met Gln Met Ile Pro His Leu Trp Arg
                 100                 105                 110

Ser Pro Asp Asp His His Lys Tyr Asn Thr Ala Thr Thr Asn Pro Gly
             115                 120                 125

Val Gln Cys Pro Ser Pro Ser Ser His Gly Val Leu Pro Val Val Gln
 130                 135                 140

Thr Gly Asn Tyr Gly Tyr Gly Thr Leu Ala Met Glu Lys Ser Phe Arg
 145                 150                 155                 160

Glu Cys Ser Ile Ser Pro Pro Gly Gly Ser Tyr His Gln Asn Leu Thr
                 165                 170                 175

Trp Val Gly Val Asp Pro Tyr Asn Asn Met Ser Thr Thr Ser Pro Ala
                 180                 185                 190

Thr Tyr Pro Phe Leu Glu Lys Ser Asn Asn Lys His Tyr Glu Glu Thr
             195                 200                 205

Leu Asp Glu Glu Gln Glu Glu Asn Tyr Gln Arg Gly Asn Ser Ala
 210                 215                 220

Leu Glu Thr Leu Ser Leu Phe Pro Met His Glu Asn Ile Ile Ser
225                 230                 235                 240

Asn Phe Cys Ile Lys His His Glu Ser Ser Gly Gly Trp Tyr His Ser
                 245                 250                 255

Asp Asn Asn Asn Leu Ala Ala Leu Glu Leu Thr Leu Asn Ser Phe Pro
                 260                 265                 270

<210> SEQ ID NO 22
<211> LENGTH: 200
<212> TYPE: PRT
<213> ORGANISM: rice

<400> SEQUENCE: 22

Met Glu Ala Leu Ser Gly Arg Val Gly Val Lys Cys Gly Arg Trp Asn
 1               5                  10                  15

Pro Thr Ala Glu Gln Val Lys Val Leu Thr Glu Leu Phe Arg Ala Gly
                 20                  25                  30

Leu Arg Thr Pro Ser Thr Glu Gln Ile Gln Arg Ile Ser Thr His Leu
             35                  40                  45

Ser Ala Phe Gly Lys Val Glu Ser Lys Asn Val Phe Tyr Trp Phe Gln
 50                  55                  60

Asn His Lys Ala Arg Glu Arg His His Lys Lys Arg Arg Arg Gly
 65                  70                  75                  80

Ala Ser Ser Pro Asp Ser Gly Ser Asn Asp Asp Gly Arg Ala Ala
                 85                  90                  95

Ala His Glu Gly Asp Ala Asp Leu Val Leu Gln Pro Pro Glu Ser Lys
             100                 105                 110

Arg Glu Ala Arg Ser Tyr Gly His His His Arg Leu Met Thr Cys Tyr
             115                 120                 125

Val Arg Asp Val Val Glu Thr Glu Ala Met Trp Glu Arg Pro Thr Arg
 130                 135                 140
```

```
Glu Val Glu Thr Leu Glu Leu Phe Pro Leu Lys Ser Tyr Asp Leu Glu
145                 150                 155                 160

Val Asp Lys Val Arg Tyr Val Arg Gly Gly Gly Glu Gln Cys Arg
            165                 170                 175

Glu Ile Ser Phe Phe Asp Val Ala Ala Gly Arg Asp Pro Leu Glu
            180                 185                 190

Leu Arg Leu Cys Ser Phe Gly Leu
        195                 200

<210> SEQ ID NO 23
<211> LENGTH: 220
<212> TYPE: PRT
<213> ORGANISM: Zea mays

<400> SEQUENCE: 23

Met Glu Ala Leu Ser Gly Arg Val Gly Val Lys Cys Gly Arg Trp Asn
1               5                   10                  15

Pro Thr Ala Glu Gln Val Lys Val Leu Thr Glu Leu Phe Arg Ala Gly
            20                  25                  30

Leu Arg Thr Pro Ser Thr Glu Gln Ile Gln Arg Ile Ser Thr His Leu
        35                  40                  45

Ser Ala Phe Gly Lys Val Glu Ser Lys Asn Val Phe Tyr Trp Phe Gln
    50                  55                  60

Asn His Lys Ala Arg Glu Arg His His Lys Lys Arg Arg Arg Gly
65                  70                  75                  80

Ala Ser Ser Ser Pro Asp Ser Gly Ser Gly Arg Gly Ser Asn Asn
            85                  90                  95

Glu Glu Asp Gly Arg Gly Ala Ala Ser Gln Ser His Asp Ala Asp Ala
            100                 105                 110

Asp Ala Asp Leu Val Leu Gln Pro Pro Glu Ser Lys Arg Glu Ala Arg
        115                 120                 125

Ser Tyr Gly His His His Arg Leu Val Thr Cys Tyr Val Arg Asp Val
    130                 135                 140

Val Glu Gln Gln Glu Ala Ser Pro Ser Trp Glu Arg Pro Thr Arg Glu
145                 150                 155                 160

Val Glu Thr Leu Glu Leu Phe Pro Leu Lys Ser Tyr Gly Asp Leu Glu
            165                 170                 175

Ala Ala Glu Lys Val Arg Ser Tyr Val Arg Gly Ile Ala Ala Thr Ser
            180                 185                 190

Glu Gln Cys Arg Glu Leu Ser Phe Phe Asp Val Ser Ala Gly Arg Asp
        195                 200                 205

Pro Pro Leu Glu Leu Arg Leu Cys Ser Phe Gly Pro
210                 215                 220

<210> SEQ ID NO 24
<211> LENGTH: 240
<212> TYPE: PRT
<213> ORGANISM: Zea mays

<400> SEQUENCE: 24

Met Ala Ala Asn Ala Gly Gly Gly Ala Gly Gly Ser Gly Ser
1               5                   10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
        35                  40                  45
```

```
Cys Gly Ile Arg Ser Pro Ser Ser Glu Gln Ile Gln Arg Ile Thr Ala
 50                  55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                 85                  90                  95

Leu Asp Val Asn Val Pro Ala Ala Gly Ala Ala Asp Ala Thr Thr Ser
                100                 105                 110

Gln Leu Gly Val Leu Ser Leu Ser Ser Pro Pro Ser Gly Ala Ala
            115                 120                 125

Pro Pro Ser Pro Thr Leu Gly Leu Tyr Ala Ala Gly Asn Gly Gly Gly
            130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Val Gly Ala Val Val Arg
                165                 170                 175

Ser Phe Leu Gly His Cys Ala Gln Phe His Val Arg Thr Tyr Glu Leu
                180                 185                 190

Ile Ala Ala Ser Phe His Pro Pro Val Tyr Ile Thr Val Arg Tyr Gly
            195                 200                 205

Gly Ala Arg Pro Gln Asp Tyr Met Gly Val Thr Asp Thr Gly Ser Ser
            210                 215                 220

Ser Gln Trp Pro Arg Phe Ser Ser Ser Asp Thr Ile Met Ala Ala Ala
225                 230                 235                 240

<210> SEQ ID NO 25
<211> LENGTH: 237
<212> TYPE: PRT
<213> ORGANISM: Zea mays

<400> SEQUENCE: 25

Met Ala Ala Asn Ala Gly Gly Gly Ala Gly Gly Gly Ser Gly Ser
 1               5                  10                  15

Gly Ser Val Ala Ala Pro Ala Val Cys Arg Pro Ser Gly Ser Arg Trp
            20                  25                  30

Thr Pro Thr Pro Glu Gln Ile Arg Met Leu Lys Glu Leu Tyr Tyr Gly
            35                  40                  45

Cys Gly Ile Arg Ser Pro Ser Ser Glu Gln Ile Gln Arg Ile Thr Ala
 50                  55                  60

Met Leu Arg Gln His Gly Lys Ile Glu Gly Lys Asn Val Phe Tyr Trp
 65                  70                  75                  80

Phe Gln Asn His Lys Ala Arg Glu Arg Gln Lys Arg Arg Leu Thr Ser
                 85                  90                  95

Leu Asp Val Asn Val Pro Ala Ala Gly Ala Ala Asp Ala Thr Thr Ser
                100                 105                 110

Gln Leu Gly Val Leu Ser Leu Ser Ser Pro Pro Ser Gly Ala Ala
            115                 120                 125

Pro Pro Ser Pro Thr Leu Gly Phe Tyr Ala Ala Gly Asn Gly Gly Gly
            130                 135                 140

Ser Ala Val Leu Leu Asp Thr Ser Ser Asp Trp Gly Ser Ser Gly Ala
145                 150                 155                 160

Ala Met Ala Thr Glu Thr Cys Phe Leu Gln Val Gly Ala Val Val Arg
                165                 170                 175

Ser Phe Leu Gly His Cys Ala Gln Phe His Val Arg Thr Tyr Glu Leu
                180                 185                 190
```

```
Ile Ala Ala Ser Phe His Pro Pro Val Tyr Ile Thr Val Arg Tyr Gly
            195                 200                 205

Gly Ala Arg Pro Gln Asp Tyr Met Gly Val Thr Asp Thr Gly Ser Ser
    210                 215                 220

Ser Gln Trp Pro Arg Phe Ala Ser Ser Asp Thr Ile Met
225                 230                 235
```

<210> SEQ ID NO 26
<211> LENGTH: 253
<212> TYPE: PRT
<213> ORGANISM: Zea mays

<400> SEQUENCE: 26

```
Met Glu Gly Gly Leu Ser Pro Glu Arg His Ala Ala Ala Glu Pro Val
1               5                   10                  15

Arg Ser Arg Trp Thr Pro Lys Pro Glu Gln Ile Leu Ile Leu Glu Ser
            20                  25                  30

Ile Phe Asn Ser Gly Met Val Asn Pro Pro Lys Asp Glu Thr Val Arg
            35                  40                  45

Ile Arg Lys Leu Leu Glu Arg Phe Gly Ala Val Gly Asp Ala Asn Val
50                  55                  60

Phe Tyr Trp Phe Gln Asn Arg Arg Ser Arg Ser Arg Arg Gln Arg
65                  70                  75                  80

Gln Leu Gln Ala Gln Ala Ala Ser Ser Ser Ser Gly Ser Pro
            85                  90                  95

Pro Thr Ser Gly Leu Ala Pro Gly His Ala Thr Ala Ser Ser Thr Ala
            100                 105                 110

Gly Met Phe Ala His Gly Ala Thr Tyr Gly Ser Ser Ala Ser Ala Ser
            115                 120                 125

Trp Pro Pro Pro Ser Cys Glu Gly Met Met Gly Asp Leu Asp Tyr
            130                 135                 140

Gly Gly Gly Asp Asp Leu Phe Ala Ile Ser Arg Gln Met Gly Tyr Ala
145                 150                 155                 160

Ser Gly Gly Gly Ser Gly Ser Ala Ser Ser Ala Ala Val Ala His His
            165                 170                 175

Glu Gln Gln Gln Gln Leu Tyr Tyr Ser Pro Cys Gln Pro Ala Ser Met
            180                 185                 190

Thr Val Phe Ile Asn Gly Val Ala Thr Glu Val Pro Arg Gly Pro Ile
            195                 200                 205

Asp Leu Arg Ser Met Phe Gly Gln Asp Val Met Leu Val His Ser Thr
            210                 215                 220

Ala Gly Leu Leu Pro Val Asn Glu Tyr Gly Val Leu Thr Gln Ser Leu
225                 230                 235                 240

Gln Met Gly Glu Ser Tyr Phe Leu Val Thr Arg Gly Tyr
            245                 250
```

<210> SEQ ID NO 27
<211> LENGTH: 227
<212> TYPE: PRT
<213> ORGANISM: Zea mays

<400> SEQUENCE: 27

```
Met Ala Ser Ala Asp Ala Trp Ala Thr Lys Glu Gln Val Ala Val Leu
1               5                   10                  15

Glu Gly Leu Tyr Glu His Gly Leu Arg Thr Pro Ser Ala Glu Gln Ile
            20                  25                  30
```

```
Gln Gln Ile Thr Gly Arg Leu Arg Glu His Gly Ala Ile Glu Gly Lys
            35                  40                  45

Asn Val Phe Tyr Trp Phe Gln Asn His Lys Ala Arg Gln Arg Gln Arg
 50                  55                  60

Gln Lys Gln Asp Ser Phe Ala Tyr Phe Ser Arg Leu Leu Arg Arg Pro
 65                  70                  75                  80

Pro Pro Leu Pro Val Leu Ser Met Pro Ala Pro Pro Tyr His His
                85                  90                  95

Ala Arg Val Pro Ala Pro Ala Ile Pro Met Pro Met Ala Pro Pro
                100                 105                 110

Pro Pro Ala Ala Cys Asn Asp Asn Gly Gly Ala Arg Val Ile Tyr Arg
                115                 120                 125

Asn Pro Phe Tyr Val Ala Ala Pro Gln Ala Pro Pro Ala Asn Ala Ala
 130                 135                 140

Tyr Tyr Tyr Pro Gln Pro Gln Gln Gln Gln Gln Gln Val Thr Val
145                 150                 155                 160

Met Tyr Gln Tyr Pro Arg Met Glu Val Ala Gly Gln Asp Lys Met Met
                165                 170                 175

Thr Arg Ala Ala Ala His Gln Gln Gln Gln His Asn Gly Ala Gly Gln
                180                 185                 190

Gln Pro Gly Arg Ala Gly His Pro Ser Arg Glu Thr Leu Gln Leu Phe
                195                 200                 205

Pro Pro Pro Ala His Leu Arg Ala Ala Ala Arg Gln Gly Ala Arg Arg
                210                 215                 220

Gln Arg Gln
225

<210> SEQ ID NO 28
<211> LENGTH: 134
<212> TYPE: PRT
<213> ORGANISM: Zea mays

<400> SEQUENCE: 28

Met Glu Ser Ser His Ser Thr Ala Glu Asp Glu Ser Gly Trp Lys Gly
 1               5                   10                  15

Ser Ser Gly Ala His Ser Ser Val Ser Arg Trp Ser Pro Thr Lys Glu
                20                  25                  30

Gln Ile Asp Met Leu Glu Asn Phe Tyr Lys Gln Gly Ile Arg Thr Pro
            35                  40                  45

Ser Thr Glu Gln Ile Gln Gln Ile Thr Ser Arg Leu Arg Ala Tyr Gly
 50                  55                  60

Tyr Ile Glu Gly Lys Asn Val Phe Tyr Trp Phe Gln Asn His Lys Ala
 65                  70                  75                  80

Arg Gln Arg Gln Lys Leu Lys Gln Lys Gln Ser Ile Ala Tyr Cys
                85                  90                  95

Asn Cys Phe Leu His Ala Ser His Pro Ile Cys Gln Asn Val Val Cys
                100                 105                 110

Val His Ile Val Cys Lys Arg Val Asp Ser Ala Phe Ile Leu Thr Asn
                115                 120                 125

Gln Arg Cys Leu Gln Val
130

<210> SEQ ID NO 29
<211> LENGTH: 225
<212> TYPE: PRT
<213> ORGANISM: Zea mays
```

```
<400> SEQUENCE: 29

Met Glu Ser His Ser Thr Ala Glu Asp Glu Ser Gly Trp Lys Gly Ser
1               5                   10                  15

Ser Gly Ala His Ser Ser Val Ser Arg Trp Ser Pro Thr Lys Glu Gln
                20                  25                  30

Ile Asp Met Glu Thr Leu Glu Asn Phe Tyr Lys Gln Gly Ile Arg Thr
            35                  40                  45

Pro Ser Thr Glu Gln Ile Gln Gln Ile Thr Ser Arg Leu Arg Ala Tyr
    50                  55                  60

Gly Tyr Ile Glu Gly Lys Asn Val Phe Tyr Trp Phe Gln Asn His Lys
65                  70                  75                  80

Ala Arg Gln Arg Gln Lys Leu Lys Gln Lys Gln Ser Ile Ala Tyr
                85                  90                  95

Cys Asn Cys Phe Leu His Ala Ser His Pro Ile Cys Gln Asn Val Val
                100                 105                 110

Cys Ala Pro Tyr Cys Leu Gln Lys Ser Gly Phe Ser Phe Tyr Pro His
            115                 120                 125

Gln Pro Lys Val Leu Ala Ser Val Gly Ile Ser Ser Arg Ile Glu Thr
    130                 135                 140

Gly Ser Phe Gly Met Glu Thr Leu Arg Ile Cys Asp Gly Met Glu Thr
145                 150                 155                 160

Gln Ser Glu His Pro Asp Tyr Asn Tyr Ser Thr Ser Asn Arg Glu Ala
                165                 170                 175

Leu Thr Leu Phe Pro Leu His Pro Thr Gly Ile Leu Glu Glu Lys Thr
            180                 185                 190

Thr His His Ser Val Asp Val Thr Asp Lys Ser Phe Val Ser Ile Ala
            195                 200                 205

Val Asp Glu Asn Gly His Leu Gly Asn Gln Pro Cys Phe Asn Phe Gln
    210                 215                 220

Tyr
225

<210> SEQ ID NO 30
<211> LENGTH: 212
<212> TYPE: PRT
<213> ORGANISM: Glycine max

<400> SEQUENCE: 30

Met Glu Ser His Ser Ser Asp Ala Glu Ala Glu Asn Val Arg Thr His
1               5                   10                  15

Ser Ser Val Ser Arg Trp Ser Pro Thr Lys Glu Gln Ile Asp Met Leu
                20                  25                  30

Glu Asn Leu Tyr Lys Gln Gly Ile Arg Thr Pro Ser Thr Glu Gln Ile
            35                  40                  45

Gln Gln Ile Thr Ser Arg Leu Arg Ala Tyr Gly His Ile Glu Gly Lys
    50                  55                  60

Asn Val Phe Tyr Trp Phe Gln Asn His Lys Ala Arg Gln Arg Gln Lys
65                  70                  75                  80

Leu Met Lys Gln Gln Thr Ile Ala Tyr Ser Asn Arg Phe Leu Arg Ala
                85                  90                  95

Ser His Pro Ile Cys Gln Asn Val Ala Cys Ala Pro Tyr Cys Leu Gln
            100                 105                 110
```

-continued

```
Arg Ser Gly Phe Ser Phe Tyr Pro Gln Gln Ser Lys Val Leu Ala Ser
            115                 120                 125

Gly Gly Ile Ser Ser Thr Gly Pro Leu Gly Met Gln Arg Met Phe Asp
130                 135                 140

Gly Met Gln Ser Ser Glu His Pro Asp Cys Asn Arg Glu Val Leu Thr
145                 150                 155                 160

Leu Phe Pro Leu His Pro Thr Gly Ile Leu Lys Glu Lys Thr Thr His
                165                 170                 175

Gln Val Pro Ser Leu Ala Ser Thr Ser Val Val Ala Val Asp Glu Asp
            180                 185                 190

Gly His Leu Gly Asn Gln Pro Phe Phe Asn Phe Phe Thr Thr Glu Pro
        195                 200                 205

Arg Ser Arg Glu
    210
```

<210> SEQ ID NO 31
<211> LENGTH: 236
<212> TYPE: PRT
<213> ORGANISM: Glycine max
<220> FEATURE:
<221> NAME/KEY: MISC_FEATURE
<222> LOCATION: (162)..(162)
<223> OTHER INFORMATION: Xaa can be any naturally occurring amino acid

<400> SEQUENCE: 31

```
Met Leu Lys Leu Ser Met Lys Val His Gln Phe Ala Arg Gly Phe Trp
1               5                   10                  15

Glu His Glu Pro Ser Leu Thr Leu Gly Cys Lys Arg Leu Arg Pro Leu
            20                  25                  30

Ala Pro Lys Leu Ser Asn Thr Asp Thr Ile Ser Pro His His Pro
        35                  40                  45

Val Thr Thr Phe Asp Leu Lys Ser Phe Ile Lys Pro Glu Ser Ala Ser
50                  55                  60

Arg Lys Leu Gly Ile Gly Ser Ser Asp Asp Asn Thr Asn Lys Arg Asp
65                  70                  75                  80

Pro Ser Ser Pro Gln Gly Gln Ala Glu Thr His Ile Pro Gly Gly Thr
                85                  90                  95

Arg Trp Asn Pro Thr Gln Glu Gln Ile Gly Ile Leu Glu Met Leu Tyr
            100                 105                 110

Arg Gly Gly Met Arg Thr Pro Asn Ala Gln Gln Ile Glu Gln Ile Thr
        115                 120                 125

Ala Gln Leu Ser Lys Tyr Gly Lys Ile Glu Gly Lys Asn Val Phe Tyr
    130                 135                 140

Trp Phe Gln Asn His Lys Ala Arg Glu Arg Gln Lys Gln Lys Arg Asn
145                 150                 155                 160

Asn Xaa Gly Leu Ala His Ser Pro Arg Thr Thr Leu Thr Thr Ser Pro
                165                 170                 175

Pro Phe Ser Cys Cys Val Ile Thr Thr Met Asp Thr Thr Lys Arg Gly
            180                 185                 190

Glu Val Val Glu Arg Glu Glu Asp Ser Pro Leu Lys Lys Cys Arg
        195                 200                 205

Ser Trp Ala Phe Glu Tyr Leu Glu Asp Gln Arg Glu Glu His Arg
    210                 215                 220

Thr Leu Glu Leu Phe Pro Leu His Pro Glu Gly Arg
225                 230                 235
```

```
<210> SEQ ID NO 32
<211> LENGTH: 222
<212> TYPE: PRT
<213> ORGANISM: Glycine max

<400> SEQUENCE: 32

Met Met Lys Val His Gln Phe Thr Arg Gly Leu Ile Trp Glu His Glu
1               5                   10                  15

Pro Phe Leu Thr Leu Gly Cys Lys Arg Leu Arg Pro Leu Ala Pro Lys
            20                  25                  30

Leu Pro Asn Thr Lys Thr Ile Thr Thr Pro Phe Asp Leu Lys Ser Phe
        35                  40                  45

Ile Arg Pro Glu Ser Gly Pro Arg Lys Pro Val Ser Ser Asp Asp Thr
    50                  55                  60

Lys Lys Asp Pro Pro Ser Pro Gln Gly Gln Ile Glu Thr His Pro Gly
65                  70                  75                  80

Gly Thr Arg Trp Asn Pro Thr Gln Glu Gln Ile Gly Ile Leu Glu Met
                85                  90                  95

Leu Tyr Lys Gly Gly Met Arg Thr Pro Asn Ala Gln Gln Ile Glu Gln
            100                 105                 110

Ile Thr Val Gln Leu Gly Lys Tyr Gly Lys Ile Glu Gly Lys Asn Val
        115                 120                 125

Phe Tyr Trp Phe Gln Asn His Lys Ala Arg Glu Arg Gln Lys Gln Lys
    130                 135                 140

Arg Ser Ser Leu Ala Ser Ser His Ser Pro Arg Thr Pro Thr Ile His
145                 150                 155                 160

Ser Val Val Thr Leu Glu Thr Thr Arg Gly Glu Val Val Glu Arg Asp
                165                 170                 175

His Glu Glu Asp Ser Pro Tyr Lys Lys Lys Cys Arg Arg Trp Val Phe
            180                 185                 190

Asp Cys Leu Glu Glu Gln Asn Met Ser Ser Pro Cys Glu Gln Glu Glu
        195                 200                 205

His Arg Thr Leu Glu Leu Phe Pro Leu His Pro Glu Gly Arg
    210                 215                 220

<210> SEQ ID NO 33
<211> LENGTH: 44
<212> TYPE: DNA
<213> ORGANISM: Artificial Sequence
<220> FEATURE:
<223> OTHER INFORMATION: Synthetic Construct, GeneRacer RNA oligo
<220> FEATURE:
<221> NAME/KEY: misc_feature
<222> LOCATION: (5)..(5)
<223> OTHER INFORMATION: n = u
<220> FEATURE:
<221> NAME/KEY: misc_feature
<222> LOCATION: (21)..(21)
<223> OTHER INFORMATION: n = u
<220> FEATURE:
<221> NAME/KEY: misc_feature
<222> LOCATION: (26)..(26)
<223> OTHER INFORMATION: n = u
<220> FEATURE:
<221> NAME/KEY: misc_feature
<222> LOCATION: (31)..(31)
<223> OTHER INFORMATION: n = u
<220> FEATURE:
<221> NAME/KEY: misc_feature
<222> LOCATION: (39)..(39)
<223> OTHER INFORMATION: n = u

<400> SEQUENCE: 33
cgacnggagc acgaggacac ngacanggac ngaaggagna gaaa                44
```

```
<210> SEQ ID NO 34
<211> LENGTH: 54
<212> TYPE: DNA
<213> ORGANISM: Artificial Sequence
<220> FEATURE:
<223> OTHER INFORMATION: Synthetic Construct, GeneRacer oligo dT primer

<400> SEQUENCE: 34
gctgtcaacg atacgctacg taacggcatg acagtgtttt ttttttttt tttt          54

<210> SEQ ID NO 35
<211> LENGTH: 40
<212> TYPE: DNA
<213> ORGANISM: Artificial Sequence
<220> FEATURE:
<223> OTHER INFORMATION: PCR primer GR5-2

<400> SEQUENCE: 35
ttttggcgcg ccggacactg acttggactg aaggagtaga                         40

<210> SEQ ID NO 36
<211> LENGTH: 38
<212> TYPE: DNA
<213> ORGANISM: Artificial Sequence
<220> FEATURE:
<223> OTHER INFORMATION: PCR primer GR3-2N

<400> SEQUENCE: 36
tttttattgc ggccgcgcta cgtaacggca tgacagtg                           38

<210> SEQ ID NO 37
<211> LENGTH: 33
<212> TYPE: DNA
<213> ORGANISM: Artificial Sequence
<220> FEATURE:
<223> OTHER INFORMATION: PCR primer GR3-2P

<400> SEQUENCE: 37
tttttaatta agctacgtaa cggcatgaca gtg                                33

<210> SEQ ID NO 38
<211> LENGTH: 32
<212> TYPE: DNA
<213> ORGANISM: Artificial Sequence
<220> FEATURE:
<223> OTHER INFORMATION: PCR primer 59340U

<400> SEQUENCE: 38
aaggcgcgcc atggaaaacg aagtaaacgc ag                                 32

<210> SEQ ID NO 39
<211> LENGTH: 34
<212> TYPE: DNA
<213> ORGANISM: Artificial Sequence
<220> FEATURE:
<223> OTHER INFORMATION: PCR primer 59340L

<400> SEQUENCE: 39
cgttaattaa ttacaaccca ttaccattac tatc                               34

<210> SEQ ID NO 40
<211> LENGTH: 34
<212> TYPE: DNA
<213> ORGANISM: Artificial Sequence
<220> FEATURE:
<223> OTHER INFORMATION: PCR primer 11260U
```

<400> SEQUENCE: 40
aaggcgcgcc agttgaggac tttacatctg aaca  34

<210> SEQ ID NO 41
<211> LENGTH: 30
<212> TYPE: DNA
<213> ORGANISM: Artificial Sequence
<220> FEATURE:
<223> OTHER INFORMATION: PCR primer 11260L

<400> SEQUENCE: 41
aattaattaa ccatgcattg gaaaatatct  30

<210> SEQ ID NO 42
<211> LENGTH: 37
<212> TYPE: DNA
<213> ORGANISM: Artificial Sequence
<220> FEATURE:
<223> OTHER INFORMATION: PCR primer 46480U

<400> SEQUENCE: 42
aggcgcgcca aaatgaaggt tcatgagttt tcgaatg  37

<210> SEQ ID NO 43
<211> LENGTH: 34
<212> TYPE: DNA
<213> ORGANISM: Artificial Sequence
<220> FEATURE:
<223> OTHER INFORMATION: PCR primer 46480L

<400> SEQUENCE: 43
agttaattaa tcatctccct tcaggatgga gagg  34

<210> SEQ ID NO 44
<211> LENGTH: 30
<212> TYPE: DNA
<213> ORGANISM: Artificial Sequence
<220> FEATURE:
<223> OTHER INFORMATION: PCR primer GhCIR1NL

<400> SEQUENCE: 44
ggttaattaa ttgagctcga tgatgatggt  30

<210> SEQ ID NO 45
<211> LENGTH: 36
<212> TYPE: DNA
<213> ORGANISM: Artificial Sequence
<220> FEATURE:
<223> OTHER INFORMATION: PCR primer GhCIR1CU

<400> SEQUENCE: 45
aaggcgcgcc aaaatgcctg tttttcatcc tcctcc  36

<210> SEQ ID NO 46
<211> LENGTH: 34
<212> TYPE: DNA
<213> ORGANISM: Artificial Sequence
<220> FEATURE:
<223> OTHER INFORMATION: PCR primer GhCIR1T

<400> SEQUENCE: 46
ccttaattaa gaagaaatca atgaaacgat gttc  34

```
<210> SEQ ID NO 47
<211> LENGTH: 34
<212> TYPE: DNA
<213> ORGANISM: Artificial Sequence
<220> FEATURE:
<223> OTHER INFORMATION: PCR primer VP16U

<400> SEQUENCE: 47
ccttaattaa cgccccccg accgatgtca gcct                                34

<210> SEQ ID NO 48
<211> LENGTH: 33
<212> TYPE: DNA
<213> ORGANISM: Artificial Sequence
<220> FEATURE:
<223> OTHER INFORMATION: PCR primer VP16L

<400> SEQUENCE: 48
ttttaattaa cccaccgtac tcgtcaattc caa                                 33

<210> SEQ ID NO 49
<211> LENGTH: 30
<212> TYPE: DNA
<213> ORGANISM: Artificial Sequence
<220> FEATURE:
<223> OTHER INFORMATION: PCR primer GhCIR1N2L

<400> SEQUENCE: 49
gattaattaa agttttacca ataggcctgc                                     30

<210> SEQ ID NO 50
<211> LENGTH: 33
<212> TYPE: DNA
<213> ORGANISM: Artificial Sequence
<220> FEATURE:
<223> OTHER INFORMATION: PCR primer At3g11260U2

<400> SEQUENCE: 50
ttttaattaa tccatcaact agagatgttt ttg                                 33

<210> SEQ ID NO 51
<211> LENGTH: 26
<212> TYPE: DNA
<213> ORGANISM: Artificial Sequence
<220> FEATURE:
<223> OTHER INFORMATION: PCR primer GhCIR1T188AU

<400> SEQUENCE: 51
tcatcacgag gccttgccat tgtttc                                         26

<210> SEQ ID NO 52
<211> LENGTH: 26
<212> TYPE: DNA
<213> ORGANISM: Artificial Sequence
<220> FEATURE:
<223> OTHER INFORMATION: PCR primer GhCIR1T188AL

<400> SEQUENCE: 52
gaaacaatgg caaggcctcg tgatga                                         26

<210> SEQ ID NO 53
<211> LENGTH: 27
<212> TYPE: DNA
<213> ORGANISM: Artificial Sequence
<220> FEATURE:
<223> OTHER INFORMATION: PCR primer GhCIR1T188DU
```

```
<400> SEQUENCE: 53
tcatcacgag gatttgccat tgtttcc                                          27

<210> SEQ ID NO 54
<211> LENGTH: 27
<212> TYPE: DNA
<213> ORGANISM: Artificial Sequence
<220> FEATURE:
<223> OTHER INFORMATION: PCR primer GhCIR1T188DL

<400> SEQUENCE: 54
ggaaacaatg gcaaatcctc gtgatga                                          27

<210> SEQ ID NO 55
<211> LENGTH: 28
<212> TYPE: DNA
<213> ORGANISM: Artificial Sequence
<220> FEATURE:
<223> OTHER INFORMATION: PCR primer GhCIR1deltaC45

<400> SEQUENCE: 55
ttaattaaaa caccagtcgg gtgcaatg                                         28

<210> SEQ ID NO 56
<211> LENGTH: 41
<212> TYPE: DNA
<213> ORGANISM: Artificial Sequence
<220> FEATURE:
<223> OTHER INFORMATION: PCR primer GhCIR1E236A

<400> SEQUENCE: 56
ttttaattaa gaagaaatca atgaaacgat gtgccccaga a                          41

<210> SEQ ID NO 57
<211> LENGTH: 735
<212> TYPE: DNA
<213> ORGANISM: Gossypium hirsutum

<400> SEQUENCE: 57
atggaaggtg gcggcggcgg cggtggtgga gggaattcac ggtggaaccc gacgaaggag       60
caaataagca tgcttgaaag cttgtacaag caagggataa gaaccccaag tgctgatcag      120
atacagcaaa taaccagtag gctcaaagct tatggcacca ttgaaggcaa aaacgtgttc      180
tattggttcc aaaatcataa agctcgtcaa aggcagaaac aaaagcaaga gaatttggct      240
tatatcaacc gttacattca ccatcatcat cgagctcaac ctgttttca tcctcctcct       300 tgcaccaatg ttgtttgtgc tggtccatat tttgtaccac aagctgatca tcaccatcat      360
ctaggctttt accctcagtg tcccaaggtt cttctcccta gtagatcaat taaagaaga       420 ggcaggccta ttggtaaaac tggaaagtct ctattttaca acggaaatgc ttatgatcat      480
accatggttc catcacctga tactgaaaac ttatacactg gagcattcaa caatggcggc      540
ggcgccacta atcatcacga gacattgcca ttgtttccat tgcacccgac tggtgtttcc      600
gaagagacgt taatggcttc atcatcacca actggttcaa cttcatgtga gacgacgata      660
tctgctggtg gtgttgataa ccatgaaagt aataatgaag gttctgggga acatcgtttc      720
attgatttct tctga                                                       735

<210> SEQ ID NO 58
<211> LENGTH: 708
<212> TYPE: DNA
<213> ORGANISM: Gossypium hirsutum
```

<400> SEQUENCE: 58

```
atggaaggtg gcggcggcgg cggtggtgga gggaattcac ggtggaaccc gacgaaggag      60
caaataagca tgcttgaaag cttgtacaag caagggataa gaaccccaag tgctgatcag     120
atacagcaaa taaccagtag gctcaaagct tatggcacca ttgaaggcaa aaacgtgttc     180
tattggttcc aaaatcataa agctcgtcaa aggcagaaac aaaagcaaga gaatttggct     240
tatatcaacc gttacattca ccatcatcat cgagctcaac ctgttttttca tcctcctcct     300
tgcaccaatg ttgtttgtgc tggtccatat tttgtaccac aagctgatca tcaccatcat     360
ctaggctttt accctcagtg tcccaaggtt cttctcccta gtagatcaat taaaagaaga     420
ggcaggccta ttggtaaaac tttaattaat ccatcaacta gagatgtttt tgaaataagc     480
gaagaagatt gtcaagagga agagaaggtg atagagacat acaactcttt ccggtgaat      540
tcatttgaag actccaactc caaggtggac aaaatgagag ctagaggcaa taaccagtac     600
cgtgaatata ttcgagagac caccacgacg tcgtttttctc catactcatc atgtggagct     660
gaaatggaac atccaccgcc attagatctt cgattaagct ttctttaa                  708
```

<210> SEQ ID NO 59
<211> LENGTH: 6
<212> TYPE: PRT
<213> ORGANISM: Gossypium hirsutum

<400> SEQUENCE: 59

Lys Arg Arg Gly Arg Pro
1               5

<210> SEQ ID NO 60
<211> LENGTH: 73
<212> TYPE: PRT
<213> ORGANISM: Artificial Sequence
<220> FEATURE:
<223> OTHER INFORMATION: Synthetic Construct, signature sequence
<220> FEATURE:
<221> NAME/KEY: MISC_FEATURE
<222> LOCATION: (1)..(1)
<223> OTHER INFORMATION: X = a polypeptide chain of any number of amino
      acid residues between 13 and 23 residues
<220> FEATURE:
<221> NAME/KEY: MISC_FEATURE
<222> LOCATION: (7)..(7)
<223> OTHER INFORMATION: X = K or V
<220> FEATURE:
<221> NAME/KEY: MISC_FEATURE
<222> LOCATION: (8)..(8)
<223> OTHER INFORMATION: X = D or E
<220> FEATURE:
<221> NAME/KEY: MISC_FEATURE
<222> LOCATION: (10)..(10)
<223> OTHER INFORMATION: X = I or L
<220> FEATURE:
<221> NAME/KEY: MISC_FEATURE
<222> LOCATION: (11)..(11)
<223> OTHER INFORMATION: X = S, T or K
<220> FEATURE:
<221> NAME/KEY: MISC_FEATURE
<222> LOCATION: (12)..(12)
<223> OTHER INFORMATION: X = M, I or L
<220> FEATURE:
<221> NAME/KEY: MISC_FEATURE
<222> LOCATION: (14)..(14)
<223> OTHER INFORMATION: X = E or T
<220> FEATURE:
<221> NAME/KEY: MISC_FEATURE
<222> LOCATION: (15)..(15)
<223> OTHER INFORMATION: X = S, N or D

```
<220> FEATURE:
<221> NAME/KEY: MISC_FEATURE
<222> LOCATION: (17)..(17)
<223> OTHER INFORMATION: X = F or Y
<220> FEATURE:
<221> NAME/KEY: MISC_FEATURE
<222> LOCATION: (18)..(18)
<223> OTHER INFORMATION: X = K or R
<220> FEATURE:
<221> NAME/KEY: MISC_FEATURE
<222> LOCATION: (19)..(19)
<223> OTHER INFORMATION: X = Q, E or A
<220> FEATURE:
<221> NAME/KEY: MISC_FEATURE
<222> LOCATION: (21)..(21)
<223> OTHER INFORMATION: X can be any naturally occurring amino acid
<220> FEATURE:
<221> NAME/KEY: MISC_FEATURE
<222> LOCATION: (25)..(25)
<223> OTHER INFORMATION: X = S or T
<220> FEATURE:
<221> NAME/KEY: MISC_FEATURE
<222> LOCATION: (26)..(26)
<223> OTHER INFORMATION: X = A or T
<220> FEATURE:
<221> NAME/KEY: MISC_FEATURE
<222> LOCATION: (31)..(31)
<223> OTHER INFORMATION: X = Q or K
<220> FEATURE:
<221> NAME/KEY: MISC_FEATURE
<222> LOCATION: (33)..(33)
<223> OTHER INFORMATION: X = S or T
<220> FEATURE:
<221> NAME/KEY: MISC_FEATURE
<222> LOCATION: (34)..(34)
<223> OTHER INFORMATION: X = G, S or T
<220> FEATURE:
<221> NAME/KEY: MISC_FEATURE
<222> LOCATION: (35)..(35)
<223> OTHER INFORMATION: X = R or E
<220> FEATURE:
<221> NAME/KEY: MISC_FEATURE
<222> LOCATION: (37)..(37)
<223> OTHER INFORMATION: X = K, R or S
<220> FEATURE:
<221> NAME/KEY: MISC_FEATURE
<222> LOCATION: (38)..(38)
<223> OTHER INFORMATION: X = A or F
<220> FEATURE:
<221> NAME/KEY: MISC_FEATURE
<222> LOCATION: (41)..(41)
<223> OTHER INFORMATION: X = K, H or T
<220> FEATURE:
<221> NAME/KEY: MISC_FEATURE
<222> LOCATION: (44)..(44)
<223> OTHER INFORMATION: X = G or S
<220> FEATURE:
<221> NAME/KEY: MISC_FEATURE
<222> LOCATION: (58)..(58)
<223> OTHER INFORMATION: X = Q or E
<220> FEATURE:
<221> NAME/KEY: MISC_FEATURE
<222> LOCATION: (62)..(62)
<223> OTHER INFORMATION: X = Q or R
<220> FEATURE:
<221> NAME/KEY: MISC_FEATURE
<222> LOCATION: (63)..(63)
<223> OTHER INFORMATION: Xaa can be any naturally occurring amino acid
<220> FEATURE:
<221> NAME/KEY: MISC_FEATURE
<222> LOCATION: (64)..(64)
<223> OTHER INFORMATION: X = a polypeptide chain of any number of amino
      acid residues between 29 and 101 residues
<220> FEATURE:
<221> NAME/KEY: MISC_FEATURE
<222> LOCATION: (65)..(65)
<223> OTHER INFORMATION: X = E or K
```

-continued

```
<220> FEATURE:
<221> NAME/KEY: MISC_FEATURE
<222> LOCATION: (66)..(66)
<223> OTHER INFORMATION: X = S, T, A, C, I, G, V, L, M, N, Q or P
<220> FEATURE:
<221> NAME/KEY: MISC_FEATURE
<222> LOCATION: (68)..(68)
<223> OTHER INFORMATION: X = P or Q
<220> FEATURE:
<221> NAME/KEY: MISC_FEATURE
<222> LOCATION: (72)..(72)
<223> OTHER INFORMATION: Xaa can be any naturally occurring amino acid
<220> FEATURE:
<221> NAME/KEY: MISC_FEATURE
<222> LOCATION: (73)..(73)
<223> OTHER INFORMATION: X = a polypeptide chain of any number of amino
      acid residues between 13 and 57 residues

<400> SEQUENCE: 60

Xaa Arg Trp Asn Pro Thr Xaa Xaa Gln Xaa Xaa Xaa Leu Xaa Xaa Leu
1               5                   10                  15

Xaa Xaa Xaa Gly Xaa Arg Thr Pro Xaa Xaa Asp Gln Ile Gln Xaa Ile
            20                  25                  30

Xaa Xaa Xaa Leu Xaa Xaa Tyr Gly Xaa Ile Glu Xaa Lys Asn Val Phe
        35                  40                  45

Tyr Trp Phe Gln Asn His Lys Ala Arg Xaa Arg Gln Lys Xaa Xaa Xaa
    50                  55                  60

Xaa Xaa Leu Xaa Leu Phe Pro Xaa Xaa
65                  70

<210> SEQ ID NO 61
<211> LENGTH: 73
<212> TYPE: PRT
<213> ORGANISM: Artificial Sequence
<220> FEATURE:
<223> OTHER INFORMATION: Synthetic Construct, expanded signature
      sequence
<220> FEATURE:
<221> NAME/KEY: MISC_FEATURE
<222> LOCATION: (1)..(1)
<223> OTHER INFORMATION: X = a polypeptide chain of any number of amino
      acid residues between 13 and 23 residues
<220> FEATURE:
<221> NAME/KEY: MISC_FEATURE
<222> LOCATION: (7)..(7)
<223> OTHER INFORMATION: X = K, E, Q, R, I, M, L or V
<220> FEATURE:
<221> NAME/KEY: MISC_FEATURE
<222> LOCATION: (8)..(8)
<223> OTHER INFORMATION: X = E, D, N, K or Q
<220> FEATURE:
<221> NAME/KEY: MISC_FEATURE
<222> LOCATION: (10)..(10)
<223> OTHER INFORMATION: X = I, L, M or V
<220> FEATURE:
<221> NAME/KEY: MISC_FEATURE
<222> LOCATION: (11)..(11)
<223> OTHER INFORMATION: X = E, K, N, S, T, Q or R
<220> FEATURE:
<221> NAME/KEY: MISC_FEATURE
<222> LOCATION: (12)..(12)
<223> OTHER INFORMATION: X = M, I, L or V
<220> FEATURE:
<221> NAME/KEY: MISC_FEATURE
<222> LOCATION: (14)..(14)
<223> OTHER INFORMATION: X = D, E, K, Q, S or T
<220> FEATURE:
<221> NAME/KEY: MISC_FEATURE
<222> LOCATION: (15)..(15)
<223> OTHER INFORMATION: X = A, D, E, H, N, S or T
<220> FEATURE:
<221> NAME/KEY: MISC_FEATURE
<222> LOCATION: (17)..(17)
<223> OTHER INFORMATION: X = A, D, E, K, R, Q or S
```

```
<220> FEATURE:
<221> NAME/KEY: MISC_FEATURE
<222> LOCATION: (18)..(18)
<223> OTHER INFORMATION: X = E, Q, K or R
<220> FEATURE:
<221> NAME/KEY: MISC_FEATURE
<222> LOCATION: (19)..(19)
<223> OTHER INFORMATION: X = A, D, E, K, R, Q or S
<220> FEATURE:
<221> NAME/KEY: MISC_FEATURE
<222> LOCATION: (21)..(21)
<223> OTHER INFORMATION: X = I, L, M or V
<220> FEATURE:
<221> NAME/KEY: MISC_FEATURE
<222> LOCATION: (25)..(26)
<223> OTHER INFORMATION: X = A, S or T
<220> FEATURE:
<221> NAME/KEY: MISC_FEATURE
<222> LOCATION: (31)..(31)
<223> OTHER INFORMATION: X = E, K, Q or R
<220> FEATURE:
<221> NAME/KEY: MISC_FEATURE
<222> LOCATION: (33)..(33)
<223> OTHER INFORMATION: X = A, S or T
<220> FEATURE:
<221> NAME/KEY: misc_feature
<222> LOCATION: (34)..(34)
<223> OTHER INFORMATION: X = A, G, S or T
<220> FEATURE:
<221> NAME/KEY: MISC_FEATURE
<222> LOCATION: (35)..(35)
<223> OTHER INFORMATION: X = D, E, K, Q or R
<220> FEATURE:
<221> NAME/KEY: MISC_FEATURE
<222> LOCATION: (37)..(37)
<223> OTHER INFORMATION: X = A, E, Q, K, R, S or T
<220> FEATURE:
<221> NAME/KEY: MISC_FEATURE
<222> LOCATION: (38)..(38)
<223> OTHER INFORMATION: X = A, S, F, W or Y
<220> FEATURE:
<221> NAME/KEY: MISC_FEATURE
<222> LOCATION: (41)..(41)
<223> OTHER INFORMATION: X = E, Q, H, K, T or Y
<220> FEATURE:
<221> NAME/KEY: MISC_FEATURE
<222> LOCATION: (44)..(44)
<223> OTHER INFORMATION: X = A, G, S or T
<220> FEATURE:
<221> NAME/KEY: MISC_FEATURE
<222> LOCATION: (58)..(58)
<223> OTHER INFORMATION: X = D, E, Q, K or R
<220> FEATURE:
<221> NAME/KEY: MISC_FEATURE
<222> LOCATION: (62)..(63)
<223> OTHER INFORMATION: X = E, K, Q or R
<220> FEATURE:
<221> NAME/KEY: MISC_FEATURE
<222> LOCATION: (64)..(64)
<223> OTHER INFORMATION: X = a polypeptide chain of any number of amino
     acid residues between 29 and 101 residues
<220> FEATURE:
<221> NAME/KEY: MISC_FEATURE
<222> LOCATION: (65)..(65)
<223> OTHER INFORMATION: X = D, E, K, Q or R
<220> FEATURE:
<221> NAME/KEY: MISC_FEATURE
<222> LOCATION: (66)..(66)
<223> OTHER INFORMATION: X = S, T, A, C, I, G, V, L, M, N, Q or P
<220> FEATURE:
<221> NAME/KEY: MISC_FEATURE
<222> LOCATION: (68)..(68)
<223> OTHER INFORMATION: X = E, P, Q, K or R
<220> FEATURE:
<221> NAME/KEY: MISC_FEATURE
<222> LOCATION: (72)..(72)
<223> OTHER INFORMATION: X = M, I, L or V
```

```
<220> FEATURE:
<221> NAME/KEY: MISC_FEATURE
<222> LOCATION: (73)..(73)
<223> OTHER INFORMATION: X = a polypeptide chain of any number of amino
      acid residues between 13 and 57 residues

<400> SEQUENCE: 61

Xaa Arg Trp Asn Pro Thr Xaa Xaa Gln Xaa Xaa Xaa Leu Xaa Xaa Leu
1               5                   10                  15

Xaa Xaa Xaa Gly Xaa Arg Thr Pro Xaa Xaa Asp Gln Ile Gln Xaa Ile
            20                  25                  30

Xaa Xaa Xaa Leu Xaa Xaa Tyr Gly Xaa Ile Glu Xaa Lys Asn Val Phe
        35                  40                  45

Tyr Trp Phe Gln Asn His Lys Ala Arg Xaa Arg Gln Lys Xaa Xaa Xaa
    50                  55                  60

Xaa Xaa Leu Xaa Leu Phe Pro Xaa Xaa
65                  70

<210> SEQ ID NO 62
<211> LENGTH: 99
<212> TYPE: DNA
<213> ORGANISM: Artificial Sequence
<220> FEATURE:
<223> OTHER INFORMATION: Synthetic Construct

<400> SEQUENCE: 62
ctgtacaagt taattaacta ccctatgat gtacctgact atgcataccc ttatgatgta     60
ccagactatg ctcaccatca ccaccatcac tgactagtc                          99

<210> SEQ ID NO 63
<211> LENGTH: 30
<212> TYPE: PRT
<213> ORGANISM: Artificial Sequence
<220> FEATURE:
<223> OTHER INFORMATION: Synthetic Construct

<400> SEQUENCE: 63

Leu Tyr Lys Leu Ile Asn Tyr Pro Tyr Asp Val Pro Asp Tyr Ala Tyr
1               5                   10                  15

Pro Tyr Asp Val Pro Asp Tyr Ala His His His His His His
            20                  25                  30

<210> SEQ ID NO 64
<211> LENGTH: 4
<212> TYPE: PRT
<213> ORGANISM: Agrobacterium tumefaciens

<400> SEQUENCE: 64

Arg Lys Gly Lys
1

<210> SEQ ID NO 65
<211> LENGTH: 6
<212> TYPE: PRT
<213> ORGANISM: Gossypium hirsutum
<220> FEATURE:
<221> NAME/KEY: MISC_FEATURE
<222> LOCATION: (3)..(3)
<223> OTHER INFORMATION: X = any amino acid

<400> SEQUENCE: 65

Thr Leu Xaa Leu Phe Pro
1               5
```

```
<210> SEQ ID NO 66
<211> LENGTH: 6
<212> TYPE: PRT
<213> ORGANISM: Artificial Sequence
<220> FEATURE:
<223> OTHER INFORMATION: Synthetic Construct, signature sequence
<220> FEATURE:
<221> NAME/KEY: MISC_FEATURE
<222> LOCATION: (6)..(6)
<223> OTHER INFORMATION: X can be any naturally occurring amino acid

<400> SEQUENCE: 66

Arg Trp Asn Pro Thr Xaa
1               5

<210> SEQ ID NO 67
<211> LENGTH: 6
<212> TYPE: PRT
<213> ORGANISM: Artificial Sequence
<220> FEATURE:
<223> OTHER INFORMATION: Synthetic Construct, signature sequence

<400> SEQUENCE: 67

Arg Trp Asn Pro Thr Lys
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Construct, signature sequence

<400> SEQUENCE: 68

Arg Trp Asn Pro Thr Val
1               5
```

US 8,586,824 B2

PLANT HOMEODOMAIN PROTEIN-ENCODING GENES AND THEIR USES

CROSS-REFERENCES TO RELATED APPLICATIONS

This application is a 35 U.S.C. 371 National Phase Entry Application from PCT/US2006/004777, filed Feb. 13, 2006.

STATEMENT REGARDING FEDERALLY SPONSORED RESEARCH OR DEVELOPMENT

Not applicable.

REFERENCE TO A SEQUENCE LISTING

The present application includes a Sequence Listing filed in electronic format. The Sequence Listing is entitled "2577-166_ST25.txt" created on Mar. 11, 2013, and is 78,000 bytes in size. The information in the electronic format of the Sequence Listing is part of the present application and is incorporated herein by reference in its entirety.

BACKGROUND OF THE INVENTION

1. Field of the Invention

The present invention relates to polynucleotides that induce or promote regeneration of plants.

2. Description of the Related Art

A bibliography follows at the end of the Detailed Description of the Invention. The listed references are all incorporated herein by reference.

Organogenesis and embryogenesis are two pathways leading to plant regeneration in a plant tissue culture. Traditionally, these two pathways are achieved through the manipulation of the contents and ratios of hormones in a plant-cell-culture medium as well as environmental conditions of a plant cell culture. Today, it is well known that these hormones and environmental cues activate specific proteins that play pivotal roles in the initiation of organogenesis or embryogenesis. This understanding opens a new door to novel methods for manipulation of plant regeneration through a direct control of gene expression. For example, over-expression of *Arabidopsis* ESR1 and ESR2, which are transcriptional factors belonging to AP2 family, induces shoot regeneration in a plant-cell-culture medium that does not contain any cytokinins (Banno et al., 2001; U.S. Pat. Nos. 6,441,276; 6,407,312). Likewise, genes involved in cytokinin production, such as ipt, can be over-expressed to substitute for a cytokinin in a culture medium (Ooms et al., 1983, Smigocki and Owens, 1988; Ebinuma et al., 1997). Similarly, genes involved in transduction of cytokinin signals, such as cytokinin activated histidine kinase (CKI1) and two-component transcription activators (ARR1 and ARR2), can promote shoot regeneration in *Arabidopsis* (Kakimoto, 1996; Sakai et al., 2001; Hwang and Sheen, 2001; Imamura et al., 2003).

Gene transformation is an important tool of molecular biology as well as crop improvement. Although currently many plants can be transformed using methods such as *Agrobacterium*-mediated T-DNA conjugation and particle gun bombardment, the efficiency of those methods varies, and there is a need to improve transformation efficiency of important crops, such as cotton, maize and soybean. Improved transformation efficiency is especially important to perform a large-scale analysis of gene functions in these crops. Improved transformation efficiency can be achieved by a higher rate of successful transformation, easier selection of successful transformants, shorter time for such a selection, or lesser use of antibiotics or herbicides for such a selection, and will generate economical, industrial or academic benefits.

Cotton is an economically important crop but is one of the most difficult plants to transform. It usually takes about 1.5 years to produce transgenic seeds. No cotton gene has so far been reported to improve plant regeneration or transformation although some *Arabidopsis* genes have been reported to improve transformation efficiency of root explants of *Arabidopsis* (Bann et al., 2001; U.S. Pat. Nos. 6,441,276; 6,407,312). Therefore, there is a need for such a cotton gene.

Although currently antibiotics or herbicide resistance markers are almost exclusively used for selection of plant transformants (Yoder and Goldsbrough, 1994), they generally have negative effects on proliferation and differentiation and sometimes retard differentiation of adventitious shoots during the transformation process (Ebinuma et al., 1997). Further, they pose environmental or health risks (Bryant and Leather, 1992; Gressel, 1992; Flavell et al., 1992). The availability of new selection markers also facilitates stacking of multiple transgenic traits. Consequently, there have been considerable efforts to develop alternative selection systems for plant transformants. U.S. Pat. Nos. 6,441,276 and 6,407,312 disclose methods of selecting transformants using ESR genes.

*Arabidopsis* Wuschel was first described as a mutant defective in shoot apical meristem initiation and maintenance (Endrizzi et al., 1996; Laux et al., 1996; Mayer et al., 1998). The phenotype was attributed to mutation of a single gene (Wus) that encodes a homeodomain ("HD") protein, a probable transcriptional factor (Mayer et al., 1998). Interestingly, although *Arabidopsis* contains at least 14 genes that are predicted to encode a highly similar HD domain at the N-terminus and a highly divergent sequence at the C-terminus to Wus gene, none of them could substitute for Wus in the Wuschel mutant. This indicates that these genes have different functions. Recently it was demonstrated that the mRNAs of these genes have unique expression profiles (Haecker et al., 2004). Except for Wus and Prs, the functions of these genes have not yet been defined. Although over-expression of the *Arabidopsis* Wus induces shoot or somatic embryo formation in *Arabidopsis* and rice (Zuo et al., 2002; Kamiya et al., 2003), not every HD domain protein has this property. The *Arabidopsis* PRS, for example, was required for flower development and its over-expression induces cell proliferation rather than shoot regeneration (Matsumoto and Okada, 2001). Another HD domain protein, At1g46480, was not able to induce shoot regeneration in a cytokinin-free medium (Table 1). A PCT publication WO 01/23575 A2 discloses several putative Wuschel homologues from maize and soybean. It was also shown that over-expression of Wuschel also induced shoot regeneration both in *Arabidopsis* and rice (Zuo et al., 2002; Kamiya et al., 2003).

Transcription factors generally consist of at least two modules that are often exchangeable between different members or classes. This type of chimeric transcriptional factors has been well documented in the literature. For example, VXE transcriptional factor is a fusion protein of a viral activation domain VP16, an *E. coli* LexA DNA binding domain and a human estrogen receptor regulatory domain (Zou and Chua, 2000). Surprisingly, a fusion protein containing the HD domain of GhCIR1 and the VP16 activation domain did not promote shoot regeneration (Table 5). This indicates that the HD domain alone is not sufficient for the shoot regeneration enhancing function of certain HD domain proteins. Phylogenic analysis showed that none of the three polynucleotides described in this disclosure, i.e., SEQ ID NOs: 1, 3 and 5, are closely related to Wuschel (FIG. 3).

Development of efficient and simple transformation techniques has made great contribution to rapid advance in molecular genetics in *Arabidopsis*. Currently, both in planta (flora dip) and root explant methods allow a large number of genes to be mutated or transformed (Clough and Bent, 1998; Valvekens et al., 1988). For example, Banno and Chua (2001) have identified an *Arabidopsis* gene by functional screening of an *Arabidopsis* cDNA library using *Arabidopsis* root explants. On the other hand, we identified a non-*Arabidopsis* (GhCIR1) gene by direct functional screening using *Arabidopsis* root explants (Example 2).

SUMMARY OF THE INVENTION

One aspect of the invention relates to novel genes, such as GhCIR1 from cotton (*Gossypium hirsutum*), AtCIR1 and AtCIR2 from *Arabidopsis thaliana*, and a synthetic chimeric genes such as SEQ ID NO: 15.

Another aspect of the invention relates to homologues of the novel genes.

Another aspect of the invention relates to the novel polypeptides encoded by the novel genes.

Another aspect of the invention relates to the homologues, especially, polypeptides containing a signature sequence.

Another aspect of the invention relates to the homologues of the novel genes encoding the polypeptides containing a signature sequence.

Another aspect of the invention relates to transformed cells with the novel genes or the homologues of the novel genes the polypeptides containing a signature sequence.

Another aspect of the invention relates to inducing or promoting regeneration of plants, such as *Arabidopsis* and cotton, using the novel genes.

Another aspect of the invention relates to a method for functional identification of a gene that induces or promotes plant regeneration.

Another aspect of the invention relates to selection or screening of transformants using the novel genes or their homologues as a selection marker.

Another aspect of the invention relates to improving regeneration or transformation efficiency of plants using the novel genes or their homologues.

BRIEF DESCRIPTION OF THE FIGURES

FIGS. 2A-2C show the sequence alignment of Wuschel-related HD domain proteins. Sequences were aligned with the Clustral V method using DNAStar™-MegAlign™ Program set to default parameters (Gap penalty=10; gap length penalty=0.2; delayed divergent sequences=30%; DNA transit weight=0.5). The HD domain and the hexapeptide are marked with line and dotted line, respectively. AtWOX2 (AY251392) (SEQ ID NO: 17), At1g46480 (NM_103605) (SEQ ID NO: 8), At3g11260 (NM_111961) (SEQ ID NO: 6), and PRS (BAB79446) (SEQ ID NO:18) are *Arabidopsis* proteins deduced from mRNA sequences. Wus (NP_565429) (SEQ ID NO:19), LeWUS (CAD61961) (SEQ ID NO: 21), and PhWUS (AAM90847) (SEQ ID NO: 20) are the *Arabidopsis* Wuschel and its homologues of tomato and Petunia, respectively. P0529E05.28 (BAB84412) (SEQ ID NO: 22) is a rice protein expressed specifically in the root quiescent centre. Genebank accession numbers are shown in the parenthesis. Seq. ID3, Seq. ID5, Seq. ID7, Seq. ID9, Seq. ID13, Seq. ID15, Seq. ID17, Seq. ID19, Seq. ID21 and Seq. ID23 (SEQ ID NOs: 23-32) are polypeptide sequences predicted from the polynucleotide sequences disclosed in PCT publication WO 01/23575 A2 as sequence identification numbers 3, 5, 7, 9, 13, 15, 17, 19, 21 and 23 there.

FIG. 7 shows the use of GhCIR1 and AtCIR2 as transformation selection markers. *Arabidopsis* root explants were co-cultured with AGL1 carrying pX6-GFP (A), pX6-GhCIR1 (B and C) or pX6-AtCIR2 (D) for 3 days. Plantlets were regenerated from SR medium supplemented with 50 ml/ml kanamycin (A); RI medium supplemented with 50 mg/l kanamycin (B); or kanamycin-free RI medium (C and D). The plates were incubated at 22° C. for 31 days.

DETAILED DESCRIPTION OF THE INVENTION

Figure 1:
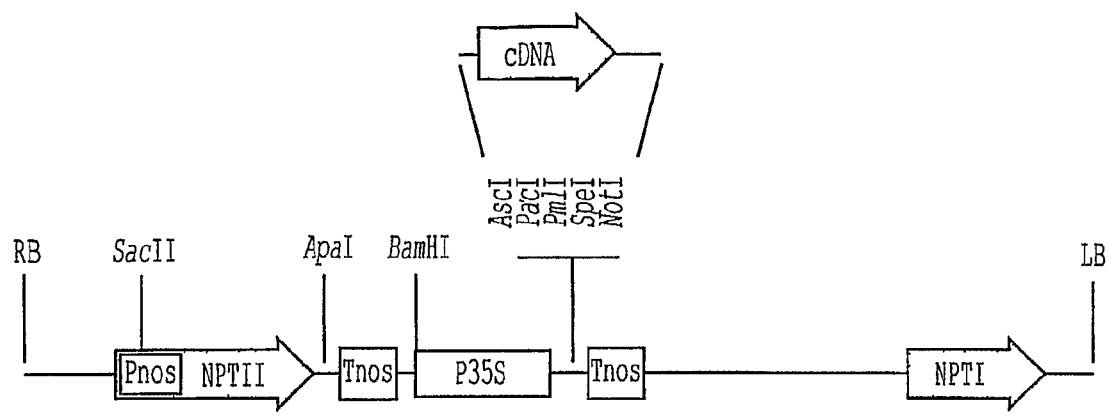
FIG. 1 shows the gene organization in T-DNA region of pSK36. Promoters are shown as empty boxes. Protein coding regions are shown as dark arrows. Gene transcriptional terminators are shown as gray boxes. Cotton cDNAs are directionally inserted between AscI and Not1 sites so that the expression of the inserted cDNAs is under the regulation of CaMV 35S promoter (P35S). NPTI and NPTII are kanamycin resistance markers for bacteria and plants. Pnos and Tnos are the promoter and terminator of the *Agrobacterium* nopaline synthase gene. LB and RB are the left and right borders.
Figures 3A, 3B:
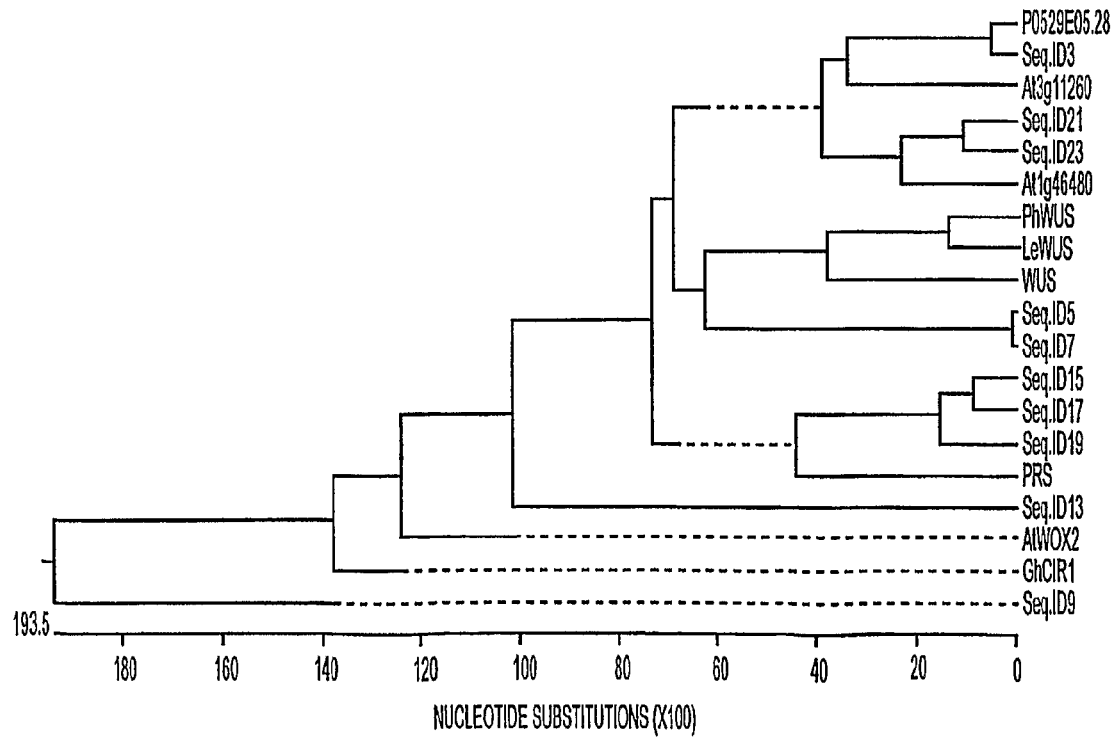
FIG. 3 shows the evolutionary relationship of Wuschel-related HD domain proteins. The amino acid sequences of nineteen GhCIR1-related HD domain proteins were aligned by the Clustal V method using DNAStar™-MegAlign™ Program. The sequence identity and divergence output is shown in A and phylogenic tree is shown in B.
Figure 4A:
FIG. 4 shows the morphology of *Arabidopsis* root regenerants. *Arabidopsis* root explants were co-cultured with AGL1 carrying pSK36-GhCIR1 (A), pSK36-AtCIR1 (B), pSK36-AtCIR2 (C) and control vector pSK36 (D). The regenerants were photographed using a dissecting microscope (Nikon™ SMZ 800™) after culturing for three weeks at 22° C. in SR medium. The white arrows in panel A and B point somatic embryos. The black arrow in panel C points a typical regenerant derived from pSK36-AtCIR2.
Figure 4B:
Figure 4C:
Figure 4D:

A "gene" as used in this application means a segment of DNA, encoding a polypeptide or an RNA molecule. A gene can include regions preceding and following the coding DNA, which regions control or regulate the expression of the encoded polypeptide. A gene can include one or more introns.

"Isolated" as used in this application means that a molecule is separated from its naturally occurring environment. Isolated as used in this application does not necessarily mean a molecule is contained in isolation from all other molecules of the same or different kind, or disconnected to any other molecules; therefore, an isolated molecule may still be covalently bonded to a heterogeneous molecule to form a so-called fusion protein or an artificially created vector for cloning or expression and the fusion protein or artificially created vector still can be an isolated molecule of a different kind. In the context of an isolated nucleotide, "isolated" means that the nucleotide is separated at least from its naturally occurring macromolecular structure, for example, chromosome.

"Plant" as used in this application means only biological organisms classified in Plantae kindom, and cells generated or derived from such organisms. Preferred plants in this application are crops and Arabidopsis. More preferred plants in this application are cotton, rice, corn and Arabidopsis. Most preferred plants in this application are cotton and Arabidopsis.

"Non-supportive of plant regeneration" as used in this application means that there is no substantial plant regeneration from plant explants, and includes no plant regeneration from plant explants.

"Conservatively substituted homologue" as used in this application means that a protein in which one or more residues are substituted by amino acids with similar chemical or biophysical properties, e.g., hydrophobicity, ionic charges, side-chain structure.

"Transformation" or "transforming a cell" as used in this application broadly means any kind of transfer or introduction of a polynucleotide or gene to a cell, including conjugation, transformation, transfection and transduction. Preferred methods include transferring a polynucleotide or gene to a cell by Agrobacterium-mediated T-DNA conjugation or particle bombardment.

"Identity" or "percent identity" or "% identity" as used in this application means the identity calculated by Clustral V method using DNAStar™-MegAlign™ Program.

"Over-expression" as used in this application means that expression of a polynucleotide or gene occurs more than it would naturally occur in a system such as a cell, tissue or organism, including ectopic expression. The over-expression means, preferably at least 25%, more preferably at least 50% and the most preferably at least 100% more expression than the natural expression level.

A nuclear localizing signal (NLS) is a short amino acid sequence which acts like a 'tag' on the exposed surface of a protein. This sequence is used to confine the protein to the cell nucleus and to direct a newly synthesized protein into the nucleus via its recognition by cytosolic nuclear transport receptors. This signal often comprises positively charged amino acid, e.g., lysines or arginines. A protein can be directed to the nucleus by this NLS. An example of NLS is Pro-Pro-Lys-Lys-Lys-Arg-Lys-Val. Additional examples and sequence characteristics of nuclear localization signals can be found in numerous publications, e.g., Cokol et al., 2000, Tinland et al., 1992, which are incorporated by reference. Additional examples can also be found in NLSdb, which is a database of nuclear localization signals (NLSs) and of nuclear proteins targeted to the nucleus by NLS motifs, produced by Rajesh Nair and Phil Carter with Columbia University, New York. As of Oct. 28, 2005, NLSdb contains 308 signals.

By functional screening of approximately 100,000 Gossypium hirsutum cDNAs, four candidate genes have been identified based on the ability to form either a large green callus or complete plantlet in a cytokinin-free medium. PCR amplification and sequencing of one of the candidate genes revealed that the T-DNA contained a cDNA of 1034 nucleotides (SEQ ID NO: 1) encoding an open reading frame of 244 amino acids (SEQ ID NO: 2). Re-cloning of the cDNA into pSK36 confirmed its cytokinin independent regeneration phenotype. As expected, multiple shoots were induced in a single callus and the plants were sterile or had low fertility. To overcome this problem, the gene was placed under control of the VXE inducible promoter in pER10 (Zou et al, 2002). When inducer estradiol was present in the 2ip-free medium, abundant shoots were generated. The gene was therefore named GhCIR1 (Gossypium hirsutum Cytokinin Independent Regeneration).

A BLAST search of the predicted protein showed that it shared a substantial homology to a group of proteins containing a N-terminal homeodomain (HD), a motif of approximately 60 amino acids, known to modulate DNA sequence recognition of transcription factors (Gehring et al., 1994). It is most similar to an Arabidopsis HD domain protein encoded by the putative gene At5g59340 (GeneBank accession NO. NP_200742.1), with the homology extending beyond the HD domain (FIGS. 2A-C). Using default parameters for NCBI Blast search and sequence alignment, the two polypeptide sequences shared 44% identity over the entire open reading frame. It has been reported that the gene contains a 436 nucleotide intron and the predicted protein sequence is shown in SEQ ID NO: 4. The mRNA is expressed in the apical part of zygotic embryos. Mutations in the gene cause only partial defects in embryo development (Haecker et al, 2004). However, there has been no information on its over-expression phenotype.

The HD domains of over a dozen more genes in the Arabidopsis genome share high homology with GhCIR1. Over-expression of the putative GhCIR1 homologue (At5g59340; Genebank accession no. NP_200742) by the estrogen inducible VXE promoter or CaMV 35S promoter, as GhCIR1 did, induced an abundant regeneration of shoots in a cytokinin-free medium and significantly enhanced the production of shoots in a normal medium. A similar effect was observed with At3g11260 as well. On the other hand, At1g46480 (GeneBank No. NP_175145.2) was unable to induce shoot regeneration in a cytokinin-free medium and showed negligible effect to promote shoot regeneration in medium containing 10 µM 2ip (Table 1 and Table 2). We designated the two Arabidopsis genes, At5g59340 and At3g11260, as AtCIR1 (*Arabidopsis thaliana* Cytokinin Independent Regeneration 1) and AtCIR2, respectively.

Although GhCIR1, AtCIR1 and AtCIR2 were all able to induce shoot regeneration in a cytokinin-free medium, plantlets induced by AtCIR2 were distinctively different from those by GhCIR1 and AtCIR1. Both GhCIR1 and AtCIR1 predominantly induced formation of spiky dark-green calli, which may develop into plantlets later. Microscopic examination of the calli regenerated from cytokinin-free medium revealed the spikes resembled somatic embryos. This was supported by the appearance of the root and cotyledon-like structures emerging from the opposite side of the spike (FIG. 4). Furthermore, no trichomes were observed in the putative cotyledons. In contrast, shoots regenerated by over-expressing AtCIR2 in a cytokinin-free medium showed little difference to those transformed with pSK36 vector in a cytokinin-containing regeneration medium. Trichomes were seen in the first two leaves, indicating that they were true leaves and shoots were regenerated via the organogenesis pathway (FIG. 4).

Figure 5A:
FIG. 5 shows cotton somatic embryos derived from transformation of pSK36-GhCIR1. A cotton (Coker 312) pro-embryogenic suspension culture was co-cultured with AGL1 carrying pSK36-GhCIR1 (Panel A) or empty vector pSK36 (Panel B). The transformed cells were allowed to develop somatic embryos for three months under kanamycin selection in hormone-free medium and then photographed using a dissecting microscope. The black arrow in panel A points to a non-separated somatic embryo-like structure and the long white arrows point to normal globular stage somatic embryos. The short white arrow points to an over-sized globular somatic embryo.

To see if GhCIR1 has a similar function in cotton as was found in *Arabidopsis*, we transformed a cotton suspension culture that is poorly embryogenic with pSK36-GhCIR1. In non-transformed cells or cells transformed with pSK36, globular somatic embryos may multiply or start to elongate after reaching certain size in a cytokinin-free medium. On the other hand, when the transformed cells with pSK36-GhCIR1 were regenerated via somatic embryogenic pathway in a cytokinin-free medium, no normal somatic embryos were obtained, but those cells regenerated into embryo-like clusters in which individual embryos failed to separate or globular stage embryos that were much larger than usual (FIG. 5A). These embryos usually died at a later stage. Nevertheless, over-expression of GhCIR1 resulted in about 2-fold more kanamycin resistant somatic embryos compared to the control vector alone (Table 3). This result confirmed that over-expression of GhCIR1 promotes cytokinin-independent plant regeneration across different plant species.

Figure 6:
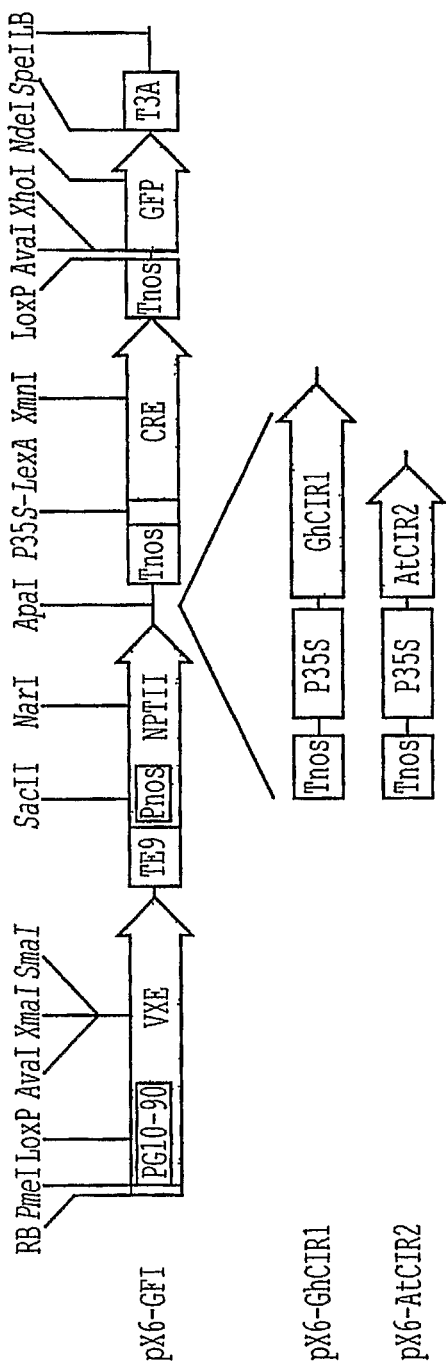
FIG. 6 shows the gene organization of T-DNA region in pX6-GFP and its derivatives. Promoters are shown as empty boxes. Protein coding regions are shown as solid black arrows. Gene transcriptional terminators are shown in gray boxes. CRE recombinase is under control of CaMV 35S-LexA hybrid promoter, which is inducible by estrogen (e.g., estradiol) that activates the VXE transcriptional activator. P35S::GhCIR1 and P35S::AtCIR2 gene cassettes were inserted into the ApaI site to create pX6-GhCIR1 and pX6-AtCIR2, respectively. Pg10-90 is a synthetic promoter that drives the constitutive expression of VXE. LB and RB are the left and right borders.

As over-expression of GhCIR1, AtCIR1 or AtCIR2 was able to induce shoot regeneration in a cytokinin-free medium, which is normally non-supportive of regeneration of *Arabidopsis* root explants, the three genes can be used as a selection marker, and even replace antibiotic or herbicide resistance genes. Inducible promoters can be used to overcome problems associated with plant abnormality resulting from over-expression of regeneration-enhancing genes. Alternatively, these regeneration enhancing genes can be removed using inducible excision systems, for example, estrogen-inducible gene excision system based on VXE inducible expression system and Cre-mediated site-specific recombination (Zuo et al., 2001). In this vector (pX6-GFP), activation of Cre recombinase by estrogen leads to the deletion of the DNA region between the LoxP sites (FIG. 6). The successful excision of the region can be confirmed by the expression of the GFP due to fusion of the GFP ORF with G10-90 promoter.

Figure 8A:
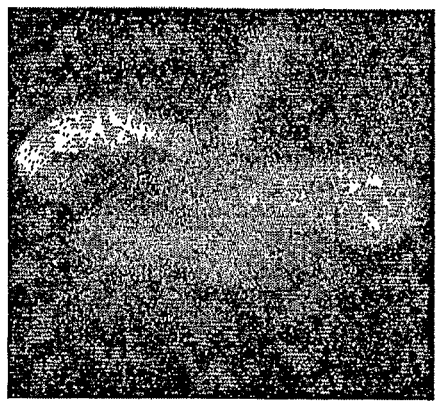
FIG. 8 shows the chemically-induced excision of transformation selection marker. *Arabidopsis* root explants were co-cultured with AGL1 carrying pX6-GhCIR1 for 3 days and plated in kanamycin-free RI medium. The plates were incubated at 22° C. for 3 weeks. Green calli were transferred to RI medium with 10 μM estradiol and incubated for 2 weeks. The shoots generated were photographed using a dissecting microscope (Nikon™ SMZ800™) with a florescent attachment. Panel A shows GFP florescence in the upper part of the shoot. Panel B shows a bright-field picture of the shoot.
Figure 8B:

We cloned P35S::GhCIR1 and P35S::AtCIR2 gene cassettes into the pX6-GFP vector (FIG. 6). Over-expression of GhCIR1 or AtCIR2 gene in *arabidopsis* root explants induced an abundant regeneration of shoots in a medium free of plant-active antibiotics such as kanamycin (FIG. 7). When the early-stage somatic embryos or shoots were transferred to a medium containing estradiol, green, florescent and normal looking shoots were produced (FIG. 8). This indicates that the gene cassettes between the GFP ORF and the G10-90 promoter have been successfully excised. The dramatic drop in shoot regeneration from root explants in RI+ medium also indicates that excision is a highly efficient process (Table 4).

The two putatively separate domains of GhCIR1 were independently over-expressed. Although the HD domains of Wuschel-related proteins are highly conserved, this domain alone did not show the cytokinin-independent regeneration or enhancement of regeneration efficiency phenotypes. Moreover, the fusion protein of the HD domain and an activation domain such as VP16 did not have the transcription activator function (Example 8; Tables 5 and 6). On the other hand, fusion of GhCIR1 HD domain with the putative activation domain of AtCIR2 fully re-constituted a protein with cytokinin-independent regeneration and transformation enhancing functions (Example 10, Table 7). Therefore, the entire coding sequence of GhCIR1, AtCIR1 or AtCIR2 is preferred for cytokinin-independent inducement of regeneration, or promotion of regeneration efficiency phenotypes.

Media Composition

G medium: 1×MS salts, 3% sucrose. 0.8% Agar, pH 5.7
B5 medium: 1×B5 salts, 1×B5 vitamins, 3% sucrose, 0.5 g/L MES, pH 5.7
F1 medium: 1×B5 salts, 2% glucose, 0.5 g/L MES, 0.5 mg/L 2,4-D, 0.05 mg/L Kinetin, 0.2% Phytagel, pH 5.7.
F2 medium: F1, 20 mg/L Acetosyringone.
SR medium: 1×MS salts, 1% sucrose, 0.5 g/L MES, 2 mg/L 2ip, 0.15 mg/L IAA, 200 mg/L Cefotaxim, 35 mg/L kanamycin, 0.2% Phytagel, pH 5.7
SR+ medium: SR medium, 10 µM estradiol.
SR' medium: identical to SR except phytagel is replaced with 0.6% lower melting agrose.
RI medium: 1×MS salts, 1% sucrose, 0.5 g/L MES, 0.15 mg/L IAA, 200 mg/L Cefotaxim, 35 mg/L kanamycin, 0.2% Phytagel, pH 5.7
RI+ medium: RI plus 10 µM estradiol.
W solution: sterile water+400 mg/L Cefotaxim.

Example 1

Construction of a Normalized cDNA Library

Total RNA was extracted from a pool of different cotton tissues which included somatic embryos, pro-embryogenic suspension cultures, roots, cotyledons, shoot tips and auxiliary shoot buds. Poly(A)+ RNA was isolated by PolyA-Tract™ mRNA purification system (Promoge™, UAS) and cDNA was synthesized with GeneRacer™ kit (Invitrogen™, USA). Approximately 0.75 µg polyA+ RNA was ligated with GeneRacer™ RNA oligo (CGACUGGAGCACGAGGA-CACUGACAUGGACUGAAGGAGUAGAAA [SEQ ID NO: 33]) and the mRNA was converted to single stranded cDNA using GeneRacer™ oligo dT primer (GCTGTCAAC-GATACGCTACGTAACGGCATGACAGTG(T)18 [SEQ ID NO: 34]). After RNaseH digestion, single-stranded cDNA was subtracted once with 1 µg biotinylated polyA+ mRNA (labelled with Ambion™ BrighStar™ psoralen-biotin labelling kit) from fully expanded leaves. Hybridized RNA/cDNA was removed with Streptavidin-magnetic beads (Promega™, USA) and the cDNA was recovered by isopropanol precipitation. A fraction of the cDNA was amplified with GR5-2 (TTTTGGCGCGCCGGACACTGACTTG-GACTGAAGGAGTAGA [SEQ ID NO: 35]) and GR3-2N (TTTTTATTGCGGCCGCGCTACGTAACG-GCATGACAGTG [SEQ ID NO: 36]) primers and labeled with psoralen-biotin. The subtracted cDNA was further normalized with approximately 50 ng psoralen-biotin labeled double-stranded cDNA. After hybridization, biotinylated cDNA was removed by Streptavidin-magnetic bead and the remaining cDNA was recovered by ethanol precipitation. The cDNA was amplified by Pfu ultra DNA polymerase (Stratagen™, USA) using primers GR5-2 and GR3-2N, digested with AscI and NotI and ligated to into similarly digested pSK36 (FIG. 1; Kojima et al., 1999). The cDNA library was amplified in XL10 and transferred to *Agrobacterium tumefaciens* strain AGL1 by electroporation.

Example 2

Functional Screening of cDNA Libraries

Root transformation and cDNA library screening were carried out essentially as described by Banno et al., 2001. Approximately 100,000 transformation events were screened and four candidate calli were identified. One of the calli initially had a dark green appearance but later developed into shoots. DNA was extracted from the plantlets and cDNA inserts were recovered by amplification with Pfu DNA polymerase using primers GR5-2 and GR3-2P (TTTTTAATTAAGCTACGTAACGGCATGACAGTG [SEQ ID NO: 37]). A PCR product of approximately 1.1 Kb was generated and cloned between the AscI and PacI sites in pSK36 and pER10 (see Zou et al, 2002), respectively creating pSK36-GhCIR1 and pER10-GhCIR1. Subsequent DNA sequencing and BLAST search proved GhCIR1 is a novel gene. SEQ ID NOs: 1 and 2 show the cDNA and predicted protein sequences of GhCIR1. SEQ ID. No. 57 shows the protein encoding region (ORF) of GhCIR1

Example 3

Cloning of *Arabidopsis* At5g59340, At3g11260 and At1g46480

At5g59340 (SEQ ID NO: 3) was amplified from genomic DNA using primers 59340U (AAGGCGCGCCATG-GAAAACGAAGTAAACGCAG [SEQ ID NO: 38]) and 59340L (CGTTAATTAATTACAACCCATTACCAT-TACTATC [SEQ ID NO: 39]). The PCR products were digested with AscI and PacI and cloned into the corresponding sites in pSK36 or pER10. Its predicted protein sequence is shown in SEQ ID NO: 4. The *Arabidopsis* At3g11260 (SEQ ID NO: 5) and At1g46480 (SEQ ID NO: 7) genes were amplified by RT-PCR of total RNA extracted from young seedlings (Columbia-0) using primers 11260U (AAG-GCGCGCCAGTTGAGGACTTTACATCTGAACA [SEQ ID NO: 40]) and 11260L (AATTAATTAACCATGCATTG-GAAAATATCT [SEQ ID NO: 41]); and 46480U (AG-GCGCGCCAAAATGAAGGTTCATGAGTTTTCGAATG [SEQ ID NO: 42]) and 46480L (AGTTAATTAATCATCTC-CCTTCAGGATGGAGAGG [SEQ ID NO: 43]). The cDNA was cloned in pSK36 and pER10 between the AscI and PacI sites (FIG. 1). The DNA sequences of the clones were verified by DNA sequencing. The predicted protein sequences are shown in SEQ ID NOs: 6 and 8.

Example 4

Effects of Transient Expression of GhCIR1, At5g59340, At3g11260 and At1g46480

Root explants were transformed with pER10-GhCIR1, pER10-AtCIR1, pER10-AtCIR2 or pER10-AtESR3 by *Agrobacterium* mediated transformation. For comparison, pER10-ESR1 was also included in the experiment. The number of shoots regenerated in SR or RI medium that were with or without 10 μM estradiol were counted 3-4 weeks after co-culture. The results are summarized in Table 1. Except pER10 and pER10-At4g46480, shoots were observed in all constructs in RI medium containing inducer estradiol (RI+ medium). No shoots were seen in RI medium lacking estradiol irrespective of the constructs used. For cytokinin-independant regeneration, AtCIR2 is as efficient as ESR1, followed by GhCIR1 and AtCIR1. However, hormone and inducer contents can be individually optimized for the best regeneration result. In a normal regeneration medium supplemented with 10 μM estradiol (SR1+), the expression of GhCIR1, At5g59340 or At3g11260 causes a significant increase in the number of shoots regenerated, compared with the control vector pER10. Each of GhCIR1 and At3g11260 produced approximately 15 times more shoots than pER10 vector alone. This was about 37%-62% better than ESR1. The effect of At1g46480 was weak under the condition used. As At5g59340 and At3g11260 were able to induce shoot regeneration in the absence of cytokinins, we named them AtCIR1 (*Arabidopsis thaliana* Cytokinin Independent Regeneration 1) and AtCIR2 (*Arabidopsis thaliana* Cytokinin Independent Regeneration 1), respectively.

TABLE 1

Effects on genes on plant regeneration in *Arabidopsis* root explants

| Constructs | RI | SR | RI+ | SR+ |
|---|---|---|---|---|
| pER10 | 0 | 125 ± 15 | 0 | 87 ± 17 |
| pER10-GhCIR1 | 0 | 127 ± 12 | 65 ± 1 | 1304 ± 190 |
| pER10-At5g59340 | 0 | 116 ± 10 | 36 ± 4 | 438 ± 74 |
| pER10-At3g11260 | 0 | 122 ± 2 | 112 ± 13 | 1537 ± 375 |
| pER10-At1g46480 | 0 | 125 ± 14 | 1 ± 1 | 155 ± 16 |
| pER10-ESR1 | 0 | 109 ± 12 | 110 ± 8 | 950 ± 73 |

Note: RI+: RI medium plus 10 μM 17β-estradiol (Sigma™, USA); SR+: SR medium plus 10 μM 17β-estradiol. The number of shoots was counted on the 21st day (SR and SR+ media) and 30$^{th}$ day (RI and RI+ media). The numbers in the table are the total number of shoots per gram of root explants, averaged from three independent transformation experiments.

Example 5

Effects of Constitutive Expression of GhCIR1, At5G59340 (AtCIR1), At3g11260 (AtCIR2) in *Arabidopsis*

AGL1 carrying constructs pSK36-GhCIR1, pSK36-AtCIR1 and pSK36-ARCIR2 were used to infect *Arabidopsis* root explants, which were plated on RI or SR medium. Significantly more rapid and efficient green callus regeneration was obvious from the 7-10$^{th}$ day in SR medium. Unlike in pER10, an abundant number of shoots was also observed in RI medium. GhCIR1 and AtCIR2 were of a similar strength but AtCIR1 was significantly weaker than GhCIR1 and AtCIR2 (Table 2). While the regenerants derived from the AtCIR2 construct showed a similar morphology to those derived from the vector-only control, the shoots derived from the GhCIR1 or AtCIR1 construct mostly appeared as big clusters. Microscopic examination of the calli revealed that the shoot clusters mainly comprised germinated somatic embryos because developing roots were observed at one end and trichome-less cotyledon-like structures were observed at the other end even when cytokinin (2ip) was added in the medium (FIG. 4).

TABLE 2

|  | RI | SR |
|---|---|---|
| pSK36 | 0 | 1423 |
| pSK36-GhCIR1 | 541 | 2650 |
| pSK36-At5g59340 | 224 | 2200 |
| pSK36-At3g11260 | 762 | 2690 |

Note: The numbers in the table are the total number of shoots and dark-green calli per gram root explants on the 21$^{st}$ day (SR medium) or 30$^{th}$ day (RI medium).

Example 6

Figure 5B:
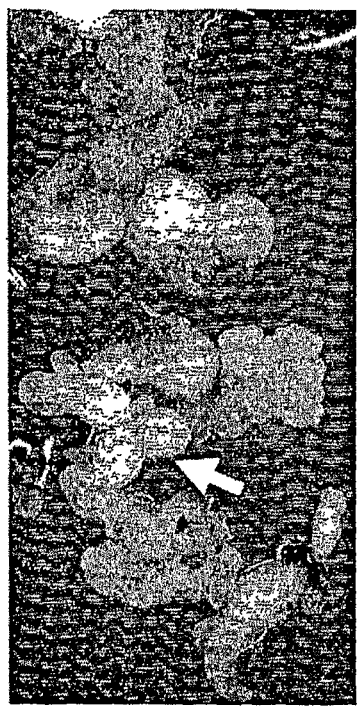

Effect of Constitutive Expression of GhCIR1 in Cotton Suspension Cultures pSK36-GhCIR1 was transformed to a cotton suspension cell culture S4 by *Agrobacterium* mediated transformation (Ji and Cai, 2004). The transformed cells were selected and regenerated in a hormone-free MS medium with 100 mg/l kanamycin and 300 mg/l Cefotaxim. Although many somatic embryos died during the regeneration process, a substantial increase in the number of somatic embryos was observed (Table 3). Embryos developed abnormally when GhCIR1 was constitutively over-expressed (FIG. 5).

TABLE 3

| Construct | Embryo No. |
|---|---|
| pSK36 | 14 |
| pSK36-GhCIR1-a | 24 |
| pSK36-GhCIR1-b | 30 |

Note: Approximately 0.2 g suspension-cultured cells were divided to 100 sectors after co-culture. The numbers in the table are the total number of the sectors that produced somatic embryos. Only viable embryos at or after globular stages were counted. pSK36-GhCIR1-a and pSK36-GhCIR1-b were two experiments of the same condition.

Example 7

GhCIR1 as a Silent Re-Useable Selection Marker

To transfer the P35S::GhCIR1 and P35S::AtCIR2 to excision vector pX6-GFP, pSk36-GhCIR1 and pSK36-AtCIR2 were digested with SpeI and the restriction site was polished with T4 DNA polymerase. The gene cassettes plus portion of the nptII gene were released by SacII digestion and ligated with SacII-ApaI digested pX6-GFP vector (the ApaI site was polished by T4 DNA polymerase). The resultant constructs were named pX6-GhCIR1 and pX6-AtCIR2, respectively. Both were introduced to *Agrobacterium* strain AGL1.

Although no transformants were observed in explants infected with pX6-GFP as a control in the RI medium without kanamycin, a large number of shoots were seen in those infected with pX6-GhCIR1 and pX6-AtCIR2. The lack of kanamycin had no significant effect on transformation efficiency. The results are summarized in Table 4.

TABLE 4

|  | RI | RI-Kan$^-$ | RI-Kan$^-$+ | SR |
|---|---|---|---|---|
| pX6-GFP | 0 | 0 | 0 | 142 ± 22 |
| pX6-GhCIR1 | 126 ± 44 | 116 ± 12 | 19 ± 4 | 1430 ± 212 |
| pX6-AtCIR2 | 374 ± 54 | 330 ± 44 | 3 ± 3 | 2349 ± 125 |

Note: RI-Kan$^-$ is the same as RI except RI contains no kanamycin. RI-Kan$^-$+ is the same as RI-Kan– except RI-Kan$^-$+ contains 10 μM 17β-estradiol. The numbers in the table are the total number of shoots per gram of root explants, averaged from three independent transformation experiments.

Example 8

Effect of Over-Expression of Truncated GhCIR1

Figure 9A:
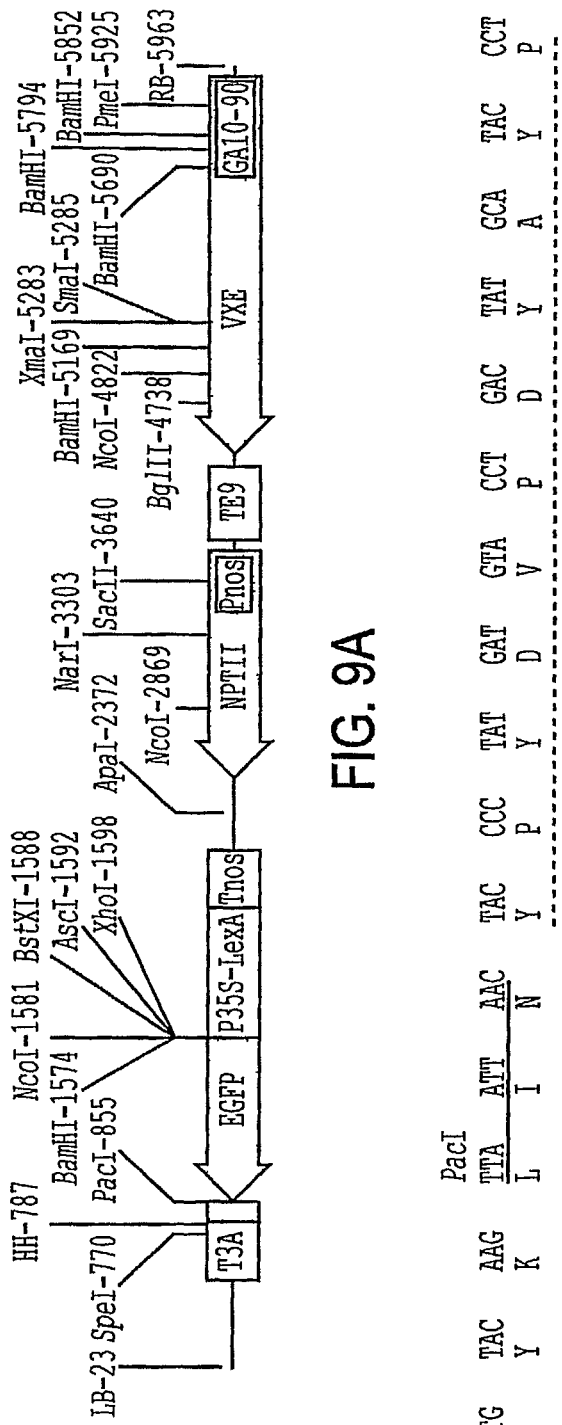
FIG. 9 shows the gene organization of the T-DNA region in pER10-EGFP-HH. Panel A shows the T-DNA region of pER10-EGFP-HH. Promoters are shown as empty boxes. Protein coding regions are shown as solid black arrows. Gene transcriptional terminators are shown as gray boxes. LB and RB define the left and right borders. Panel B shows detailed information on the double-HA-hexahistidine (HH) tag. The double HA tag is dotted-underlined and the PacI site that can be used for gene fusion is underlined (DNA sequence: SEQ ID NO: 62, polypeptide sequence: SEQ ID NO: 63).
Figure 9B:
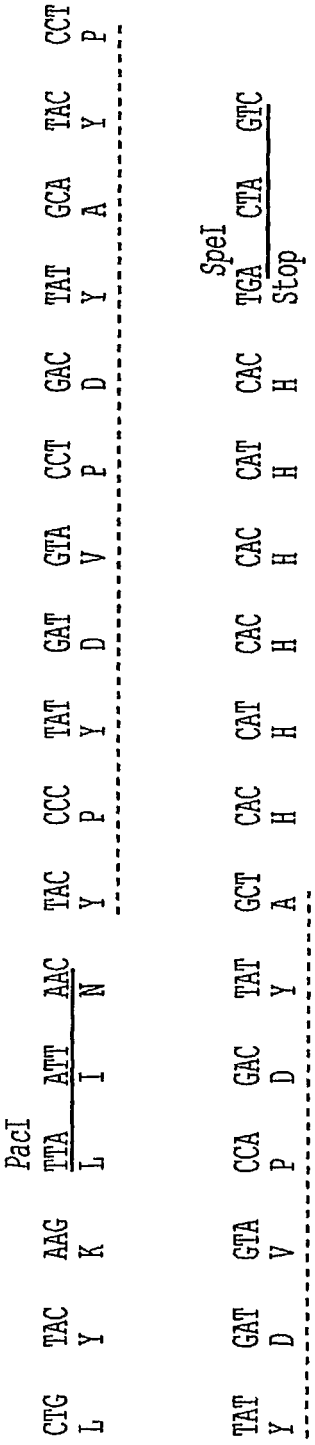

The HD and the putative activation domains of GhCIR1 were separately cloned into pER10-EGFP-HH (Ji L H, unpublished data), which contains 2×HA-6× histidine epitope tag at the C-terminus (FIG. 9). A protein of interest can be tagged by cloning in-frame of the coding region at the unique PacI site. The HD domain was amplified by primers GR5-2 and GhCIR1NL (GGTTAATTAATTGAGCTCGAT-GATGATGGT [SEQ ID NO: 44]), and the C-terminal part was amplified by primers GhCIR1CU (AAGGCGCGC-CAAAATGCCTGTTTTTCATCCTCCTCC [SEQ ID NO: 45]) and GhCIR1T (CCTTAATTAAGAAGAAATCAAT-GAAACGATGTTC [SEQ ID NO: 46]). The entire ORF was amplified by GR5-2 and GhCIR1T. All amplified fragments were digested with AscI and PacI, and cloned into the corresponding sites in pER10-EGFP-HH. The new constructs were named pER10-GhCIR1HH (the entire ORF), pER10-GhCIR1NHH (N-terminal) and pER10-GhCIR1CHH (C-terminal), respectively.

A PacI digested PCR fragment encoding the VP16 domain was amplified from pER10 using primers VP16U (CCT-TAATTAACGCCCCCCCGACCGATGTCAGCCT [SEQ ID NO: 47]) and VP16L (TTTTAATTAACCCACCG-TACTCGTCAATTCCAA [SEQ ID NO: 48]). That digested PCR fragment was then inserted at the PacI site of pER10-GhCIR1N, creating pER10-GHCIR1NVHH. The VP16 fragment was also inserted into the PacI site of pER10-GhCIR1HH, creating pER10-GhCIR1VHH.

pER10-GhCIR1HH efficiently induced shoot regeneration in RI medium as pER10-GhCIR1 does although a small drop in regeneration efficiency was observed. In contrast, no shoots were seen in root explants co-cultured with pER10-GhCIR1NHH or pER10-GhCIR1CHH. (Table 5). Moreover, addition of a VP16 activation domain to the HD domain (SEQ ID NOs: 9 and 10) did not restore the original function of GhCIR1. This suggests that the HD domain alone is insufficient for the observed functions of GhCIR1, AtCIR1 and AtCIR2.

TABLE 5

|  | RI | SR | RI+ | SR+ |
|---|---|---|---|---|
| pER10 | 0 | 769 ± 64 | 0 | 685 ± 114 |
| pER10-GhCIR1 | 0 | 800 ± 70 | 372 ± 51 | 2884 ± 148 |
| pER10-GhCIR1HH | 0 | 749 ± 81 | 187 ± 17 | 2289 ± 100 |
| pER10-GhCIR1VHH | 0 | 777 ± 52 | 97 ± 16 | 1439 ± 97 |
| pER10-GhCIR1NHH | 0 | 710 ± 58 | 0 | 684 ± 72 |
| pER10-GhCIR1NVHH | 0 | 728 ± 54 | 0 | 635 ± 96 |
| pER10-GhCIR1CHH | 0 | 820 ± 56 | 0 | 583 ± 58 |

Note: RI+: RI medium plus 10 μM estradiol; SR+: SR medium plus 10 μM estradiol. The number of shoots was counted on the 21st day (SR and SR+ media) and 30$^{th}$ day (RI and RI+ media). The numbers in the table are the total number of shoots per gram of root explants, averaged from three independent transformation experiments.

As GhCIR1 contains a basic peptide KRRGRP (SEQ ID NO: 59) (aa 138-143) that is similar to the N-terminal NLS (RKGK) (SEQ ID NO: 64) of *Agrobacterium* virD2 (Tinland et al., 1992), it is likely that the removal of the C-terminal part of GhCIR1 affects the nuclear targeting of GhCIR1N and GhCIR1N-VP16. To confirm this possibility, we created a second construct expressing a fusion protein comprising the GhCIR1N (amino acids 1-96), the VP16 activation domain and the estrogen regulatory domain that contains a nuclear localization signal (GhCIR1N-VE: SEQ ID NO: 12). This construct, pSK36-GhCIR1N-VE, was made in pSK36 and expected to simulate pER10-GhCIR1 if the fusion protein was functional. Results in Table 6 support our previous data in Table 5 as no shoot regeneration was observed in RI+ medium with this construct.

TABLE 6

|  | RI | SR | RI+ | SR+ |
| --- | --- | --- | --- | --- |
| pSK36 | 0 | 1208 | 0 | 1008 |
| pSK36-GhCIR1N-VE | 0 | 1349 | 0 | 1221 |
| pSK36-GhCIR1N | 0 | 1235 | 0 | 1028 |

Note: The numbers in the table are the total number of shoots regenerated from 1 gram of root explants.

Example 9

Root Transformation Method

Root transformation was performed according to Banno et al (2001). *Arabidopsis thaliana* Wassilewskija (WS) seeds were sterilized and sown on G medium and grown for 7 days at 22° C. under 16 hours day/night lighting cycles. Root cultures were prepared by transferring 7-day-old seedlings to B5 liquid medium and culturing for 15 days with shaking at 100 rpm. White portions of roots were excised as short explants and incubated in a callus-inducing medium (F1 medium) for 2-3 days and co-cultured in F2 medium with *Agrobacterium* strains for 2 days at 24° C. under constant lighting. After thorough washing in W solution, the root explants were suspended in SR' medium and plated on selection medium (RI, RI+, SR or SR+). The plates were sealed with Micropore™ tape (3M™) and incubated at 22° C. with 16 hours lighting cycles.

Example 10

Vital Roles of the Non-HD Domains of GhCIR1 and AtCIR2

To demonstrate the importance of the non-HD domain of the encoded polypeptides disclosed herein, we created chimeric constructs of GhCIR1 and AtCIR2. pER10-GhCIR1N2HH (encoding aa 1-147 of GhCIR1) was made inserting AscI-PacI digested PCR product of primers GR5-2 and GhCIR1N2L (GATTAATTAAAGTTTTACCAATAG-GCCTGC) (SEQ ID NO: 49) into the corresponding sites of pER10-GhCIR1HH. GhCIR1N1C2 is a fusion of HD-domain of GhCIR1 (aa 1-93) and the C-terminal domain (C2 fragment) of AtCIR2 (aa 107-192) and was made by inserting a PacI-digested PCR product of primers At3g11260U2 (TTT-TAATTAATCCATCAACTAGAGATGTTTTTG) (SEQ ID NO: 50) and At3g11260L (AATTAATTAACCATGCATTG-GAAAATATCT) (SEQ ID NO: 41) into the PacI site of pER10-GhCIR1N1HH. Similarly, pER10-GhCIR1N2C2 was made by inserting the C2 fragment into the PacI site of pER10-GhCIR1N2HH. The ORF of GhCIR1N2C2 (SEQ ID. 58). pER10-GhCIR1N1C2 and pER10-GHCIR1N2HH were similar to the empty vector pER10 in inducing cytokinin-independent shoot regeneration or improving transformation efficiency in the presence of cytokinin, i.e., pER10-GhCIR1N1C2 or pER10-GhCIR1N2HH did not show any activity in inducing cytokinin-independent shoot regeneration or improving transformation efficiency in the presence of cytokinin. pER10-GhCIR1N2C2, however, not only improved transformation efficiency in the presence of 2ip (cytokinin) but also induced shoot regeneration in the absence of 2ip (cytokinin) (Table 7). An interesting difference between pER10-GhCIR1N1C2 and pER10-GhCIR1N2C2 (compare SEQ ID NOs:14 and 16) is a short motif KRRGRP (SEQ ID NO: 59) resembling the monopartite nuclear localization signal (Tinland et al., 1992). Therefore, this motif may serve as a nuclear targeting signal in GhCIR1 and GhCIR1N2C2.

The C-termini of GhCIR1, AtCIR1 and AtCIR2 all contain a conserved hexapeptide with a consensus sequence of TLx-LFP (SEQ ID NO: 65) near the C-terminal ends. This peptide is not found in other proteins except Wuschel-related HD-domain proteins. We noticed the presence of a threonine residue in the peptide. To see if phosphorylation of this residue has any effect on the function of Wuschel-related proteins, threonine 188 ($T^{188}$) of GhCIR1 was mutated by site-directed mutagenesis to encode either aspartic acid (D) that mimics phosphorylation, or alanine (A) that is resistant to phosphorylation. Primer pairs GR5-2 (SEQ ID NO: 35)/GhCIR1T188AU (SEQ ID NO: 51) and GhCIR1T188AL (SEQ ID NO:52)/GR3-2P (SEQ ID NO: 37) were used for amplification of 5' and 3' parts of GhCIR1T188A, respectively, which were joined by PCR using primer pair GR-5-2/GR3-2P and cloned in pER10-EGFP-HH. pER10-GhCIR1T188D was similarly made using primers GhCIR1T188DU (SEQ ID NO: 53) and GhCIR1T188DL (SEQ ID NO: 54).

Strikingly, mutant GhCIR1$T^{188}$D totally lost its function to enhance transformation in the presence of 2ip or induce shoot regeneration in the absence of Zip while GhCIR1$T^{188}$A was only marginally weakened compared to the wild-type GhCIR1 (Table 7). These findings suggest that a non-phosphorylated TLxLFP (SEQ ID NO: 65) motif is vital for functions of the Wuschel-related proteins. Therefore, the threonine residue in this hexapeptide may be substituted by non-negatively charged amino acids, and substitution by a negatively charged amino acid, i.e., aspartic acid (D) or glutamic acid (E)) is not favored. Preferably the non-negatively charged amino acids are neutral amino acids, e.g., alanine, cysteine, methionine, isoleucine, leucine, valine, proline, glycine, phenylalanine and tryptophan. More preferably the non-negatively charged amino acids are phosphorylation-resistant amino acids with simple side chains, e.g. alanine, glycine, methionine, valine, isoleucine, leucine. The most preferred non-negatively charged amino acid is alanine.

As GhCIR1 loses its cytokinin-independent shoot regeneration activity by the phosphorylation of $T^{188}$, it can be inferred that over-expression of theonine/serine phosphatase will have a similar effect as over-expression of GhCIR1. An example of such phosphatases is one encoded by the *arabidopsis* Poltergeist (Pol) gene (Yu et al, 2003). Preferably, phosphatase mutants with deleted negative regulation domain are to be over-expressed.

A detailed examination of sequence alignment of Wuschel-related proteins (FIGS. 2A-C) revealed that the TLxLFP (SEQ ID NO: 65) motif is followed by only 3 amino acids in At1g46480 compared to 48 amino acids in GhCIR1, 55 amino acids in AtCIR1 and 54 amino acids in AtCIR2. To see if the lack of significant sequence extension accounted for the virtual lack of the cytokinin-independent shoot regeneration function of At1g46480, the C-terminal 45 amino acids of GhCIR1 was deleted by PCR using primers GR5-2 and GhCIR1Δ45L (TTAATTAAAACACCAGTCGGGTG-CAATG) (SEQ ID NO: 55). Indeed, this construct, pER10-GhCIR1Δ43HH, contained only negligible activity in promoting shoot regeneration or cytokinin-independent shoot regeneration (Table 7). In addition, we noticed that a glutamic acid is conserved in GhCIR1, AtCIR1 and AtCIR2 in deleted region. However, converting this residue to alanine, which was achieved by one-step PCR using primers GR5-2 and GhCIR1E236AL (TTTTAATTAAGAAGAAATCAAT-GAAACGATGTGCCCCAGAA) (SEQ ID NO: 56), did not change the activity of GhCIR1 (Table 7, pER10-GhCIR1E236AHH). This result indicates that the size of this highly degenerate region is vital for both cytokinin-independent shoot regeneration and transformation enhancing activities.

TABLE 7

| Construct | RI | SR | RI+ | SR+ |
|---|---|---|---|---|
| pER10 | 0 | 417 ± 83 | 0 | 293 ± 51 |
| pER10-GhCIR1HH | 0 | 507 ± 74 | 354 ± 45 | 1905 ± 615 |
| pER10-GhCIR1N1HH | 0 | 463 ± 85 | 0 | 327 ± 15 |
| pER10-GhCIR1N1VHH | 0 | 417 ± 201 | 0 | 220 ± 50 |
| pER10-GhCIR1N1C2 | 0 | 447 ± 124 | 0 | 410 ± 40 |
| pER10-GHCIR1N2HH | 0 | 370 ± 46 | 0 | 297 ± 107 |
| pER10-GhCIR1N2VHH | 0 | 395 ± 65 | 0 | 273 ± 85 |
| pER10-GhCIR1N2C2 | 0 | 570 ± 50 | 130 ± 20 | 1727 ± 196 |
| pER10-GhCIR1CHH | 0 | 493 ± 183 | 0 | 245 ± 55 |
| pER10-GhCIR1T$^{188}$AHH | 0 | 407 ± 125 | 217 ± 76 | 2040 ± 478 |
| pER10-GhCIR1 T$^{188}$DHH | 0 | 523 ± 182 | 0 | 317 ± 100 |
| pER10-GHCIR1D43HH | 0 | 537 ± 86 | 7 ± 6 | 563 ± 76 |
| pER10-GhCIR1E236AHH | 0 | 490 ± 95 | 400 ± 41 | 2075 ± 400 |

Note: RI+: RI medium plus 10 μM estradiol; SR+: SR medium plus 10 μM estradiol. The number of shoots was counted on the 21st day (SR and SR+ media) and 30$^{th}$ day (RI and RI+ media). The numbers in the table are the total number of shoots per grain of root explants, averaged from three independent transformation experiments.

Example 11

Signature Sequence of Cytokinin-Independent Regeneration Proteins

From analysis of FIGS. 2A-C and data presented in Table 1, 2, 5 and 7, we concluded that functional proteins contained a C-terminal extension of about 50-60 residues (50 aa in GhCIR1, 57 aa in AtCIR1 and 52 aa in AtCIR2) whereas non-functional proteins had less than 12 aa in the C-terminal extension (12 aa in PRS, 5 aa in At1 g46480 and GhCIR1Δ45C). We also have found that GhCIR1, AtCIR1 and AtCIR2, which have cytokinin-independent shoot regeneration activity, share common elements including 1) a homeodomain near the N-terminus, 2) a nuclear localization signal (NLS), 3) a hexapeptide TLxLFP (SEQ ID NO: 65) that may be subjected to negative regulation by phosphorylation near the C-terminus and 4) a C-terminal extension to the TLxLFP (SEQ ID NO: 65) hexapeptide. These findings can be extrapolated into a signature sequence. A NLS sequence is not shown at any specific position in the signature sequence since it can be located anywhere in a protein as long as it does not disrupt the homeodomain near the N-terminus and the hexapeptide TLxLFP (SEQ ID NO: 65) near the C-terminus and is preferably exposed on the surface of the folded protein so as to be recognized by the cellular nuclear importing machinery.

A signature sequence for a protein that is able to enhance plant transformation and cytokinin-independent regeneration is defined as follows:

(SEQ ID NO: 60)
(X$^{13-23}$)RWNPT(KV)(DE)Q(IL)(STK)(MIL)L(ET)(SND)L (FY)(KR)(QEA)G(IL)RTP(ST)(AT)DQIQ(QK)I(ST)(GST)

(RE)L(KRS)(AF)YG(KHT)IE(GS)KNVFYWFQNHKAR(QE)RQK (QR)(KR)(X$^{29-101}$)(EK)(STACIGVLMNQP)L(PQ)LFP(LV)

(X$^{13-57}$)

wherein
X represents any amino acids and the numbers following the X represent the range of the size of the domain represented by X,
amino acids in a bracket represent alternatives for that position, for example, RWNPT(KV) (SEQ ID NO: 66) means that RWNPTK (SEQ ID NO: 67) or RWNPTV (SEQ ID NO: 68), and the protein comprises an NLS with the proviso that the NLS does not change the specified amino acids, excluding prior art sequences such as AtCIR2 and AtCIR1.

It is well known that a protein sequence could have been evolved considerably without changing its function. Various mathematical matrices have been made to define the weight of amino acid similarity. Today the most commonly used matrix for sequence alignment and homology search, e.g., BLAST search, is the BLOSUM series of matrices (Henikoff and Henikoff, 1992). Among them, BLOSUM 62 is often the default matrix for BLAST search. This mathematical model may be used for in silico evolution of the signature sequence that was described above. By substituting the less conserved positions with conserved residues that weigh at least one in the BLOSUM 62 substitution table, the signature sequence for a protein that is able to enhance plant transformation and cytokinin-independent regeneration may be expanded as follows.

(SEQ ID NO: 61)
(X$^{13-23}$)RWNPT(KEQRIMLV)(EDNKQ)Q(ILMV)(EKNSTQR)

(MILV)L(DEKQST)(ADEHNST)L(FYW)(EQKR)(ADEKRQS)G (ILMV)RTP(AST)(AST)DQIQ(EKQR)I(AST)(AGST)(DEKQR)L (AEQKRST)(ASFWY)YG(EQHKTY)IE(AGST)KNVFYWFQNHKAR (DEQKR)RQK(EKQR)(EQKR)(X$^{29-101}$)(DEKQR)

(STACIGVLMNQP)L(EPQKR)LFP(MILV)(X$^{13-57}$), wherein
X represents any amino acids and the numbers following the X represent the range of the size of the domain represented by X,
amino acids in a bracket represent alternatives for that position, for example, RWNPT(KV) (SEQ ID NO: 66) means that RWNPTK (SEQ ID NO: 67) or RWNPTV (SEQ ID NO: 68), and
the protein comprises an NLS with the proviso that the NLS does not change the specified amino acids, excluding prior art sequences such as AtCIR2. It is also well known that a polypeptide, e.g., β-galactosidase (LacZ), green florescent protein (GFP), β-glucuronidase (GUS), etc, may be inserted into a protein to form a fusion protein without substantial changes in the protein's activity. Therefore, insertion of one or more of heterogeneous sequences in the signature sequence and/or addition to the signature sequence at the X domains is also contemplated with the proviso that such insertion does not change the specified amino acids.

Example 12

Effect of Constitutive Expression of GhCIR1 and AtCIR2 in Cotton Root Explants

To further demonstrate that GhCIR1 enhances transformation efficiency in cotton, pX6-GhCIR1 was used to transform cotton root explants. Surface sterilized cotton seeds (Coker 312) were germinated in half-strength, sugar-free MS medium. Root explants of about 1 cm in length were pre-cultured for 3 days at 28° C. in MS medium supplemented with 0.1 mg/l kenetin and 0.1 mg/l 2,4-D. *Agrobacterium* culture (AGL1) harboring pX6-GhCIR1 or pEX6-GFP was washed and adjusted to about 0.3 $OD_{600}$ units in MS medium supplemented 0.1 mg/l kenetin, 0.1 mg/l 2,4-D and 100 μM acetosyringon. Pre-cultured root explants were soaked in the AGL1 suspensions for about 10 minutes. After briefly blotted dry in filter paper, the root explants were cultured at 28° C. on solid MS medium supplemented with 1 mg/l zeatin riboside, 0.01 mg/l NAA, 100 mg/l kanamycin and 300 mg/l Cefotaxime. The number of kanamycin resistant calli at the end of the second month are scored and summarized in Table 8. In two independent experiments, over-expression of GhCIR1 lead to 2.3-fold and 4-fold more transformed calli, respectively. Furthermore, pX6-GhCIR1 calli were 2-3 times larger than the empty vector.

TABLE 8

|  | $Kan^r$ Calli | Total Explants | Transformation efficiency |
|---|---|---|---|
| Experiment 1 construction |  |  |  |
| pX6 | 13 | 465 | 3 |
| pX6-CIR1 | 44 | 642 | 7 |
| Experiment 2 construction |  |  |  |
| pX6 | 9 | 416 | 2 |
| pX6-CIR1 | 54 | 695 | 8 |

Note: Transformation efficiency is calculated as the percentage of kanamycin resistant calli over total number of explants used for co-cultured with Agrobacterium strains.

Thus, one aspect of the present invention relates to an isolated polynucleotide comprising SEQ ID NO: 1. Another aspect of the present invention relates to an isolated polynucleotide comprising SEQ ID NO: 15. Another aspect of the present invention relates to an isolated polynucleotide comprising a polynucleotide of at least 65% identity to SEQ ID NO: 1 wherein the polypeptide encoded by the polynucleotide promotes plant regeneration, induces plant regeneration in the absence of exogenous hormones, or increases plant transformation efficiency. Another aspect of the present invention relates to an isolated polynucleotide comprising a polynucleotide of at least 65% identity to SEQ ID NO: 15 wherein the polypeptide encoded by the polynucleotide promotes plant regeneration, induces plant regeneration in the absence of one or more exogenous hormones, or increases plant transformation efficiency. Another aspect of the present invention relates to an isolated polynucleotide comprising a polynucleotide encoding SEQ ID NO: 2. Another aspect of the present invention relates to an isolated polynucleotide comprising a polynucleotide encoding SEQ ID NO: 16. Another aspect of the present invention relates to an isolated polynucleotide comprising a polynucleotide encoding a polypeptide that promotes plant regeneration, induces plant regeneration in the absence of one or more exogenous hormones, or increases plant transformation efficiency. The polypeptide preferably contains a signatures sequence:

```
                                          (SEQ ID NO: 61)
(X^13-23) RWNPT(KEQRIMLV)(EDNKQ)Q(ILMV)(EKNSTQR)

(MILV)L(DEKQST)(ADEHNST)L(FYW)(EQKR)(ADEKRQS)G (ILMV)RTP(AST)(AST)DQIQ(EKQR)I(AST)(AGST)(DEKQR)L (AEQKRST)(ASFWY)YG(EQHKTY)IE(AGST)KNVFYWFQNHKAR (DEQKR)RQK(EKQR)(EQICR)(X^29-101)(DEKQR)

(STACIGVLMNQP)L(EPQKR)LFP(MILV)(X^13-57),
``` wherein

X represents any amino acids and the numbers following the X represent the range of the size of the domain represented by X, amino acids in a bracket represent alternatives for that position, for example, RWNPT(KV) (SEQ ID NO: 66) means that RWNPTK (SEQ ID NO: 67) or RWNPTV (SEQ ID NO: 68), and the protein comprises an NLS with the proviso that the NLS does not change the specified amino acids and the protein excludes prior art sequences such as AtCIR2. A preferred signature sequence is

```
                                          (SEQ ID NO: 60)
(X^13-23) RWNPT(KV)(DE)Q(IL)(STK)(MIL)L(ET)(SND)L (FY)(KR)(QEA)G(IL)RTP(ST)(AT)DQIQ(QK)I(ST)(GST)

(RE)L(KRS)(AF)YG(KHT)IE(GS)KNVFYWFQNHKAR(QE)RQK (QR)(KR)(X^29-101)(EK)(STACIGVLMNQP)L(PQ)LFP(LV)

(X^13-57),
``` wherein

X represents any amino acids and the numbers following the X represent the range of the size of the domain represented by X, amino acids in a bracket represent alternatives for that position, for example, RWNPT(KV) (SEQ ID NO: 66) means that RWNPTK (SEQ ID NO: 67) or RWNPTV (SEQ ID NO: 68), and the protein comprises an NLS with the proviso that the NLS does not change the specified amino acids and the protein excludes prior art sequences such as AtCIR2. Further, insertion of one or more of heterogeneous sequences such as reporter enzymes, e.g., beta-galactosidase (LacZ), green florescent protein (GFP), beta-glucuronidase (GUS), etc, in the signature sequence and/or addition to the signature sequence at the X domains is also contemplated with the proviso that such insertion does not change the specified amino acids.

The isolated polynucleotides may comprise an operably linked promoter active in a plant. The promoter may be an inducible or constitutive promoter. The isolated polynucleotides may comprise other regulatory regions such as an enhancer, or a repressor binding site. The isolated polynucleotides may comprise fusion partners for various purposes such as over expression, increased stability, targeting to a specific type of cells or intracellular compartments, or tagging for easier identification or purification. The isolated polynucleotide may be a gene. The isolated polynucleotide may be a vector, or when the isolated polynucleotide is a gene, the polynucleotide may be incorporated into a vector. The vector can be a plasmid. The isolated polynucleotide may be an expression vector, or when it is a gene, it can be incorporated into an expression vector so that the polypeptide encoded by the isolated polynucleotide can be produced in a cell, preferably bacterial cell, plant cell, or both. The present invention also relates to a cell that has been transformed (transformed in a broad sense, including transformation, transduction, transfection and conjugation) with the isolated polynucleotide or when the isolated polynucleotide is a gene, the gene or a vector incorporating the gene. The transformed cells may further comprise a second vector. The first and second vector may comprise a binary vector system.

Another aspect of the present invention relates to an isolated polypeptide comprising SEQ ID NO: 2. Another aspect of the present invention relates to an isolated polypeptide comprising SEQ ID NO: 16. Another aspect of the present invention relates to an isolated polypeptide of at least 65% identity to SEQ ID NO: 2, wherein said polypeptide promotes plant regeneration, induces plant regeneration in the absence of exogenous hormones, or increases plant transformation efficiency. Another aspect of the present invention relates to an isolated polypeptide of at least 65% identity to SEQ ID NO: 16, wherein said polypeptide promotes plant regeneration, induces plant regeneration in the absence of exogenous hormones, or increases plant transformation efficiency. Another aspect of the present invention relates to an isolated polypeptide that promotes plant regeneration, induces plant regeneration in the absence of exogenous hormones, or increases plant transformation efficiency. The polypeptide preferably contains a signatures sequence:

(SEQ ID NO: 61)
($X^{13-23}$)RWNPT(KEQRIMLV)(EDNKQ)Q(ILMV)(EKNSTQR)

(MILV)L(DEKQST)(ADEHNST)L(FYW)(EQKR)(ADEKROS)G (ILMV)RTP(AST)(AST)DQIQ(EKQR)I(AST)(AGST)(DEKQR)

L(AEQKRST)(ASFWY)YG(EQHKTY)IE(AGST)KNVFYWFQNHKAR (DEQKR)RQK(EKQR)(EQKR)($X^{29-101}$)(DEKQR)(STACIGVLM

NQP)L(EPQKR)LFP(MILV)($X^{13-57}$), wherein
X represents any amino acids and the numbers following the X represent the range of the size of the domain represented by X,
amino acids in a bracket represent alternatives for that position, for example, RWNPT(KV) (SEQ ID NO: 66) means that RWNPTK (SEQ ID NO: 67) or RWNPTV (SEQ ID NO: 68), and
the protein comprises an NLS with the proviso that the NLS does not change the specified amino acids and the protein excludes prior art sequences such as AtCIR2. A more preferred signature sequence is (SEQ ID NO: 60)
($X^{13-23}$)RWNPT(KV)(DE)Q(IL)(STK)(MIL)L(ET)(SND)L (FY)(KR)(QEA)G(IL)RTP(ST)(AT)DQIQ(QK)I(ST)(GST)

(RE)L(KRS)(AF)YG(KHT)IE(GS)KNVFYWFQNHKAR(QE)RQK (QR)(KR)($X^{29-101}$)(EK)(STACIGVLMNQP)L(PQ)LFP(LV)

($X^{13-57}$), wherein
X represents any amino acids and the numbers following the X represent the range of the size of the domain represented by X,
amino acids in a bracket represent alternatives for that position, for example, RWNPT(KV) (SEQ ID NO: 66) means that RWNPTK (SEQ ID NO: 67) or RWNPTV (SEQ ID NO: 68), and the protein comprises an NLS with the proviso that the NLS does not change the specified amino acids and the protein excludes prior art sequences such as AtCIR2. Further, insertion of one or more of heterogeneous sequences such as reporter enzymes, e.g., beta-galactosidase (LacZ), green florescent protein (GFP), beta-glucuronidase (GUS), etc, in the signature sequence and/or addition to the signature sequence at the X-domains is also contemplated with the proviso that such insertion does not change the specified amino acids.

Another aspect of the present invention relates to a method of selecting a polynucleotide that enhances plant regeneration from non-Arabidopsis mRNAs comprising the steps of constructing a cDNA library from cells, wherein the cDNAs in said cDNA library can be optionally normalized and are regulated by a plant-active promoter; transforming *Arabidopsis* explants with vectors comprising said normalized cDNA library; culturing said *Arabidopsis* explants in a plant-cell-culture medium that is non-supportive of plant regeneration with conventional vectors, wherein said plant-cell-culture medium can be free of one or more plant hormones or with only trace amount of them; selecting *Arabidopsis* explants regenerating in said plant-cell-culture medium; identifying the nucleotide sequence of the polynucleotide that was transferred from said cDNA library to said *Arabidopsis* explants regenerating in said plant-cell-culture medium and makes said *Arabidopsis* explants regenerate in said plant-cell-culture medium by sequencing a PCR product amplified from said *Arabidopsis* explants regenerating in said plant-cell-culture medium using a primer from a group consisting of SEQ ID NOs. 35, 37, 38, 39, 40, 41, 42 and 43; and isolating a polynucleotide of said nucleotide sequence from a cell, or synthesizing a polynucleotide of said nucleotide sequence.

Another aspect of the present invention relates to a method of selecting a plant cell transformant comprising the steps of transforming plant cells with vectors, wherein said vector comprises the isolated polynucleotide described above, and a promoter that is active in a plant and operably linked to said isolated polynucleotide; culturing said plant cells in a plant-cell-culture medium that is non-supportive of plant regeneration with conventional vectors; and selecting regenerating plant cells. The vector may further comprise a polynucleotide of interest.

Another aspect of the present invention relates to a method of improving plant transformation efficiency comprising the steps of transforming plant cells with vectors, wherein said vector comprises the isolated polynucleotide described above, and a promoter that is active in a plant and operably linked to said isolated polynucleotide; culturing said plant cells in a plant-cell-culture medium that is optionally cytokinin-free; and selecting regenerating plant cells.

Another aspect of the present invention relates a method for improving plant regeneration or transformation efficiency by over-expression of a theonine/serine phosphatase in vectors, wherein said vector comprises the isolated theonine/serine phosphatase gene or unregulated mutants of the genes, and a promoter that is active in a plant and operably linked to said isolated genes; culturing said plant cells in a plant-cell-culture medium that is optionally free of cytokinins; and selecting regenerating plant cells. The serine/threonine phosphatase is preferably the one encoded by *arabidopsis* Poltergeist (Pol) gene (Yu et al, 2003). The serine/threonine phosphatase polypeptide can be one sharing at least 65% identity with the *arabidopsis* Poltergeist. Preferably, phosphatase mutants with deleted negative regulation domain are to be over-expressed.

It will be appreciated that the polynucleotides of the present invention may be used to induce plant regeneration in the absence of one or more exogenous hormones as well as promote plant regeneration, or increase plant transformation efficiency using a normal regeneration or transformation methods.

The transformation of a cell, including a cell comprising explants, with the isolated polynucleotide of the present invention (in other words, the incorporation or transfer of the isolated polynucleotide of the present into a cell) can be achieved by a method well known one skilled in the art. Especially for a plant cell, such a transformation can be achieved by *Agrobacterium*-mediated T-DNA conjugation or particle gun bombardment.

A wide variety of plant cells can be used to practice the present invention. Particularly preferred are *Arabidopsis* and cotton; however, rice, corn (e.g. maize), beans (e.g. soybeans), wheat, barley, sugarbeet, oil palm, sunflower and others can also be used. A wide variety of plant cells can be used to practice the present invention. Preferred are explants from various origins, and especially, root explants are preferred in selecting a polynucleotide that enhances plant regeneration.

A wide variety of promoters can be used to practice the present invention. For a vector to transfer the isolated polynucleotide between two different hosts, two separate promoters, respectively active only in one of the two hosts, can be used. The promoter can be a chemically inducible promoter, or a constitutive promoter. The isolated polynucleotide and promoter may be chemically excisable.

The plant-cell-culture medium used to practice the present invention may be free of any antibiotics or herbicides, or any plant hormones.

The invention also contemplates a complement sequence of any of the nucleic acid sequences disclosed above; the use of the complement sequences in producing the nucleic acid sequences disclosed above in a biological system; and the use of the complement sequences in probing nucleic acid sequences related to the sequences disclosed above.

Therefore, the invention can be embodied in the following ways.
1. An isolated polynucleotide comprising
   a. SEQ ID NOs: 57 or 15; or a complement thereof;
   b. a polynucleotide of at least 65% identity to SEQ ID NOs: 57 or 15; or a complement thereof, wherein the polypeptide encoded by the polynucleotide of at least 65% identity to SEQ ID NOs: 57 or 15; or a complement thereof promotes plant regeneration, induces plant regeneration in the absence of one or more exogenous hormones, or increases plant transformation efficiency;
   c. a polynucleotide encoding SEQ ID NOs: 2 or 16; or a complement thereof;
   d. a polynucleotide encoding a polypeptide comprising a signature sequence:

(SEQ ID NO: 61)
$(X^{13-23})$ RWNPT (KEQRIMLV) (EDNKQ) Q (ILMV) (EKNSTQR)

(MILV) L (DEKQST) (ADEHNST) L (FYW) (EQKR) (ADEKRQS) G (ILMV) RTP (AST) (AST) DQIQ (EKQR) I (AST) (AGST) (DEKQR)

L (AEQKRST) (ASFWY) YG (EQHKTY) IE (AGST) KNVFYWFQNHKAR (DEQKR) RQK (EKQR) (EQKR) $(X^{29-101})$ (DEKQR) (STACIGVLM

NQP) L (EPQKR) LFP (MILV) $(X^{13-57})$ , wherein
  X represents any amino acids,
  the numbers following the X represent the range of the size of the domain represented by X,
  amino acids in each bracket represent alternatives for the respective single amino acid position represented by each bracket,
  the polypeptide comprises an NLS with the proviso that the NLS does not change the specified amino acids, and
  AtCIR1 and AtCIR2 are excluded from the polypeptide comprising the signature sequence.
2. The isolated polynucleotide of item 1, further comprising an operably linked promoter, wherein said promoter is active in a plant.
3. The isolated polynucleotide of item 1, wherein said isolated polynucleotide is a gene.
4. The isolated polynucleotide of item 2, wherein said promoter is a constitutive promoter.
5. The isolated polynucleotide of item 2, wherein said promoter is an inducible promoter.
6. A vector which comprises the polynucleotide of item 1.
7. The vector of item 6, wherein said vector is a plasmid.
8. The vector of item 6, further comprising a promoter, wherein said promoter is operably linked to said polynucleotide.
9. The vector of item 8, wherein said promoter is active in a plant cell.
10. A binary vector system comprising the vector of item 9.
11. A bacterial cell comprising the vector of 7.
12. A plant cell comprising the vector of 9.
13. The isolated polynucleotide of item 1, wherein the signature sequence is (SEQ ID NO: 60)
$(X^{13-23})$ RWNPT (KV) (DE) Q (IL) (STK) (MIL) L (ET) (SND) L (FY) (KR) (QEA) G (IL) RTP (ST) (AT) DQIQ (QK) I (ST) (GST)

(RE) L (KRS) (AF) YG (KHT) IE (GS) KNVFYWFQNHKAR (QE) RQK (QR) (KR) $(X^{29-101})$ (EK) (STACIGVLMNQP) L (PQ) LFP (LV)

$(X^{13-57})$ .

14. The nucleotide of item 1, wherein the polypeptide comprises an additional sequence in the signature sequence at the X domains.
15. An isolated polypeptide comprising
   a. SEQ ID NOs: 2 or 16;
   b. a polypeptide of at least 65% identity to SEQ ID NOs: 2 or 16, wherein the polypeptide of at least 65% identity to SEQ ID NOs: 2 or 16 promotes plant regeneration, induces plant regeneration in the absence of one or more exogenous hormones or in a trace amount of them, or increases plant transformation efficiency;
   c. a signature polypeptide:

(SEQ ID NO: 61)
$(X^{13-23})$ RWNPT (KEQRIMLV) (EDNKQ) Q (ILMV) (EKNSTQR)

(MILV) L (DEKQST) (ADEHNST) L (FYW) (EQKR) (ADEKRQS) G (ILMV) RTP (AST) (AST) DQIQ (EKQR) I (AST) (AGST) (DEKQR)

L (AEQKRST) (ASFWY) YG (EQHKTY) IE (AGST) KNVFYWFQNHKAR (DEQKR) RQK (EKQR) (EQKR) $(X^{29-101})$ (DEKQR) (STACIGVLM

NQP) L (EPQKR) LFP (MILV) $(X^{13-57})$ ,

X represents any amino acids, the numbers following the X represent the range of the size of the domain represented by X, amino acids in each bracket represent alternatives for the respective single amino acid position represented by each bracket, the polypeptide comprises an NLS with the proviso that the NLS does not change the specified amino acids, and AtCIR1 and AtCIR2 are excluded from the polypeptide comprising the signature sequence.

16. The isolated polypeptide of item 15, wherein the signature sequence is preferably (SEQ ID NO: 60)
$(X^{13-23})$RWNPT(KV)(DE)Q(IL)(STK)(MIL)L(ET)(SND)L (FY)(KR)(QEA)G(IL)RTP(ST)(AT)DQIQ(QK)I(ST)(GST)

(RE)L(KRS)(AF)YG(KHT)IE(GS)KNVFYWFQNHKAR(QE)RQK (QR)(KR)$(X^{29-101})$(EK)(STACIGVLMNQP)L(PQ)LFP(LV)

$(X^{13-57})$.

17. The isolated polypeptide of item 16, wherein the isolated polypeptide comprises an additional sequence in the signature sequence at the X domains.

18. A method of selecting a polynucleotide from species other than *Arabidopsis*, comprising the steps of
   a. constructing a cDNA library from cells, wherein the cDNAs in said cDNA library can be expressed in a plant cell,
   b. transforming *Arabidopsis* explants with vectors in said cDNA library,
   c. culturing said *Arabidopsis* explants in a plant-cell-culture medium that is non-supportive of regeneration with conventional vectors,
   d. selecting *Arabidopsis* explants regenerating in said plant-cell-culture medium,
   f. identifying the nucleotide sequence of the polynucleotide that was transferred from said cDNA library to said *Arabidopsis* explants regenerating in said plant-cell-culture medium and enables said *Arabidopsis* explants to regenerate in said plant-cell-culture medium, and
   g. isolating a polynucleotide of said nucleotide sequence from a cell, or synthesizing a polynucleotide of said nucleotide sequence.

19. The method of item 18, wherein *Arabidopsis* explants are transformed with said vectors in said cDNA library by *Agrobacterium*-mediated T-DNA conjugation.

20. The method of item 18, wherein *Arabidopsis* explants are transformed with said vectors in said cDNA library by particle gun bombardment 21. The method of item 18, wherein said plant-cell-culture medium does not contain no cytokinins or trace amount of cytokinins.

22. The method of item 18, wherein said plant-cell-culture medium does not contain 2ip.

23. The method of item 18, wherein said *Arabidopsis* explants are *Arabidopsis* root explants.

24. A method of selecting a plant cell transformant comprising the steps of
   a. transforming plant cells with vectors, wherein said vector comprises
      i. a polynucleotide encoding a polypeptide that enables a transformant to regenerate in a medium deficient of one or more hormones, and
      ii. a promoter that is active in a plant and operably linked to said isolated polynucleotide,
   b. culturing said plant cells in a plant-cell-culture medium that is deficient of one or more hormones, and
   c. selecting regenerating plant cells.

25. The method of item 24, wherein the polypeptide that enables a transformant to regenerate in said medium is
   a. a polypeptide of at least 65% identity to SEQ ID NOs: 2 or 16; or
   b. a signature polypeptide:

(SEQ ID NO: 61)
$(X^{13-23})$RWNPT(KEQRIMLV)(EDNKQ)Q(ILMV)(EKNSTQR)

(MILV)L(DEKQST)(ADEHNST)L(FYW)(EQKR)(ADEKRQS)G (ILMV)RTP(AST)(AST)DQIQ(EKQR)I(AST)(AGST)(DEKQR)

L(AEQKRST)(ASFWY)YG(EQHKTY)IE(AGST)KNVFYWFQNHKAR (DEQKR)RQK(EKQR)(EQKR)$(X^{29-101})$(DEKQR)(STACIGVLM

NQP)L(EPQKR)LFP(MILV)$(X^{13-57})$,

X represents any amino acids, the numbers following the X represent the range of the size of the domain represented by X, amino acids in each bracket represent alternatives for the respective single amino acid position represented by each bracket, and the polypeptide comprises an NLS with the proviso that the NLS does not change the specified amino acids.

26. The method of item 24, wherein said vector further comprises a polynucleotide of interest.

27. The method of item 24, wherein said promoter is a chemically inducible promoter.

28. The method of item 24, wherein said promoter is a constitutive promoter.

29. The method of item 24, wherein said isolated polynucleotide and promoter are chemically exicisable.

30. The method of item 24, wherein said plant-cell-culture medium does not contain any antibiotics or herbicides.

31. The method of item 24, wherein said plant-cell-culture medium does not contain one or more hormones.

32. A method of improving plant transformation efficiency comprising the steps of
   a. transforming plant cells with vectors, wherein said vector comprises:
      i. a polynucleotide encoding a polypeptide that enables a transformant to regenerate in a medium that is deficient of one or more hormones or increases regeneration rate in a regular plant-cell-culture medium, and
      ii. a promoter that is active in a plant and operably linked to said isolated polynucleotide,
   b. culturing said plant cells in a plant-cell-culture medium, which is optionally supplemented with cytokinins, and optionally supplemented with herbicides, antibiotics or both, and,
   c. selecting regenerating plant cells.

33. The method of item 32, wherein said polypeptide is
   a. a polypeptide of at least 65% identity to SEQ ID NOs: 2 or 16; or
   b. a signature polypeptide:

(SEQ ID NO: 61)
   (X$^{13-23}$)RWNPT(KEQRIMLV)(EDNKQ)Q(ILMV)(EKNSTQR)

(MILV)L(DEKQST)(ADEHNST)L(FYW)(EQKR)(ADEKRQS)G (ILMV)RTP(AST)(AST)DQIQ(EKQR)I(AST)(AGST)(DEKQR)

L(AEQKRST)(ASFWY)YG(EQHKTY)IE(AGST)KNVFYWFQNHKAR (DEQKR)RQK(EKQR)(EQKR)(X$^{29-101}$)(DEKQR)(STACIGVLM

NQP)L(EPQKR)LFP(MILV)(X$^{13-57}$),

X represents any amino acids,
   the numbers following the X represent the range of the size of the domain represented by X,
   amino acids in each bracket represent alternatives for the respective single amino acid position represented by each bracket, and
   the polypeptide comprises an NLS with the proviso that the NLS does not change the specified amino acids.

34. The method of item 32, wherein the polypeptide that enables a transformant to regenerate in a medium that is deficient of one or more hormones or increases regeneration rate in a regular plant-cell-culture medium is a serine or threonine phosphatase.

35. The method of item 32, wherein said plant is cotton, maize, soybeans, rice, wheat, barley, sugarbeet, and oil palm.

36. The method of item 32, wherein said promoter is a chemically inducible promoter.

37. The method of item 32, wherein said promoter is a constitutive promoter.

38. The method of item 32, wherein said isolated polynucleotide and promoter are chemically excisable.

39. The method of item 32, wherein said plant-cell-culture medium contains antibiotics or herbicides.

40. The method of item 32, wherein said regular plant-cell-culture medium contains cytokinin.

41. The method of item 32, wherein said transformed cells are regenerated via somatic embryogenesis.

42. The method of item 32, wherein said transformed cells are regenerated via organogenesis.

43. The isolated polynucleotide of items 1, wherein the polypeptide encoded by said polynucleotides recited by d promotes plant regeneration, induces plant regeneration in the absence of one or more exogenous hormones or in the trace amount of them, or increases plant transformation efficiency.

44. The isolated polypeptide of item 15, wherein the polypeptide recited by c above promotes plant regeneration, induces plant regeneration in the absence of one or more exogenous hormones or in the trace amount of them, or increases plant transformation efficiency.

45. A method of improving plant transformation efficiency comprising the steps of
   a. transforming plant cells with vectors, wherein said vector comprises:
      i. the isolated polynucleotide encoding a serine/threonine phosphatase, and
      ii. a promoter that is active in a plant and operably linked to said isolated polynucleotide,
   b. culturing said plant cells in a plant-cell-culture medium, which is optionally supplemented with cytokinins, and optionally supplemented with herbicides, antibiotics or both, and,
   c. selecting regenerating plant cells.

46. The method of item 45, wherein said theonine/serine phosphatase is the *arabidopsis* Poltergeist.

47. The method of item 45, wherein said theonine/serine phosphatase shares at least 65% identity to the *arabidopsis* Poltergeist.

48. The methods of item 46 or 47, wherein said phosphatase is preferably a mutant deleted in negative regulation domain.

The above items are not meant to be an exhaustive list of possible claims. For example, a polypeptide of at least 65% identity to SEQ ID NOs: 2 and 16 having the signature sequence is also contemplated. Further, the Markush group style representation of possible alternatives in a bracket is meant to represent individual species covered by the formulation, and should not be narrowly construed as if the alternatives in a bracket are meant to be a range.

REFERENCES

Ainley, W. M. and Key, J. L. (1990). Plant Mol. Biol. 14:949-966.
Aoyama, T. and Chua, N-H (1997). The Plant J. 11:605-612.
Aoyama, T., Dong, C-H, Wu, Y., Carabelli, M., Sessa, G., Ruberti, I, Morelli, G and Chua N-H. (1995). Plant Cell 7:1773-1785.
Imamura, A., Kiba, T., Tajima, Y., Yamashino, T. and Mizuno T. (2003). Plant Cell Physiol. 44(2): 122-131.
Banno, H, Ikeda, Y, Niu, Q. W. and Chua, N-H. (2001). Plant Cell. 13:2609-2618.
Barry, G. F., Rogers, S. G., Fraley, R. T. and Brand, L. (1984). Proc. Natl. Acad. Sci. USA 81:4776-4780.
Beato M (1989). Cell 56:335-344.
Bryant, J. and Leather, S. (1992). Trends Biotechnol. 10:274-275.
Chang, C. and Shockey, J. A. (1999). Curr. Opin. Plant Biol. 2:352-358.
Chuck, G., Lincoln, C. and Hake, S. (1996). The Plant Cell 8:1277-1289.
Clough, S. J. and Bent, A. (1998). Plant J. 16:735-743.
Cokol, M., Nair R., and Rost, B. (2000). EMBO Reports 1:411-415.
Ebinuma, H., Sugita, K., Matsunaga, E. and Yamakado, M. (1997). Proc. Natl. Acad. Sci. USA 94:2117-2121.
Endrizzi, et al., 1996, Plant Journal 10: 967-979;
Faiss, M., Zalubilova, J., Strnad, M and Schmulling, T. (1997). The Plant Journal 12:401-415.
Flavell, R. B., Dart, E., Fuchs, R. L. and Fraley, R. B. (1992). Bio/Technology 10:141-144.
Gatz, C. (1996). Curr. Opin. Biotechnol. 7:168-172.
Gatz, C., Frohberg, C. and Wendenburg, R. (1992). Plant J. 2:397-404.
Geer, L. Y., Domrachev, M., Lipman, D. J., Bryant, S. H. (2002). Genome Res. 2002 12:1619-23.
Gehring, W. J., Affolter, M., Burglin, T. (1994). Trends Biotechnol. 10:382.
Haecker, A., Gross-Hardt R, Geiges, B., Sarkar, A, Breuninger, H., Herrmann, M., Laux, T. (2004). Development. 131:657-68.
Henikoff, S., and Henikoff, J. G. (1992). Amino acid substitution matrces for protein blocks. Proc. Natl. Acad. Sci. USA 89:10915-10919.
Hwang, I. and Sheen, J. (2001). Nature 413:383-9.

Ji, L. and Cai, L. (2004). A method for high efficiency transformation and regeneration of plant suspension cell cultures. (submitted for PCT patent application)

Kakimoto, T. (1996). Science 274:982-985.

Kamiya, N., Nagasaki, H., Morikami, A., Sato, Y., Matsuoka, M. (2003). Plant J. 35:429-41.

Kojima, S., Banno, H., Yoshioka, Y., Oka, A., Machida, C. and Machida, Y. (1999). DNA Res. 6:407-410.

Koncz, C., Martini, N., Mayerhofer, R., Koncz-Kalman, Z., Korber, H., Redei, G. P. and Schell, J. (1989). Proc. Natl. Acad. Sci. USA 86:8467-8471.

Laux, et al. (1996). Devlopment 122:87-96;

Lincoln, C., Long, J., Yamaguchi, J., Serikawa, K. and Hake, S. (1994). The Plant Cell 6:1859-1876.

Lloyd, A. M., Schena, M., Walbot, V. and Davis, R. W. (1994). Science 266:436-439.

Matsumoto, N., Okada, K. (2001). Genes Dev. 15:3355-64.

Mayer, et al. (1998). Cell 95: 805-815

Mett, V. L., Lockhead, L. P. and Reynolds, P. H. S. (1993). Proc. Natl. Acad. Sci. USA 90:4567-4571.

Okamuro, J. K., Caster, B., Villarroel, R., Van Montagu, M. and Jofuku, K. D. (1997). Proc. Natl. Acad. Sci. USA 94:7076-7081.

Ooms, G., Kaup, A. and Roberts, J. (1983). Theor. Appl. Genet. 66:169-172.

Picard, D. (1993). Trends Cell Biol. 3:278-280.

Riechmann, J. L. and Meyerowitz, E. M. (1998). Biol. Chem. 379:633-646.

Riou-Khamlichi, C., Huntley, R., Jacqmard, A. and Murray, J. A. (1999). Science 283:1541-1544.

Schena, M., Lloyd, A. M. and Davis, R. W. (1991). Proc. Natl. Acad. Sci. USA 88:10421-10425.

Sato, S., Kato, T. Tabata, S., Oka, A. (2001). Science 294:16.

Smigocki, A. C. and Owens, L. D. (1988). Proc. Natl. Acad. Sci. USA 85:5131-5135.

Smigocki, A. C. and Owens, L. D. (1989). Plant Physiol. 91:808-811.

Tinland, B., Koukolíková-Nicola, Z., Hall, M. N., and Hohn, B. (1992). Proc. Natl. Acad. Sci. USA 89: 7442-7446.

Valvekens, D., Montague, M. V. and Lijsbettens, M. V. (1988). Proc. Natl. Acad. Sci, USA. 85:5536-5540.

Weinmaun, P., Gossen, M., Hillen, W., Bujard, H. and Gatz, C. (1994). Plant J. 5:559-569.

Yasutani I, Ozawa S, Nishida T, Sugiyarna M and Komamine A (1994). Plant Physiol. 105:815-822.

Yoder, J. I. and Goldsbrough, A. P. (1994). Bio/Technology 12:263-267.

Yu, L. P., Miller, A. K. and Clark S. E. (2003). Current Biol. 3:179-188.

Zuo, J. and Chua, N-H. (2000). Current Opinion in Biotechnology 11:146-151.

Zuo J, Niu, Q. W. and Chua, N. H. (2000). Plant J. 24:265-273.

Zuo J, Niu, Q. W., Frugis, G., Chua, N. H. (2002). Plant J. 30:349-59.

Zuo, J., Niu, Q. W., Moller, S. G. and Chua, N. H. (2001). Nat. Biotechnol. 19:157-161.

---

We claim:

1. A method of selecting a plant cell transformant comprising the steps of
   a. transforming plant cells with a vector, wherein said vector comprises
      i. an isolated polynucleotide encoding a polypeptide that enables a transformant to regenerate in a medium deficient of one or more hormones, wherein said polynucleotide encodes SEQ ID NO: 2, and
      ii. a promoter that is active in a plant and operably linked to said isolated polynucleotide,
   b. culturing said plant cells in a plant-cell-culture medium that is deficient of one or more hormones, and
   c. selecting regenerating plant cells.

2. The method of claim 1, wherein said vector further comprises a polynucleotide of interest.

3. The method of claim 1, wherein said promoter is a chemically inducible promoter.

4. The method of claim 1, wherein said promoter is a constitutive promoter.

5. The method of claim 1, wherein said isolated polynucleotide and promoter are chemically excisable.

6. The method of claim 1, wherein said plant-cell-culture medium does not contain any antibiotics or herbicides.

7. The method of claim 1, wherein said plant-cell-culture medium does not contain one or more hormones.

8. A method of improving plant transformation efficiency comprising the steps of
   a. transforming plant cells with a vector, wherein said vector comprises:
      i. an isolated polynucleotide encoding a polypeptide that enables a transformant to regenerate in a medium that is deficient of one or more hormones or increases regeneration rate in a regular plant-cell-culture medium, wherein said polynucleotide encodes SEQ ID NO: 2, and
      ii. a promoter that is active in a plant and operably linked to said isolated polynucleotide,
   b. culturing said plant cells in a plant-cell-culture medium, which is optionally supplemented with cytokinins, and optionally supplemented with herbicides, antibiotics or both, and,
   c. selecting regenerating plant cells.

9. The method of claim 8, wherein said plant is cotton, maize, soybeans, rice, wheat, barley, sugarbeet, or oil palm.

10. The method of claim 8, wherein said promoter is a chemically inducible promoter.

11. The method of claim 8, wherein said promoter is a constitutive promoter.

12. The method of claim 8, wherein said isolated polynucleotide and promoter are chemically excisable.

13. The method of claim 8, wherein said plant-cell-culture medium contains antibiotics or herbicides.

14. The method of claim 8, wherein said regular plant-cell-culture medium contains cytokinin.

15. The method of claim 8, wherein said transformed cells are regenerated via somatic embryogenesis.

16. The method of claim 8, wherein said transformed cells are regenerated via organogenesis.

* * * * *

UNITED STATES PATENT AND TRADEMARK OFFICE
CERTIFICATE OF CORRECTION

| | | |
|---|---|---|
| PATENT NO. | : 8,586,824 B2 | Page 1 of 1 |
| APPLICATION NO. | : 12/223929 | |
| DATED | : November 19, 2013 | |
| INVENTOR(S) | : Ji et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1492 days.

Signed and Sealed this
Thirty-first Day of March, 2015

Michelle K. Lee
*Director of the United States Patent and Trademark Office*